United States Patent
Fudaba et al.

(10) Patent No.: US 9,827,047 B2
(45) Date of Patent: Nov. 28, 2017

(54) CONTROL APPARATUS AND CONTROL METHOD OF INSERTION APPARATUS, INSERTION APPARATUS HAVING CONTROL APPARATUS, CONTROL PROGRAM FOR INSERTION APPARATUS, AND CONTROLLING INTEGRATED ELECTRONIC CIRCUIT OF INSERTION APPARATUS

(71) Applicant: PANASONIC INTELLECTUAL PROPERTY MANAGEMENT CO., LTD., Osaka (JP)

(72) Inventors: Yudai Fudaba, Osaka (JP); Yuko Tsusaka, Osaka (JP); Taichi Sato, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 617 days.

(21) Appl. No.: 14/293,236

(22) Filed: Jun. 2, 2014

(65) Prior Publication Data

US 2014/0288525 A1    Sep. 25, 2014

Related U.S. Application Data

(63) Continuation of application No. PCT/JP2013/004147, filed on Jul. 4, 2013.

(30) Foreign Application Priority Data

Jul. 10, 2012   (JP) .................................. 2012-154847

(51) Int. Cl.
*A61B 1/00* (2006.01)
*A61B 1/04* (2006.01)
(Continued)

(52) U.S. Cl.
CPC ........ *A61B 19/2203* (2013.01); *A61B 1/0016* (2013.01); *A61B 5/066* (2013.01);
(Continued)

(58) Field of Classification Search
CPC ... A61B 1/0016; A61B 1/0051; A61B 1/0052; A61B 1/31; A61B 1/005; A61B 1/00147; A61B 1/00156
See application file for complete search history.

(56) References Cited

U.S. PATENT DOCUMENTS

| | | |
|---|---|---|
| 5,060,632 A | 10/1991 | Hibino et al. |
| 5,681,260 A | 10/1997 | Ueda et al. |

(Continued)

FOREIGN PATENT DOCUMENTS

| | | |
|---|---|---|
| JP | 4-2319 | 1/1992 |
| JP | 4-24016 | 1/1992 |

(Continued)

OTHER PUBLICATIONS

International Preliminary Report on Patentability and Written Opinion of the International Searching Authority dated Jan. 22, 2015 in International (PCT) Application No. PCT/JP2013/004147.

(Continued)

*Primary Examiner* — Alexandra Newton
(74) *Attorney, Agent, or Firm* — Wenderoth, Lind & Ponack, L.L.P.

(57) ABSTRACT

A control apparatus of an insertion apparatus in which a state specifying unit specifies a state of an insertion member to carry out vibration control depending on the state, thereby removing getting-stuck of a tip of the insertion member with a vibration having such a proper magnitude as not to cause an overload in a case where the tip of the insertion member is gotten stuck.

17 Claims, 56 Drawing Sheets

(51) Int. Cl.
  *A61B 19/00*    (2006.01)
  *A61B 5/06*    (2006.01)
  *G05B 19/423*    (2006.01)
  *A61B 34/32*    (2016.01)
  *A61M 25/01*    (2006.01)
  *A61B 17/22*    (2006.01)
  *A61B 34/30*    (2016.01)

(52) U.S. Cl.
  CPC .............. *A61B 34/30* (2016.02); *A61B 34/32* (2016.02); *G05B 19/423* (2013.01); *A61B 2017/22001* (2013.01); *A61B 2017/22014* (2013.01); *A61B 2034/301* (2016.02); *A61M 25/01* (2013.01); *A61M 2025/0166* (2013.01); *G05B 2219/37569* (2013.01); *G05B 2219/39195* (2013.01); *G05B 2219/40028* (2013.01); *G05B 2219/45118* (2013.01)

(56) References Cited

U.S. PATENT DOCUMENTS

| | | |
|---|---|---|
| 2009/0149703 A1 | 6/2009 | Tanaka |
| 2009/0209900 A1 | 8/2009 | Carmeli et al. |
| 2009/0221869 A1 | 9/2009 | Tanaka |

FOREIGN PATENT DOCUMENTS

| | | |
|---|---|---|
| JP | 4-357925 | 12/1992 |
| JP | 5-211993 | 8/1993 |
| JP | 2007-135783 | 6/2007 |
| JP | 2008-136628 | 6/2008 |
| JP | 2008-264910 | 11/2008 |
| JP | 2008-539935 | 11/2008 |

OTHER PUBLICATIONS

International Search Report dated Oct. 15, 2013 in International (PCT) Application No. PCT/JP2013/004147.

Fig.2

| TIME(ms) | POSITION(mm) (x,y,z) | ORIENTATION(rad) (r_x,r_y,r_z) | VELOCITY(mm/ms) (v_x,v_y,v_z) | ANGULAR VELOCITY(rad/ms) ($\omega_x, \omega_y, \omega_z$) |
|---|---|---|---|---|
| .. .. | .. .. | .. .. | .. .. | .. .. |
| 1821 | 112.2, 65.5, -8.5 | 0.07, -0.87, 1.22 | 0.11, -0.21, 0.38 | 0.015, -0.012, 0.010 |
| 1822 | 113.1, 64.8, -8.5 | 0.06, -0.85, 1.27 | 0.95, -0.73, 0.00 | -0.018, 0.022, 0.059 |
| 1823 | 113.5, 64.0, -8.0 | 0.05, -0.82, 1.28 | 0.42, -0.82, 0.50 | -0.010, 0.026, 0.017 |
| .. .. | .. .. | .. .. | .. .. | .. .. |

| TIME(ms) | INSERTION INFORMATION |
|---|---|
| ⋮ | ⋮ |
| 3652 | 1 |
| 3653 | 1 |
| 3654 | 1 |
| 3655 | 0 |
| 3656 | 0 |
| 3657 | 0 |
| 3658 | 0 |
| 3659 | 0 |
| 3660 | 0 |
| ⋮ | ⋮ |

Fig.7
| TIME(ms) | INSERTION MEMBER MOVEMENT INFORMATION |
|---|---|
| ⋮ | ⋮ |
| 3652 | 0 |
| 3653 | 0 |
| 3654 | 0 |
| 3655 | 0 |
| 3656 | 0 |
| 3657 | 0 |
| 3658 | 1 |
| 3659 | 1 |
| 3660 | 1 |
| ⋮ | ⋮ |
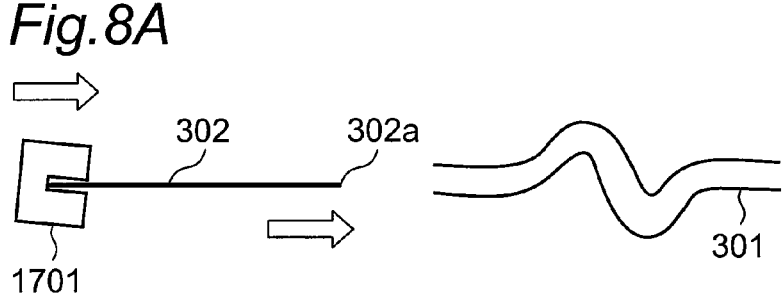
Fig.8A
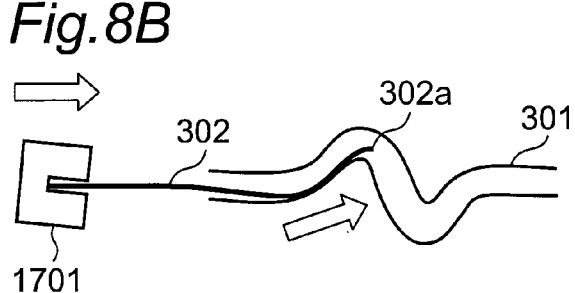
Fig.8B

| INSERTION INFORMATION | INSERTION MEMBER MOVEMENT INFORMATION | CONTROL INFORMATION | VIBRATION INFORMATION |
|---|---|---|---|
| 1 | 1 | 0 | 0 |

| INSERTION INFORMATION | INSERTION MEMBER MOVEMENT INFORMATION | CONTROL INFORMATION | VIBRATION INFORMATION |
|---|---|---|---|
| 1 | 0 | 1 | 15 |

*Fig.10C*
| INSERTION INFORMATION | INSERTION MEMBER MOVEMENT INFORMATION | CONTROL INFORMATION | VIBRATION INFORMATION |
|---|---|---|---|
| 0 | 0 | 1 | 30 |
*Fig.10D*
| INSERTION INFORMATION | INSERTION MEMBER MOVEMENT INFORMATION | CONTROL INFORMATION | VIBRATION INFORMATION |
|---|---|---|---|
| 0 | 1 | 0 | 0 |
*Fig.11*
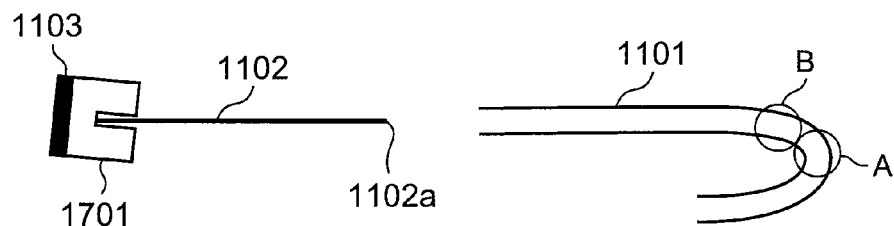
*Fig.12A*
*Fig.12B*
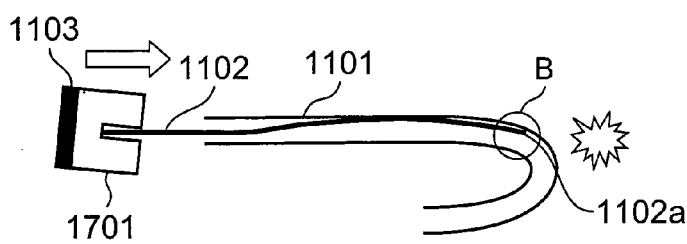

Fig.13
| VIBRATION START POSITION | MAGNITUDE OF FORCE (N) |
|---|---|
| A | 0.60 |
| B | 0.14 |
Fig.14A
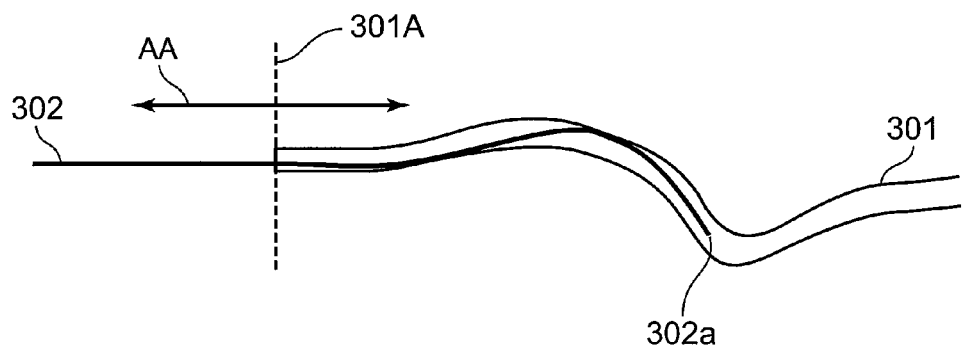
Fig.14B
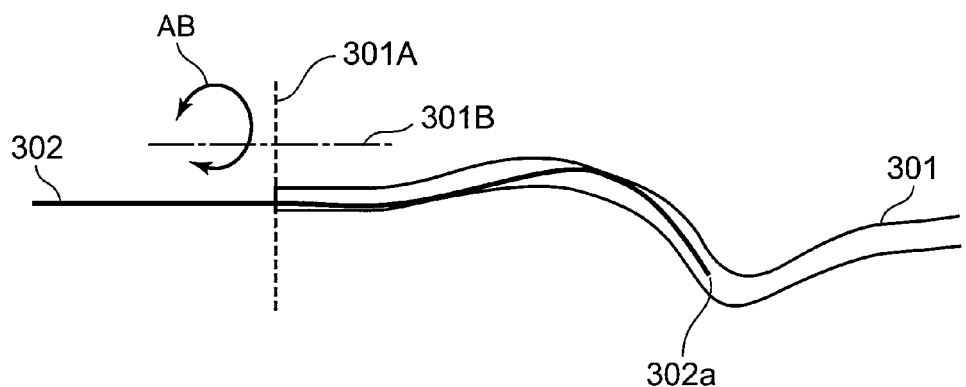

Fig.15D
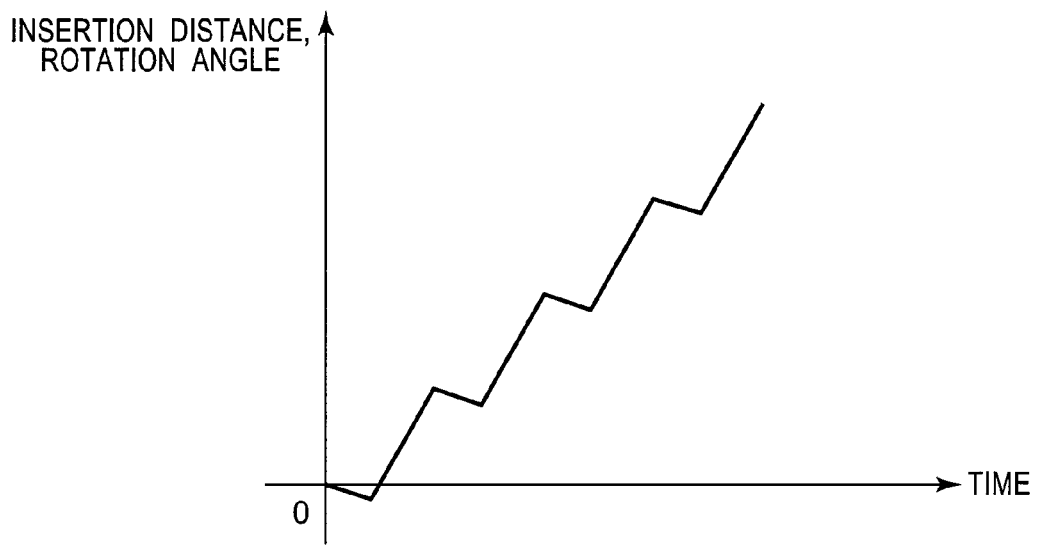
Fig.15E
Fig.16A
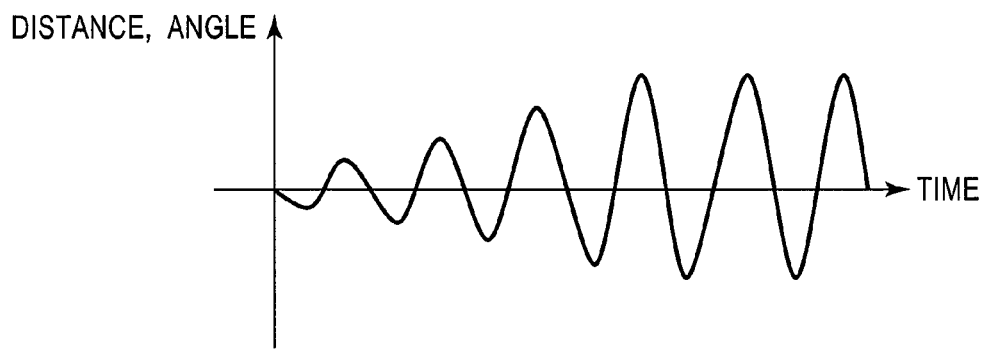
| AMPLITUDE | INSERTION DISTANCE (mm) |
|---|---|
| LARGE | 125.37 |
| SMALL | 115.38 |

Fig.16B

| CYCLE | INSERTION DISTANCE (mm) |
|---|---|
| HIGH | 125.60 |
| LOW | 119.10 |

Fig.16C

| RATIO OF ADVANCE | INSERTION DISTANCE (mm) |
|---|---|
| LARGE | 132.62 |
| SMALL | 125.78 |

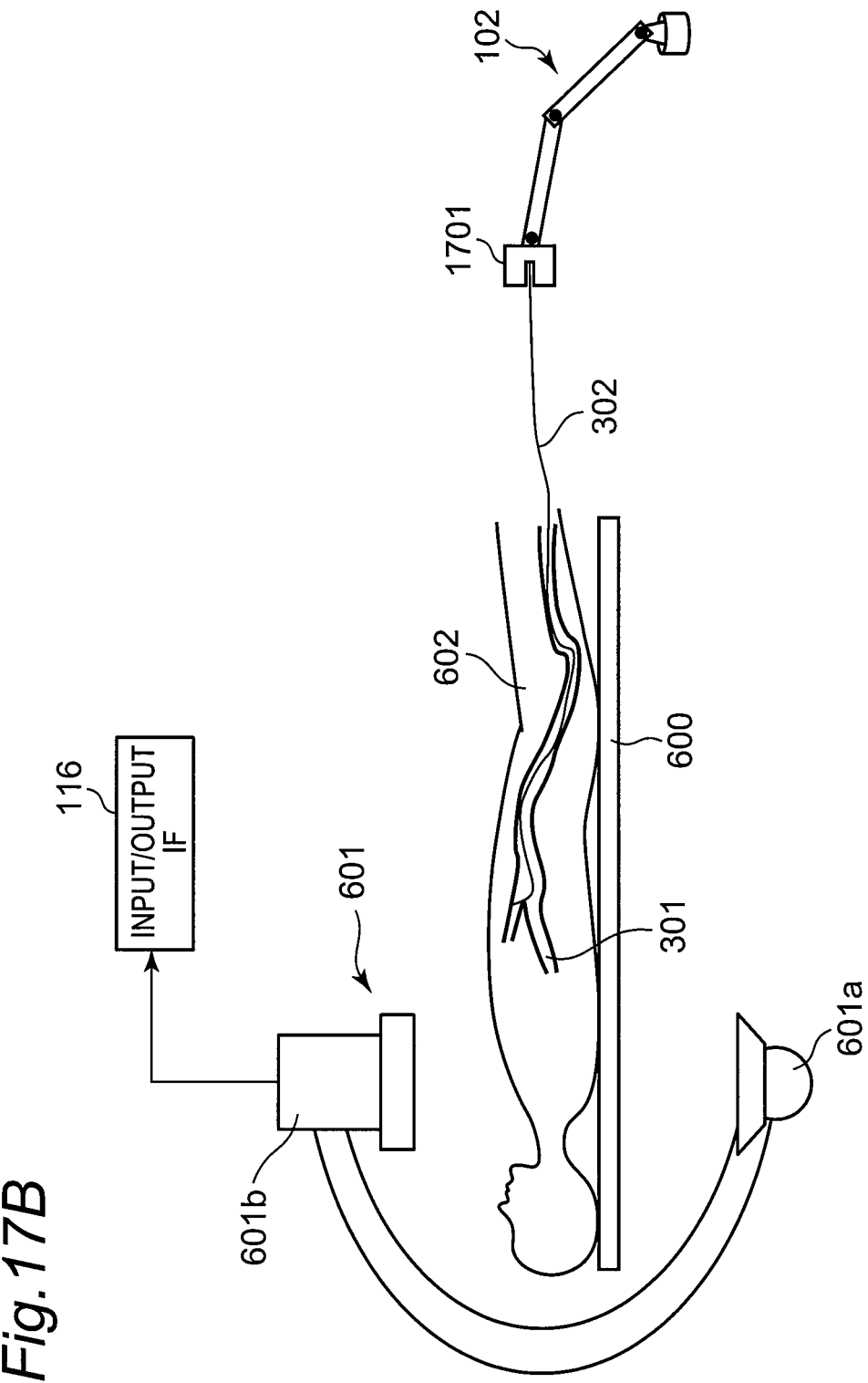

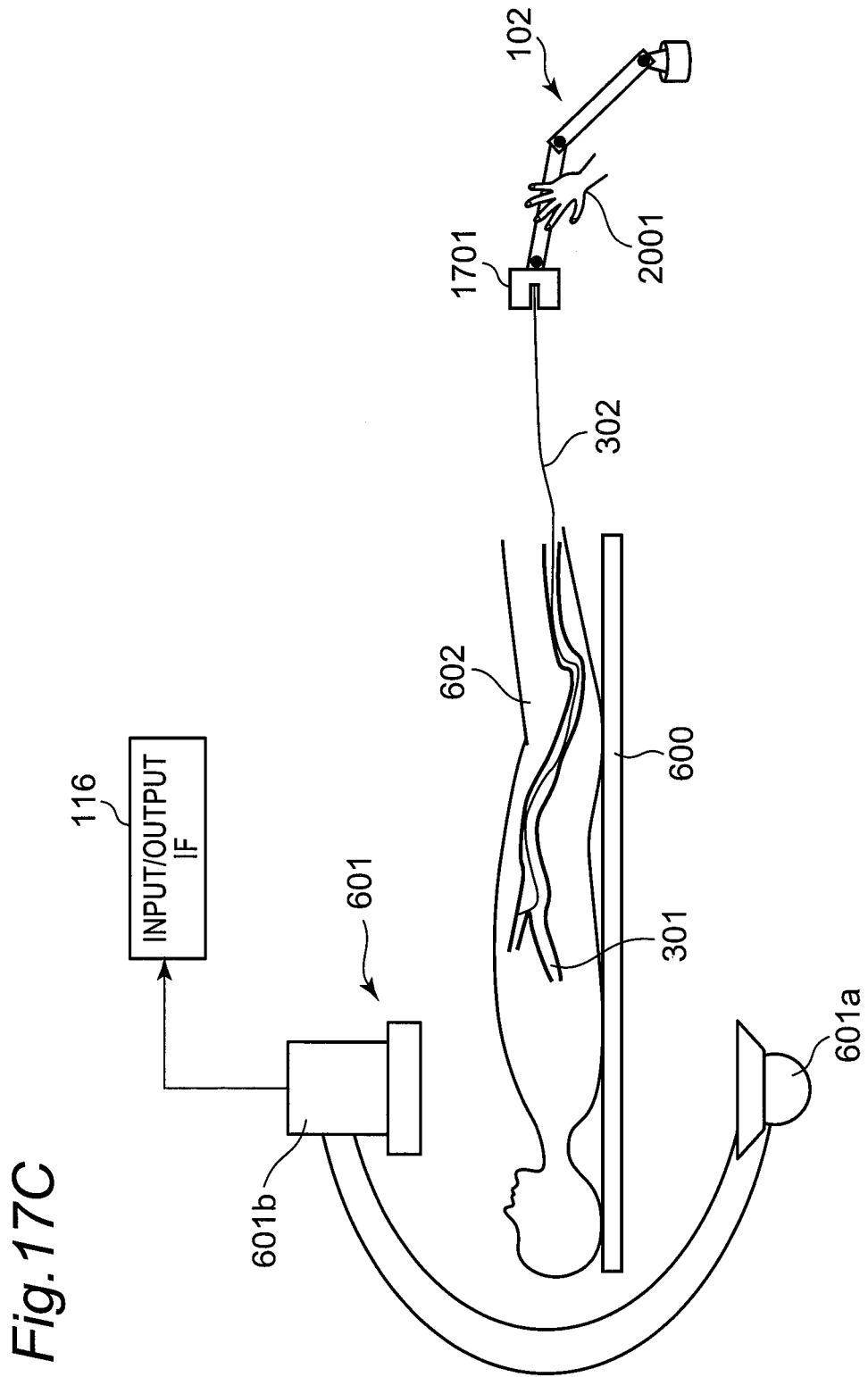

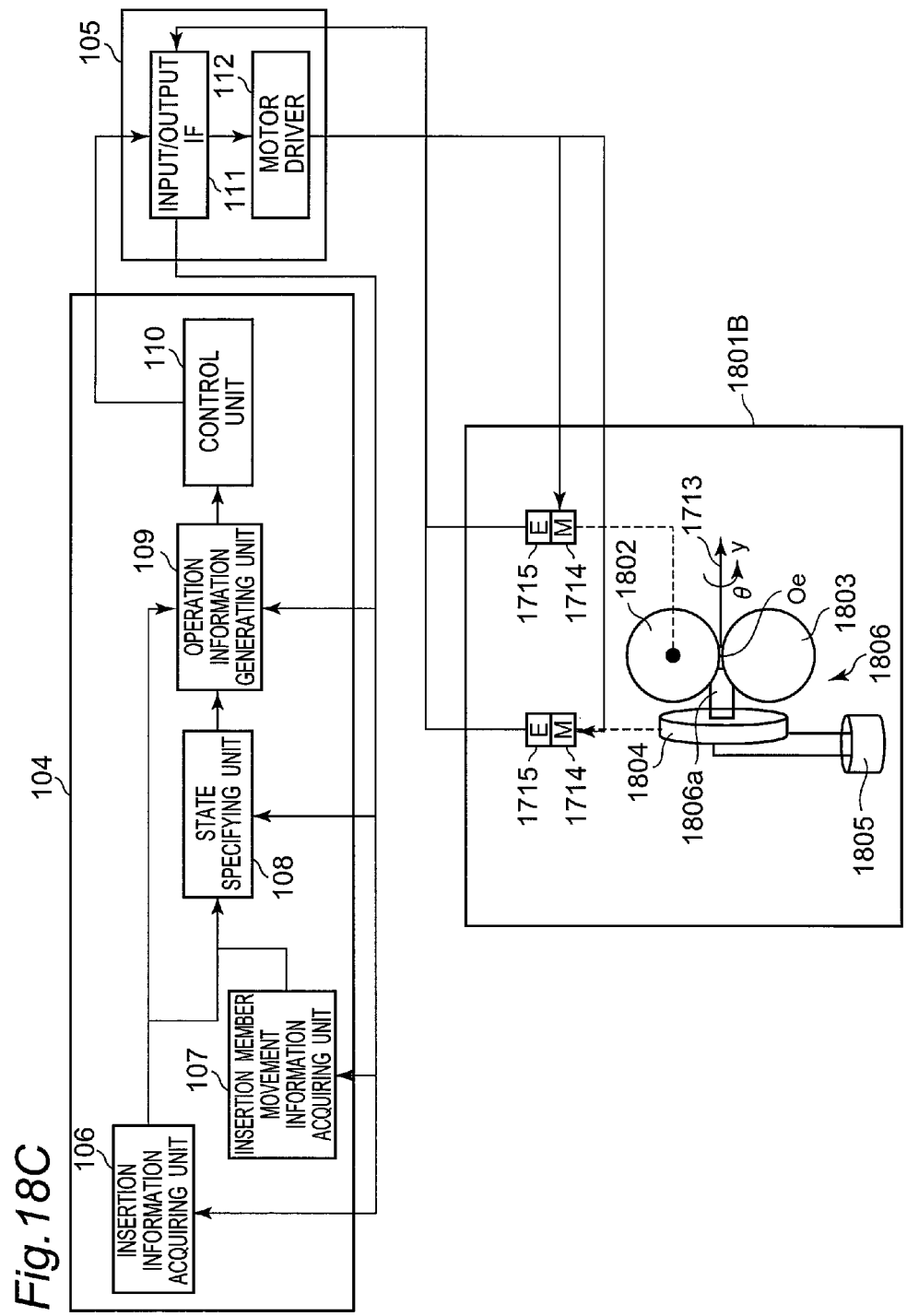

*Fig.23A*

| INSERTION INFORMATION | INSERTION MEMBER MOVEMENT INFORMATION | CONTROL INFORMATION | VIBRATION INFORMATION |
|---|---|---|---|
| 1 | 1 | 1 | 5 |

*Fig.23B*

| INSERTION INFORMATION | INSERTION MEMBER MOVEMENT INFORMATION | CONTROL INFORMATION | VIBRATION INFORMATION |
|---|---|---|---|
| 1 | 0 | 1 | 15 |

*Fig.23C*

| INSERTION INFORMATION | INSERTION MEMBER MOVEMENT INFORMATION | CONTROL INFORMATION | VIBRATION INFORMATION |
|---|---|---|---|
| 0 | 0 | 1 | 30 |

*Fig.23D*

| INSERTION INFORMATION | INSERTION MEMBER MOVEMENT INFORMATION | CONTROL INFORMATION | VIBRATION INFORMATION |
|---|---|---|---|
| 0 | 1 | 0 | 0 |

Fig.26

| VIBRATION START POSITION | INSERTION DISTANCE (mm) |
|---|---|
| A | 124.64 |
| B | 124.87 |
| C | 126.92 |

Fig.29

| INSERTION INFORMATION | INSERTION MEMBER MOVEMENT INFORMATION |
|---|---|
| 1 | 1 |
| 1 | 0 |
| 0 | 0 |
| 1 | 0 |

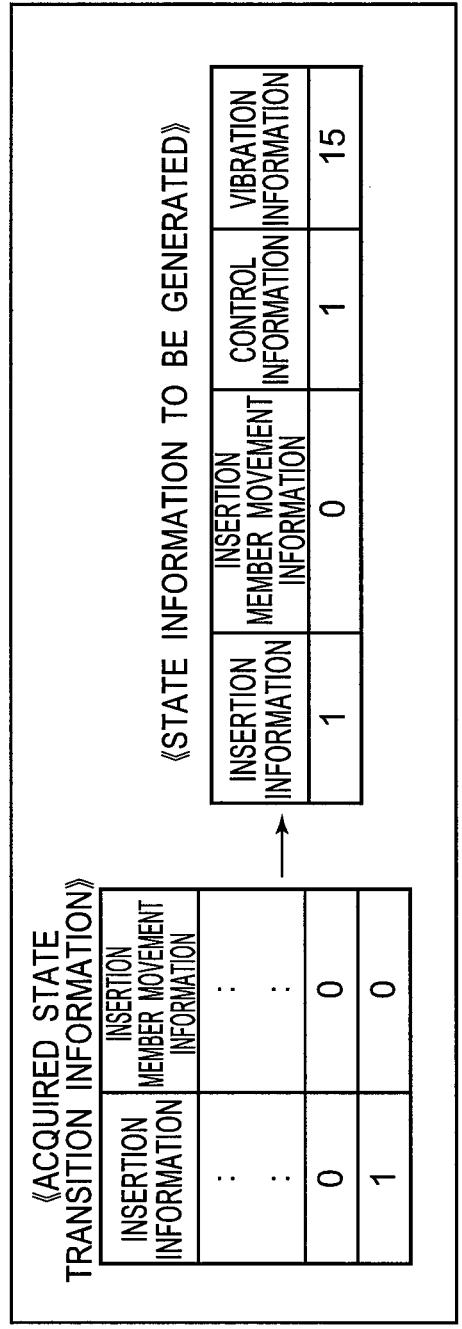

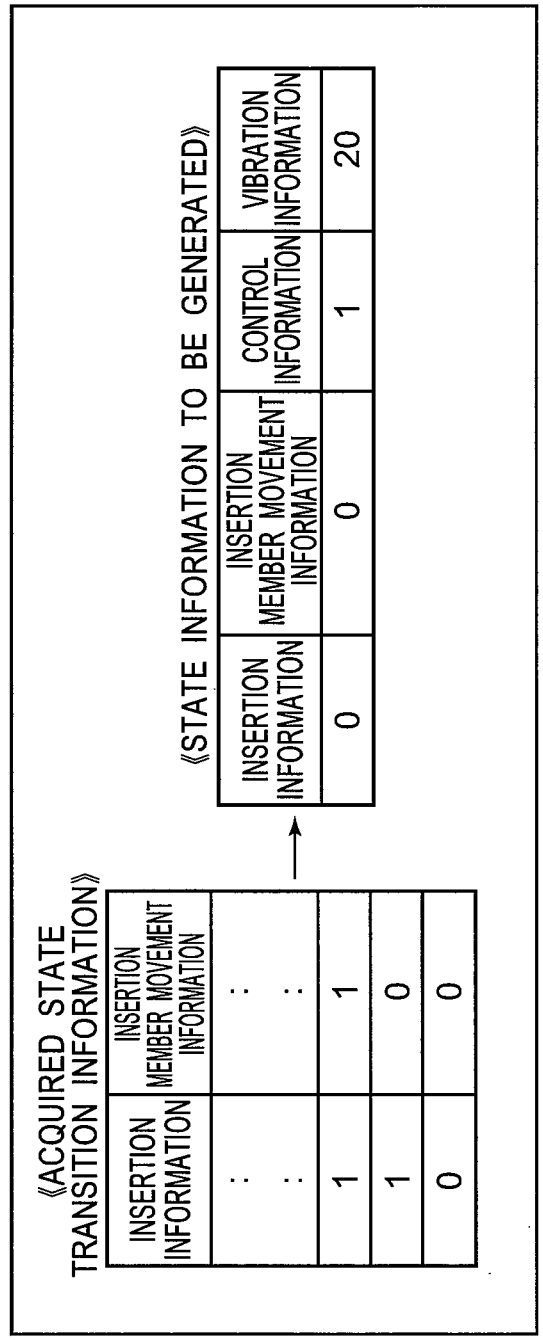

Fig.41
| TIME OF VIBRATION CONTROL START | INSERTION DISTANCE (mm) | MAGNITUDE OF FORCE (N) |
|---|---|---|
| MOVE | 126.92 | 0.41 |
| STOP | 123.68 | 0.46 |
Fig.42A
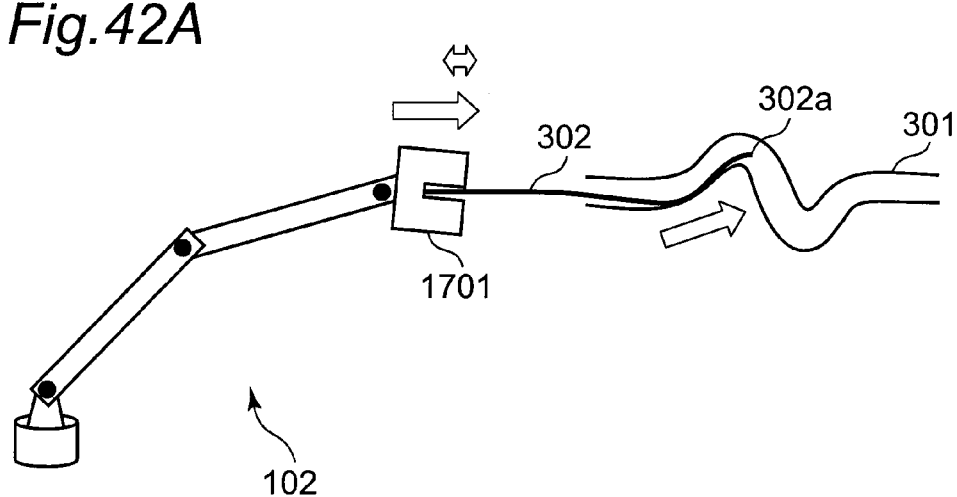
Fig.42B
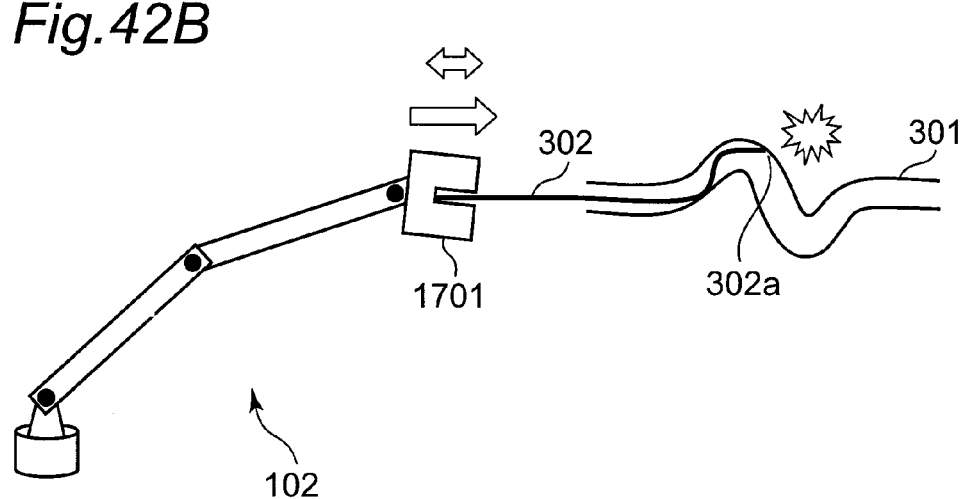

Fig.49

| INSERTION DISTANCE (mm) | HUMAN BODY REGION | ADDITIONAL VIBRATION (/mm) |
|---|---|---|
| ⋮ | ⋮ | ⋮ |
| 1020 ~ 1045 | UMBILICAL VEIN | +0.1 |
| 1046 ~ 1069 | PORTAL VEIN | +0.1 |
| 1070 ~ 1100 | VENOUS DUCT | +0.2 |
| 1101 ~ 1151 | INFERIOR VENA CAVA | +0.2 |
| 1152 ~ | RIGHT ATRIUM | −0.1 |

CONTROL APPARATUS AND CONTROL METHOD OF INSERTION APPARATUS, INSERTION APPARATUS HAVING CONTROL APPARATUS, CONTROL PROGRAM FOR INSERTION APPARATUS, AND CONTROLLING INTEGRATED ELECTRONIC CIRCUIT OF INSERTION APPARATUS

CROSS-REFERENCE TO RELATED APPLICATIONS

This is a continuation application of International Application No. PCT/JP2013/004147, with an international filing date of Jul. 4, 2013, which claims priority of Japanese Patent Application No.: 2012-154847 filed on Jul. 10, 2012, the content of which is incorporated herein by reference.

TECHNICAL FIELD

The technical field relates to a control apparatus and a control method of an insertion apparatus, an insertion apparatus having the control apparatus of an insertion apparatus, a control program for the insertion apparatus, and a controlling integrated electronic circuit of the insertion apparatus, each of which generates an operation of the insertion apparatus for inserting an insertion member of a catheter or an endoscope into a body lumen.

BACKGROUND ART

There is proposed an apparatus for detecting movement of a tip part of an endoscope, and detecting getting-stuck of the tip when the amount of the movement of the tip part is diminished in the case in which a catheter or the like is inserted into a blood vessel in medical treatment using the catheter or the endoscope (see Patent Literature 1). Referring to the apparatus, in the case in which the getting-stuck is detected, a vibration of the tip part is controlled in an advancing direction to remove the getting-stuck and to smoothly carry out the movement.

On the other hand, in an example of a work for fitting a rigid body target in an insertion target through a robot, there is proposed an apparatus for detecting a stuck state if the velocity of a hand tip of the robot is less than a threshold or if a value of a force sensor attached to the hand tip of the robot is greater than a threshold (see Patent Literature 2). In the case in which the stuck state is detected, the apparatus continuously carries out an inserting operation by a robot and applies a vibration force which has a magnitude and a direction varied cyclically. Thus, vibration control is applied to eliminate the stuck state in the fitting work more surely in a short time.

CITATION LIST

Patent Literature

[Patent Literature 1] Unexamined Japanese Patent Publication No. 4-24016 (1992)
[Patent Literature 2] Unexamined Japanese Patent Publication No. 2008-264910
[Patent Literature 3] Unexamined Japanese Patent Publication No. 2007-135783

SUMMARY OF THE INVENTION

Referring to the Patent Literature 1, only the tip part of the endoscope is set to be the detection target. In the case in which flexure is caused in the middle portion between the tip part and a hand holding portion of the endoscope in the work for inserting the endoscope, it is impossible to distinguish a state of "stop" (a state in which only the tip part of the endoscope is not moved but the hand holding portion of the endoscope is moved) and a state of "complete stop" (a state in which neither the tip part nor the hand holding portion of the endoscope are moved) in the inserting work from each other. For this reason, although a necessary vibration magnitude is varied depending on the respective states, the same vibration control is carried out without distinction of these two states. In some cases in which the vibration magnitude is adapted to either of the states, getting-stuck cannot be removed or an overload occurs.

Referring to the Patent Literature 2, the stuck state is detected with only the hand holding portion of the robot set as the detecting target because the target is a rigid body. For this reason, in the case in which the target is a flexible member and is flexed in the middle portion, it is impossible to distinguish a "complete stop" (a state in which neither the hand holding portion of the robot nor the target are moved) and a state of "movement of only the target" (a state in which the hand holding portion of the robot is not moved but only the target is moved) from each other. For this reason, the same vibration control is carried out without distinction of these two states. In the former state, the control is disabled. When the vibration control is applied, therefore, an action for amplifying a jumping state of the flexible member is exerted so that a dangerous condition is brought.

Referring to the Patent Literature 3, there is simply disclosed an insertion monitoring apparatus which can more surely confirm insertion aid information corresponding to a predetermined response operation state of an inserting unit to an insertion manipulation or the like, and a relationship with vibration control is not disclosed at all.

One non-limiting and exemplary embodiment provides a control apparatus and a control method of an insertion apparatus, an insertion apparatus having the control apparatus, a control program for the insertion apparatus, and a controlling integrated electronic circuit of the insertion apparatus which can carry out vibration control in such a proper vibration magnitude as not to cause an overload and can remove getting-stuck of an insertion member of a catheter or an endoscope irrespective of the state of the insertion member when the getting-stuck is detected in a work for inserting the insertion member.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

In one general aspect, the techniques disclosed here feature: a control apparatus of an insertion apparatus configured to insert an insertion member of a catheter or an endoscope into a body lumen, the control apparatus comprising:

a tip movement information acquiring unit that acquires tip movement information indicative of presence of movement in the body lumen of a tip of the insertion member;

a non-tip area movement information acquiring unit that acquires non-tip area movement information indicative of presence of a moving operation in the body lumen of a non-tip area other than the tip of the insertion member;

a state specifying unit that, by using the non-tip area movement information acquired by the non-tip area movement information acquiring unit and the tip movement information acquired by the tip movement information acquiring unit, (a) specifies as a first tip stop state for vibrating the insertion member, a case where the non-tip area of the insertion member is moved and the tip of the insertion member is not moved, and (b) specifies as a second tip stop state for vibrating the insertion member more greatly than in the first tip stop state of (a), a case where the non-tip area of the insertion member is not moved and the tip of the insertion member is not moved;

an operation information generating unit that generates operation information about the insertion apparatus to execute the first tip stop state of (a) or the second tip stop state of (b) which is specified by the state specifying unit; and a control unit that controls an operation of the insertion member based on the operation information generated by the operation information generating unit.

These general and specific aspects may be implemented using a system, a method, and a computer program, and any combination of systems, methods, and computer programs.

According to the control apparatus and the control method of the insertion apparatus, the insertion apparatus having the control apparatus, the control program for the insertion apparatus, and the controlling integrated electronic circuit of the insertion apparatus in accordance with the aspects of the present disclosure, a vibration magnitude is adjusted for vibration control depending on a state of the insertion member to carry out vibration control when the insertion member causes getting-stuck in a work for inserting the insertion member. Consequently, it is possible to remove the getting-stuck with a vibration having such a proper magnitude as not to cause an overload. Thus, it is possible to achieve the inserting work.

BRIEF DESCRIPTION OF THE DRAWINGS

These and other aspects and features of the present disclosure will become clear from the following description taken in conjunction with the embodiments thereof with reference to the accompanying drawings, in which:

FIG. 2 is a data diagram showing operation information in the robot according to the first embodiment of the present disclosure;

FIG. 7 is a data diagram showing insertion member moving information in the robot according to the first embodiment of the present disclosure;

FIG. 8A is an explanatory view representing a state in the robot according to the first embodiment of the present disclosure;

FIG. 8B is an explanatory view representing a state in the robot according to the first embodiment of the present disclosure;

FIG. 10C is a data diagram showing the state information in the robot according to the first embodiment of the present disclosure;

FIG. 10D is a data diagram showing the state information in the robot according to the first embodiment of the present disclosure;

FIG. 11 is a view for explaining an insertion experiment of a wire into a tube in the robot according to the first embodiment of the present disclosure;

FIG. 12A is a view for explaining a vibration start position in the insertion experiment of the wire into the tube in the robot according to the first embodiment of the present disclosure;

FIG. 12B is a view for explaining the vibration start position in the insertion experiment of the wire into the tube in the robot according to the first embodiment of the present disclosure;

FIG. 13 is a view showing an experimental result in the insertion experiment of the wire into the tube in the robot according to the first embodiment of the present disclosure;

FIG. 14A is a view for explaining a vibration direction in the robot according to the first embodiment of the present disclosure;

FIG. 14B is a view for explaining the vibration direction in the robot according to the first embodiment of the present disclosure;

FIG. 15D is a chart for explaining the magnitude of the vibration in the robot according to the first embodiment of the present disclosure;

FIG. 15E is a chart for explaining the magnitude of the vibration in the robot according to the first embodiment of the present disclosure;

FIG. 16A is a view showing an experimental result for each parameter in the insertion experiment of the wire into the tube in the robot according to the first embodiment of the present disclosure;

FIG. 16B is a view showing an experimental result for each parameter in the insertion experiment of the wire into the tube in the robot according to the first embodiment of the present disclosure;

FIG. 16C is a view showing an experimental result for each parameter in the insertion experiment of the wire into the tube in the robot according to the first embodiment of the present disclosure;

FIG. 17B is a view for explaining a time of automatic reproduction using the robot arm in the robot according to the first embodiment of the present disclosure;

FIG. 17C is a view for explaining a time of manipulation using the robot arm in the robot according to the first embodiment of the present disclosure;

FIG. 18C is a view for explaining a 2-axial roller type feeding apparatus and a control apparatus body unit according to the first embodiment of the present disclosure;

FIG. 23A is a data diagram showing state information in the robot according to the modification example of the first embodiment of the present disclosure;

FIG. 23B is a data diagram showing the state information in the robot according to the modification example of the first embodiment of the present disclosure;

FIG. 23C is a data diagram showing the state information in the robot according to the modification example of the first embodiment of the present disclosure;

FIG. 23D is a data diagram showing the state information in the robot according to the modification example of the first embodiment of the present disclosure;

FIG. 26 is a view showing an experimental result in the insertion experiment of the wire into the tube in the robot according to the modification example of the first embodiment of the present disclosure;

FIG. 29 is a data diagram for state transition information in the robot according to the second embodiment of the present disclosure;

FIG. 32A is a view for explaining the method of generating state information (the newest state is a "first stop" state) in the robot according to the second embodiment of the present disclosure;

FIG. 33C is a view for explaining the method of generating state information (the newest state is the "second stop" state) in the robot according to the second embodiment of the present disclosure;

FIG. 41 is a view showing an experimental result in an insertion experiment of a wire into a tube in the robot according to the third embodiment of the present disclosure;

FIG. 42A is a view for explaining an operation procedure of a work for inserting a guide wire into a blood vessel (in automatic reproduction) in the robot according to the third embodiment of the present disclosure;

FIG. 42B is a view for explaining the operation procedure of the work for inserting the guide wire into the blood vessel (in the automatic reproduction) in the robot according to the third embodiment of the present disclosure;

FIG. 49 is a view for explaining an inserting position database for the robot arm in the robot according to the fifth embodiment of the present disclosure.

DETAILED DESCRIPTION

Figure 1A:
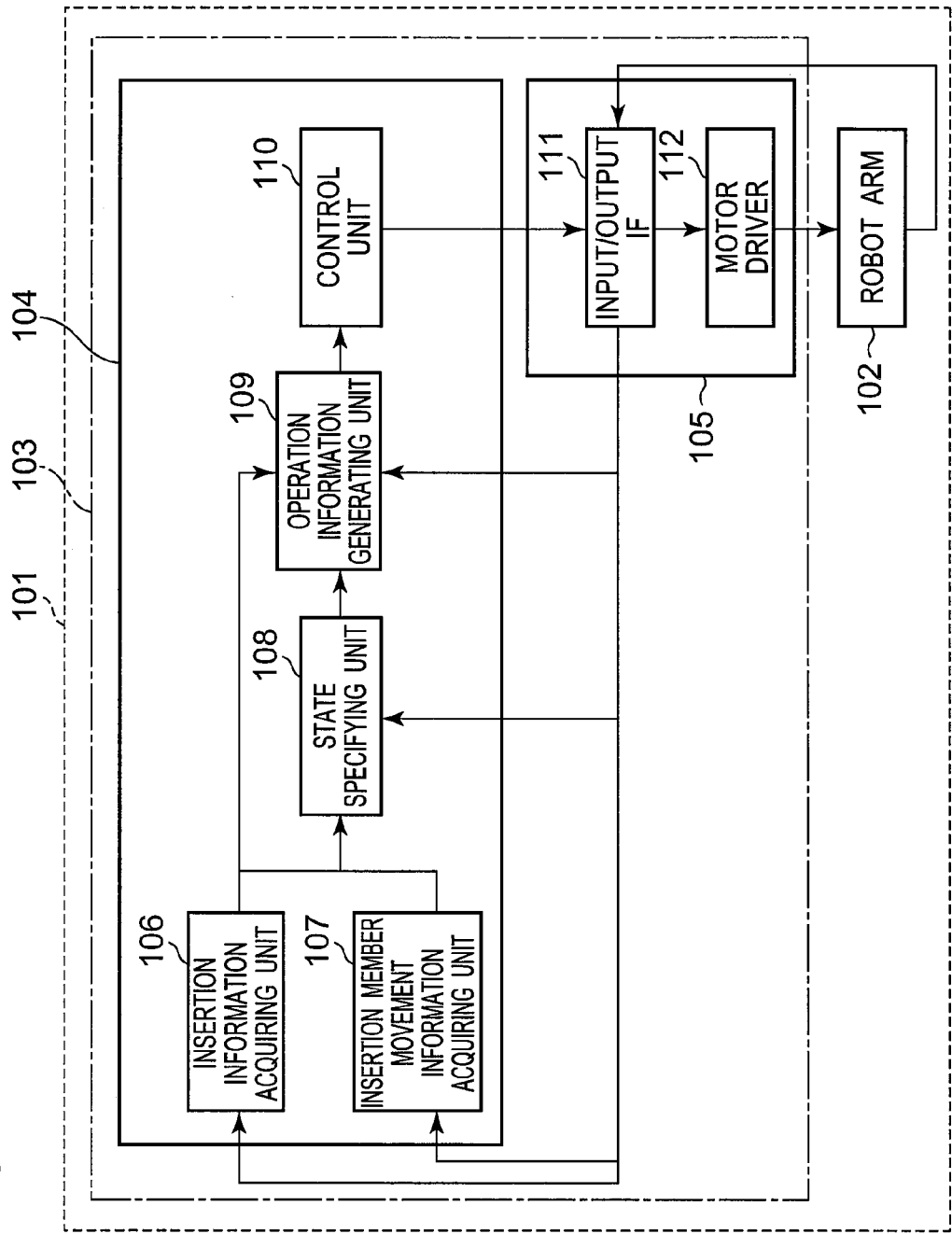
FIG. 1A is a block diagram showing a robot arm in a robot according to a first embodiment of the present disclosure.

Examples of the disclosed technique are as follows.

1st aspect: A control apparatus of an insertion apparatus configured to insert an insertion member of a catheter or an endoscope into a body lumen, the control apparatus comprising:

a tip movement information acquiring unit that acquires tip movement information indicative of presence of movement in the body lumen of a tip of the insertion member;

a non-tip area movement information acquiring unit that acquires non-tip area movement information indicative of presence of a moving operation in the body lumen of a non-tip area other than the tip of the insertion member;

a state specifying unit that, by using the non-tip area movement information acquired by the non-tip area movement information acquiring unit and the tip movement information acquired by the tip movement information acquiring unit, (a) specifies as a first tip stop state for vibrating the insertion member, a case where the non-tip area of the insertion member is moved and the tip of the insertion member is not moved, and (b) specifies as a second tip stop state for vibrating the insertion member more greatly than in the first tip stop state of (a), a case where the non-tip area of the insertion member is not moved and the tip of the insertion member is not moved;

an operation information generating unit that generates operation information about the insertion apparatus to execute the first tip stop state of (a) or the second tip stop state of (b) which is specified by the state specifying unit; and a control unit that controls an operation of the insertion member based on the operation information generated by the operation information generating unit.

According to the 1st aspect, a vibration magnitude is adjusted for vibration control depending on the state of the insertion member to carry out vibration control when the insertion member causes getting-stuck in a work for inserting the insertion member. Consequently, it is possible to remove the getting-stuck with a vibration having such a proper magnitude as not to cause an overload. Thus, it is possible to achieve the inserting work.

2nd aspect: The control apparatus of an insertion apparatus according to the 1st aspect, wherein the state specifying unit specifies the first tip stop state of (a) and the second tip stop state of (b) by using the non-tip area movement information acquired by the non-tip area movement information acquiring unit and the tip movement information acquired by the tip movement information acquiring unit, and specifies as a state in which the insertion member is not vibrated, a case where the tip of the insertion member is moved regardless of the presence of the moving operation in the non-tip area of the insertion member, and the operation information generating unit generates operation information about the insertion apparatus for executing any of the states specified by the state specifying unit.

According to the 2nd aspect of the present disclosure, the vibration is not carried out if the tip is moved. When the tip is inserted without the getting-stuck, therefore, a load is prevented from being applied to the body lumen.

3rd aspect: The control apparatus of an insertion apparatus according to the 1st aspect, wherein the state specifying unit specifies the first tip stop state of (a) and the second tip stop state of (b) by using the non-tip area movement information acquired by the non-tip area movement information acquiring unit and the tip movement information acquired by the tip movement information acquiring unit, and (c) specifies as a state in which the insertion member is vibrated more slightly than in the first tip stop state of (a), a case where the non-tip area of the insertion member is moved and the tip of the insertion member is moved, and the operation information generating unit generates the operation information about the insertion apparatus for executing any of the states (a) to (c) specified by the state specifying unit.

According to the 3rd aspect of the present disclosure, the vibration is carried out if the non-tip area of the insertion member is moved and the tip is moved. Therefore, it is possible to smoothly carry out the insertion.

4th aspect: The control apparatus of an insertion apparatus according to the 3rd aspect, wherein the state specifying unit specifies the first tip stop state of (a), the second tip stop state of (b), and the state of (c) by using the non-tip area movement information acquired by the non-tip area movement information acquiring unit and the tip movement information acquired by the tip movement information acquiring unit, and (d) specifies as a second tip area movement state in which the insertion member is not vibrated, a case where the non-tip area of the insertion member is not moved and the tip of the insertion member is moved, and the operation information generating unit generates the operation information about the insertion apparatus for executing any of the states (a) to (d) specified by the state specifying unit.

According to the 4th aspect of the present disclosure, the states are divided into four depending on the presence of the movement of the tip area and the presence of the movement of the non-tip area in the insertion member, and the vibration is varied every state. Consequently, it is possible to reduce the load to be applied to the body lumen.

5th aspect: The control apparatus of an insertion apparatus according to the 1st aspect, wherein the operation information generating unit generates the operation information about the insertion apparatus in which a vibration of the insertion member is in an insertion direction of the insertion member and/or a rotation direction around the insertion direction of the insertion member in a case where the state specified by the state specifying unit is the first tip stop state of (a) or the second tip stop state of (b).

According to the 5th aspect of the present disclosure, the vibration direction is limited to the insertion direction and the rotation direction. Therefore, it is possible to properly apply the vibration to the body lumen. Thus, it is possible to efficiently remove getting-stuck.

6th aspect: The control apparatus of an insertion apparatus according to any one of the 1st to 5th aspects, wherein the operation information generating unit generates the operation information about the insertion apparatus such that a vibration in the second tip stop state of (b) has a vibration amplitude, a vibration cycle, or an advance ratio increased than a vibration in the first tip stop state of (a).

According to the 6th aspect of the present disclosure, the vibration method is limited. Consequently, it is possible to efficiently remove getting-stuck.

7th aspect: The control apparatus of an insertion apparatus according to the 1st aspect, wherein the state specifying unit specifies the first tip stop state of (a) and the second tip stop state of (b) by using the non-tip area movement information acquired by the non-tip area movement information acquiring unit and the tip movement information acquired by the tip movement information acquiring unit, and (o) specifies as a first tip area movement state in which the insertion member is not vibrated, a case where the non-tip area of the insertion member is moved and the tip of the insertion member is moved, and the operation information generating unit generates the operation information about the insertion apparatus for executing the first tip stop state of (a), the second tip stop state of (b), or the first tip movement state of (o) which is specified by the state specifying unit.

According to the 7th aspect of the present disclosure, the states are divided into three depending on the presence of the movement of the tip area and the presence of the movement of the non-tip area in the insertion member, and the vibration is varied every state. Consequently, it is possible to reduce the load to be applied to the body lumen.

8th aspect: The control apparatus of an insertion apparatus according to the 7th aspect, further comprising:

a state transition storage unit that generates state transition information in which the non-tip area movement information and the tip movement information acquired by the state specifying unit are arranged in time-series order and stores the generated state transition information, wherein when generating the state transition information, the state transition storage unit (A) adds the non-tip area movement information and the tip movement information acquired by the state specifying unit to the state transition information in a case where a state acquired by the state specifying unit is different from a state acquired by the state specifying unit immediately before, and (B) does not add the non-tip area movement information and the tip movement information acquired by the state specifying unit to the state transition information in a case where the state acquired by the state specifying unit is identical to the state acquired by the state specifying unit immediately before, and the state specifying unit uses the non-tip area movement information acquired by the non-tip area movement information acquiring unit, the tip movement information acquired by the tip movement information acquiring unit, and the state transition information acquired by the state transition storage unit to (e) specifies as a state in which the insertion member is vibrated, a case where a newest state in the state transition information is the first tip stop state of (a) and a last state in the state transition information is the first tip area movement state of (o), (f) specifies as a state in which the insertion member is vibrated more greatly than in the state of (e), a case where the newest state in the state transition information is the first tip stop state of (a) and the last state in the state transition information is not the first tip area movement state of (o), (g) specifies as a state in which the insertion member is vibrated more greatly than in the state of (f), a case where the newest state in the state transition information is the second tip stop state of (b), the last state in the state transition information is the first tip stop state of (a), and a second previous state is the first tip area movement state of (o), and (h) specifies as a state in which the insertion member is vibrated more greatly than in the state of (g), a case where the newest state in the state transition information is the second tip stop state of (b), the last state in the state transition information is the first tip stop state of (a), and the second previous state is not the first tip area movement state of (o), and the operation information generating unit generates the operation information about the insertion apparatus for executing any of the states of (e) to (h) specified by the state specifying unit.

According to the 8th aspect of the present disclosure, the state transition information is generated and the magnitude of the vibration is varied depending on the state transition information. Therefore, it is possible to efficiently carry out the insertion in such a vibration magnitude as not to apply a load to the body lumen.

9th aspect: The control apparatus of an insertion apparatus according to the 8th aspect, wherein the state specifying unit (c) specifies as a state in which the insertion member is vibrated more slightly than in the first tip stop state of (a), a case where the non-tip area of the insertion member is moved and the tip of the insertion member is moved, by using the non-tip area movement information acquired by the non-tip area movement information acquiring unit and the tip movement information acquired by the tip movement information acquiring unit and the state specifying unit specifies the states of (e) to (h) by using the non-tip area movement information acquired by the non-tip area movement information acquiring unit, the tip movement information acquired by the tip movement information acquiring unit, and the state transition information acquired from the state transition storage unit, and (i) specifies a state in which the insertion member is vibrated more slightly than in the first tip stop state of (a) in a case where the newest state in the state transition information is the state of (c), (j) specifies a state in which the insertion member is vibrated more greatly than in the state of (h) in a case where the newest state in the state transition information is the second tip stop state of (b) and the last state in the state transition information is not the first tip stop state of (a), and (k) specifies a state in which the insertion member is not vibrated in a case where the newest state in the state transition information is the second tip area movement state of (d), and the operation information generating unit generates the operation information about the insertion apparatus for executing any of the states of (e) to (k) specified by the state specifying unit.

According to the 9th aspect of the present disclosure, in addition to the eighth aspect, the state transition is divided finely to change the vibration. Therefore, it is possible to carry out the insertion more efficiently.

12th aspect: The control apparatus of an insertion apparatus according to the 1st aspect, further comprising:

an insertion distance information acquiring unit that acquires insertion distance information indicative of a moving distance of the tip of the insertion member in the body lumen; and an additional vibration information generating unit that generates additional vibration information to increase a magnitude of a vibration with a longer insertion distance based on the insertion distance information acquired by the insertion distance information acquiring unit, wherein the operation information generating unit adds the additional vibration information acquired by the additional vibration information generating unit to information about a vibration to execute the first tip stop state of (a) or the second tip stop state of (b) which is specified by the state specifying unit, thereby generating operation information.

13th aspect: The control apparatus of an insertion apparatus according to the 12th aspect, wherein the additional vibration information generating unit generates the additional vibration information in a case where the insertion distance information acquired by the insertion distance information acquiring unit is more than a first threshold and is less than a second threshold which is greater than the first threshold.

According to the 12th and 13th aspects of the present disclosure, the vibration magnitude is varied depending on the insertion distance in a work for inserting the insertion member. Consequently, it is possible to accurately transmit a vibration to the tip part of the insertion member. Thus, it is possible to remove the getting-stuck of the tip part of the insertion member in the body lumen.

14th aspect: The control apparatus of an insertion apparatus according to the 1th aspect, further comprising:

an insertion distance information acquiring unit that acquires insertion distance information indicative of a moving distance of the tip of the insertion member in the body lumen;

an additional vibration information generating unit that generates additional vibration information to change a magnitude of a vibration based on the insertion distance information acquired by the insertion distance information acquiring unit; and an insertion position estimating unit that estimates a position of the tip of the insertion member with respect to the body lumen based on the insertion distance information acquired by the insertion distance information acquiring unit and generates the additional vibration information depending on the position of the tip of the insertion member with respect to the body lumen, thereby outputting the additional vibration information to the additional vibration information generating unit, wherein the additional vibration information generating unit outputs, to the operation information generating unit, the additional vibration information acquired by the insertion position estimating unit.

According to the 14th and fifteenth aspects of the present disclosure, the vibration magnitude is varied depending on an inserting position of a patient's body in the work for inserting the insertion member. Consequently, it is possible to vary the vibration magnitude for every patient or region. As a result, it is possible to carry out an accurate inserting work with a small load.

15th aspect: The control apparatus of an insertion apparatus according to the 14th aspect, wherein the insertion position estimating unit generates additional vibration information to reduce a magnitude of a vibration with a longer insertion distance based on the insertion distance information acquired by the insertion distance information acquiring unit.

16th aspect: An insertion apparatus comprising the control apparatus of an insertion apparatus according to any one of the 1st to 15th aspects.

According to the 16th aspect of the present disclosure, the vibration magnitude is adjusted depending on the state of the insertion member to perform vibration control in the case in which the insertion member causes getting-stuck in the work for inserting the insertion member. Consequently, it is possible to remove the getting-stuck with a vibration having such a proper magnitude as not to cause an overload. Thus, it is possible to achieve the inserting work.

17th aspect: A method of controlling an insertion apparatus that inserts an insertion member of a catheter or an endoscope into a body lumen, the method comprising:

acquiring tip movement information indicative of presence of movement in the body lumen of a tip of the insertion member by a tip movement information acquiring unit;

acquiring non-tip area movement information indicative of presence of a moving operation in the body lumen of a non-tip area other than the tip of the insertion member by a non-tip area movement information acquiring unit;

by a state specifying unit by using the non-tip area movement information acquired by the non-tip area movement information acquiring unit and the tip movement information acquired by the tip movement information acquiring unit, (a) specifying as a first tip stop state for vibrating the insertion member, a case where the non-tip area of the insertion member is moved and the tip of the insertion member is not moved, and (b) specifying as a second tip stop state for vibrating the insertion member more greatly than in the first tip stop state of (a), a case where the non-tip area of the insertion member is not moved and the tip of the insertion member is not moved;

generating operation information about the insertion apparatus to execute the first tip stop state of (a) or the second tip stop state of (b) which is specified by the state specifying unit, by an operation information generating unit; and controlling an operation of the insertion member based on the operation information generated by the operation information generating unit, by a control unit.

According to the 17th aspect of the present disclosure, a vibration magnitude is adjusted for vibration control depending on the state of the insertion member to carry out vibration control when the insertion member causes getting-stuck in a work for inserting the insertion member. Consequently, it is possible to remove the getting-stuck with a vibration having such a proper magnitude as not to cause an overload. Thus, it is possible to achieve the inserting work.

18th aspect: A control program for a control apparatus of an insertion apparatus that inserts an insertion member of a catheter or an endoscope into a body lumen, the program for causing a computer to function as:

a tip movement information acquiring unit that acquires tip movement information indicative of presence of movement in the body lumen of a tip of the insertion member;

a non-tip area movement information acquiring unit that acquires non-tip area movement information indicative of presence of a moving operation in the body lumen of a non-tip area other than the tip of the insertion member;

a state specifying unit that, by using the non-tip area movement information acquired by the non-tip area movement information acquiring unit and the tip movement information acquired by the tip movement information acquiring unit, (a) specifies as a first tip stop state for vibrating the insertion member, a case where the non-tip area of the insertion member is moved and the tip of the insertion member is not moved, and (b) specifies as a second tip stop state for vibrating the insertion member more greatly than in the first tip stop state of (a), a case where the non-tip area of the insertion member is not moved and the tip of the insertion member is not moved;

an operation information generating unit that generates operation information about the insertion apparatus to execute the first tip stop state of (a) or the second tip stop state of (b) which is specified by the state specifying unit; and a control unit that controls an operation of the insertion member based on the operation information generated by the operation information generating unit.

According to the 18th aspect of the present disclosure, a vibration magnitude is adjusted for vibration control depending on the state of the insertion member to carry out vibration control when the insertion member causes getting-stuck in a work for inserting the insertion member. Consequently, it is possible to remove the getting-stuck with a vibration having such a proper magnitude as not to cause an overload. Thus, it is possible to achieve the inserting work.

19th aspect: A computer readable recording medium recording a control program for a control apparatus of an insertion apparatus that inserts an insertion member of a catheter or an endoscope into a body lumen, the program for causing a computer to function as:

a tip movement information acquiring unit that acquires tip movement information indicative of presence of movement in the body lumen of a tip of the insertion member;

a non-tip area movement information acquiring unit that acquires non-tip area movement information indicative of presence of a moving operation in the body lumen of a non-tip area other than the tip of the insertion member;

a state specifying unit that, by using the non-tip area movement information acquired by the non-tip area movement information acquiring unit and the tip movement information acquired by the tip movement information acquiring unit, (a) specifies as a first tip stop state for vibrating the insertion member, a case where the non-tip area of the insertion member is moved and the tip of the insertion member is not moved, and (b) specifies as a second tip stop state for vibrating the insertion member more greatly than in the first tip stop state of (a), a case where the non-tip area of the insertion member is not moved and the tip of the insertion member is not moved;

an operation information generating unit that generates operation information about the insertion apparatus to execute the first tip stop state of (a) or the second tip stop state of (b) which is specified by the state specifying unit; and a control unit that controls an operation of the insertion member based on the operation information generated by the operation information generating unit.

According to the 19th aspect of the present disclosure, a vibration magnitude is adjusted for vibration control depending on the state of the insertion member to carry out vibration control when the insertion member causes getting-stuck in a work for inserting the insertion member. Consequently, it is possible to remove the getting-stuck with a vibration having such a proper magnitude as not to cause an overload. Thus, it is possible to achieve the inserting work.

20th aspect: A controlling integrated electronic circuit of an insertion apparatus that inserts an insertion member of a catheter or an endoscope into a body lumen, the circuit comprising:

a tip movement information acquiring unit that acquires tip movement information indicative of presence of movement in the body lumen of a tip of the insertion member;

a non-tip area movement information acquiring unit that acquires non-tip area movement information indicative of presence of a moving operation in the body lumen of a non-tip area other than the tip of the insertion member;

a state specifying unit that, by using the non-tip area movement information acquired by the non-tip area movement information acquiring unit and the tip movement information acquired by the tip movement information acquiring unit, (a) specifies as a first tip stop state for vibrating the insertion member, a case where the non-tip area of the insertion member is moved and the tip of the insertion member is not moved, and (b) specifies as a second tip stop state for vibrating the insertion member more greatly than in the first tip stop state of (a), a case where the non-tip area of the insertion member is not moved and the tip of the insertion member is not moved;

an operation information generating unit that generates operation information about the insertion apparatus to execute the first tip stop state of (a) or the second tip stop state of (b) which is specified by the state specifying unit; and a control unit that controls an operation of the insertion member based on the operation information generated by the operation information generating unit.

According to the 20th aspect of the present disclosure, a vibration magnitude is adjusted for vibration control depending on the state of the insertion member to carry out vibration control when the insertion member causes getting-stuck in a work for inserting the insertion member. Consequently, it is possible to remove the getting-stuck with a vibration having such a proper magnitude as not to cause an overload. Thus, it is possible to achieve the inserting work.

First Embodiment

FIG. 1A is a block diagram showing a robot 101 as an example of an insertion apparatus according to a first embodiment of the present disclosure. In FIG. 1A, the robot 101 is configured from a robot arm 102 and a control apparatus 103 for the robot arm 102 as an example of a control apparatus of the insertion apparatus, and controls an operation so as to insert, into an insertion target of a body lumen 301 such as a blood vessel, an insertion member of a catheter, or an endoscope as an example of an insertion member to be held by a hand 1701 (see FIG. 8A or the like) of the robot arm 102. The insertion apparatus 101 according to the first embodiment of the present disclosure does not need to be a robot but can also be configured by an apparatus such as a roller (details will be described later).

<Explanation of Control Apparatus 103 for Robot Arm 102>

The control apparatus 103 of the robot arm 102 is configured from a control apparatus body unit 104 and a peripheral apparatus 105.

<Explanation of Control Apparatus Body Unit 104>

The control apparatus body unit 104 is configured from an insertion information acquiring unit 106, an insertion member movement information acquiring unit 107, a state specifying unit 108, an operation information generating unit 109, and a control unit 110.

The peripheral apparatus 105 is configured from an input/output IF (interface) 111 and a motor driver 112. Respective functions will be described below.

The insertion member to be inserted by the insertion apparatus 101 into an insertion target of a body lumen 301 represents a flexible target such as a catheter, a guide wire, or an endoscope. An insertion target is the body lumen 301 such as a blood vessel.

Figures 3, 4:
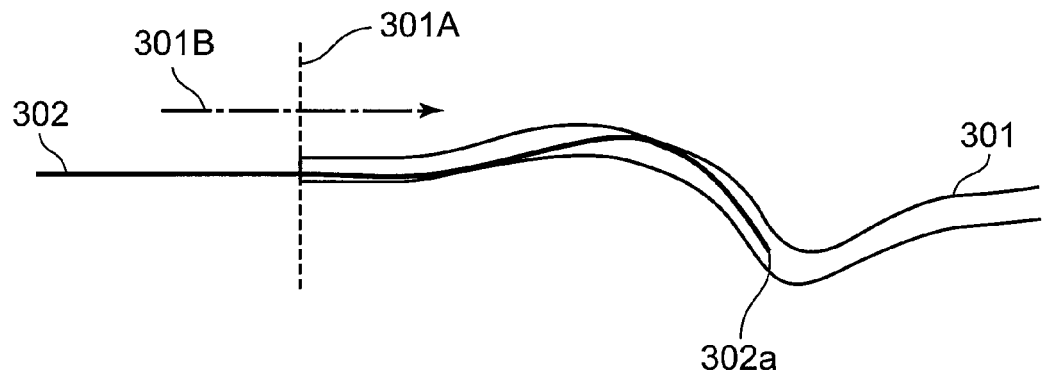
FIG. 3 is a view for explaining a method of inserting a guide wire into a blood vessel according to the first embodiment of the present disclosure.
FIG. 4 is a data diagram showing insertion information in the robot according to the first embodiment of the present disclosure.

The insertion information acquiring unit 106 functions as an example of a non-tip area movement information acquiring unit. Position and orientation information about a hand 1701 of the robot arm 102 which are acquired through the input/output IF 111 from an encoder 1715 which will be described below and time information acquired from a timer provided in the input/output IF 111 is input to the insertion information acquiring unit 106. In addition, the insertion information acquiring unit 106 differentiates the position information and the orientation information about the hand 1701 acquired from the input/output IF 111 with the time information and thus acquires velocity information and angular velocity information. FIG. 2 shows the time information, the position information, the orientation information, the velocity information, and the angular velocity information which are acquired by the insertion information acquiring unit 106. Moreover, the insertion information acquiring unit 106 generates insertion information (an example of non-tip area movement information about movement of a non-tip area other than a tip of an insertion member (for example, a holding portion of the hand 1701 to be a hand holding portion)) by using the velocity information or the angular velocity information. The insertion information is generated in the following manner. The insertion information acquiring unit 106 sets the insertion information to be 0 (which implies non-insertion) if an absolute value of the velocity information or the angular velocity information is less than a predetermined threshold (for example, 0.03 mm/ms for the velocity information and 0.003 rad/ms for the angular velocity information), and sets the insertion information to be 1 (which implies the insertion) if the absolute value of the velocity information or the angular velocity information is equal to or greater than the threshold. In that case, as information for decision with the threshold, it is possible to use any information, that is, all of the velocity information and the angular velocity information or only information about an insertion direction in the velocity information. The insertion direction represents, for example, a perpendicular direction 301B to a section 301A of an insertion port of the blood vessel 301 in an example in which a guide wire 302 of a catheter is inserted into the blood vessel 301 as shown in FIG. 3 in a work for inserting a catheter into a blood vessel, for instance. The catheter inserting work indicates a work for inserting the guide wire 302 into the blood vessel 301.

The catheter and the guide wire 302 are different from each other as follows. More specifically, the catheter is a cylindrical pipe having a hollow inner part, while the guide wire 302 is a wire to be inserted into the catheter. In the catheter inserting work, the guide wire 302 is inserted into the blood vessel 301 prior to the catheter and the catheter is then inserted into the blood vessel 301 along the guide wire 302.

A manipulator can input information to be used for a threshold or threshold decision to the insertion information acquiring unit 106 by using the input/output IF 111. FIG. 4 shows the time information to be acquired by the insertion information acquiring unit 106 and the insertion information to be generated.

The insertion information acquiring unit 106 outputs, to the state specifying unit 108, the insertion information and the time information about the robot arm 102 which are acquired. In addition, the insertion information acquiring unit 106 outputs, to the operation information generating unit 109, the position information, the orientation information, the velocity information, the angular velocity information, and the time information about the hand 1701 of the robot arm 102 which are acquired.

Although the insertion information (the non-tip area movement information) is acquired by the insertion information acquiring unit 106 based on the position information and the orientation information about the hand 1701 of the robot arm 102 in the above explanation, the insertion information (the non-tip area movement information) can also be acquired by an insertion information acquiring unit 106 based on an image acquired by an X-ray image pickup apparatus 601 which will be described below. In this case, the insertion information acquiring unit 106 extracts any one feature point in a non-tip area, detects presence of movement of the feature point, and thus acquires insertion information.

Figure 5A:
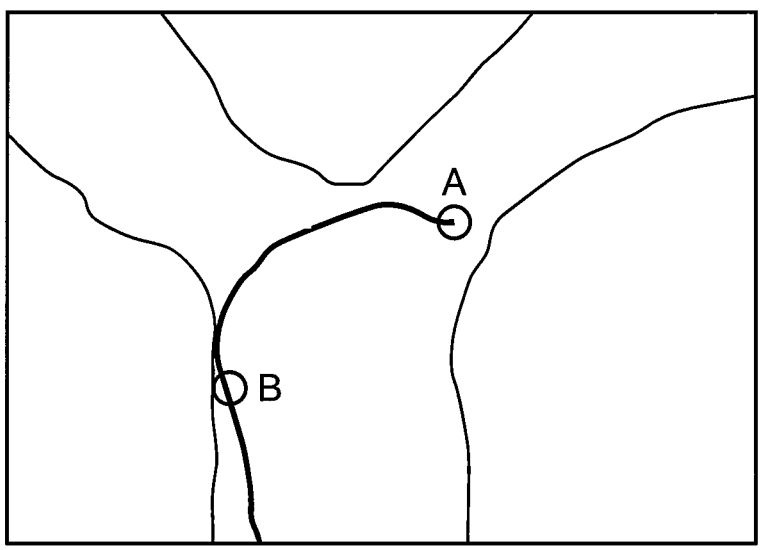
FIG. 5A is a view for explaining a method of acquiring an insertion state in the robot according to the first embodiment of the present disclosure.
Figure 5B:
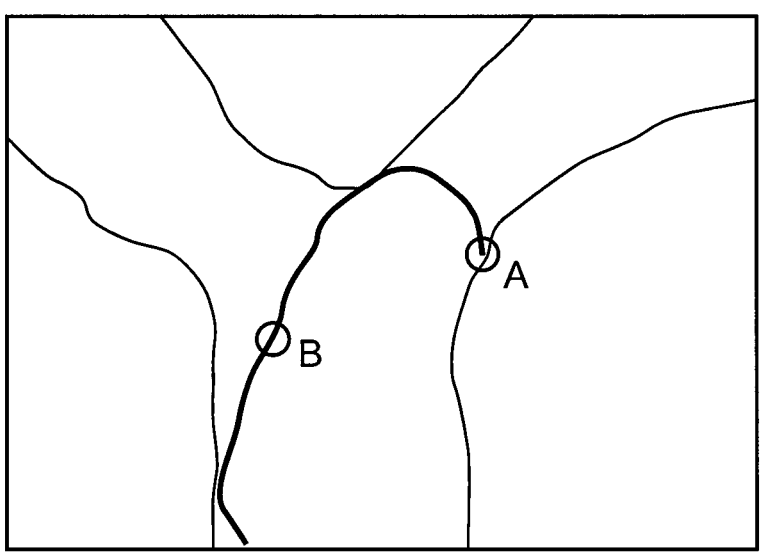
FIG. 5B is a view for explaining the method of acquiring an insertion state in the robot according to the first embodiment of the present disclosure.

A method of acquiring movement information through a pickup image will be described below (with the insertion member movement information acquiring unit 107). FIGS. 5A and 5B show the pickup image. There is shown a movement state from FIG. 5A to FIG. 5B, and the movement is distinguished depending on the feature point at this time (a dotted line or marks formed in an axial direction of the guide wire 302, for example). In the drawings, a feature point represented by the symbol A indicates the movement of the tip of the insertion member and the symbol B indicates the movement of the insertion information. In the case of the guide wire 302, a part having high flexibility in the tip can be set as the tip and a part having low flexibility in the tip can indicate the movement of the insertion information.

The insertion member movement information acquiring unit 107 functions as an example of a tip movement information acquiring unit and acquires insertion member movement information (tip movement information) about the tip of the insertion member from the input/output IF 111. A method of acquiring the movement information about the tip of the insertion member includes various methods, for example, a method of carrying out measurement by attaching a position sensor, an ultrasonic vibrator, a magnetic field generation source, or the like to the tip of the insertion member, a method of measuring the position of the tip of the insertion member by using an image pickup apparatus, and the like. Herein, the method of carrying out the measurement by means of the image pickup apparatus will be described with the catheter inserting work used as an example.

Figure 6:
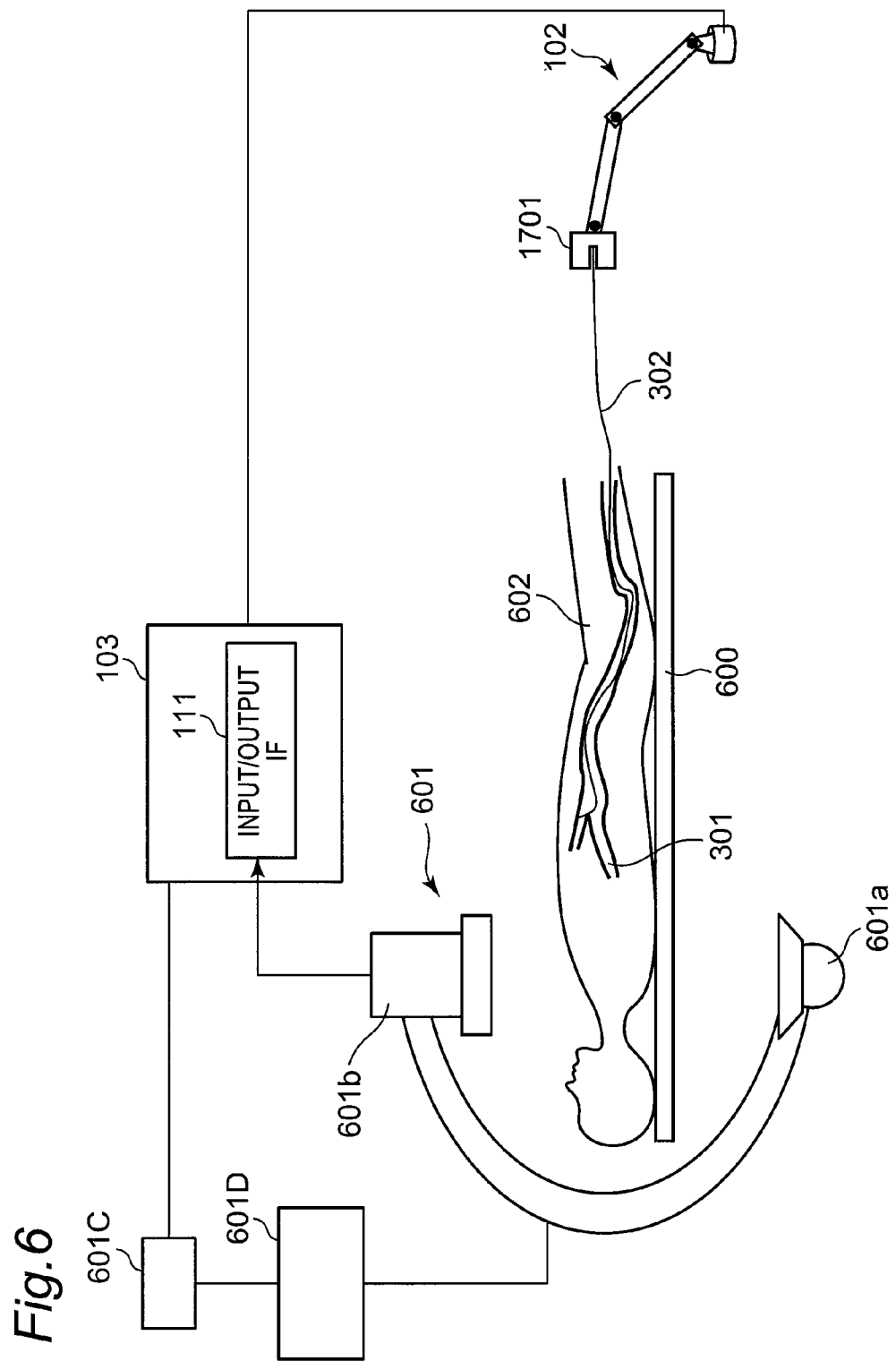
FIG. 6 is a view for explaining a method of acquiring an image through an X-ray image pickup apparatus in the robot according to the first embodiment of the present disclosure.

FIG. 6 shows a situation in which the tip of the guide wire 302 is photographed by using the X-ray image pickup apparatus 601 as an example of the image pickup apparatus in the catheter inserting work. The X-ray image pickup apparatus 601 has an X-ray generating unit 601a and an X-ray detecting unit 601b disposed to interpose a photographing target region of a patient 602 from top and bottom. The X-ray detecting unit 601b serves to detect X-rays generated from the X-ray generating unit 601a. The X-ray generating unit 601a is connected to the X-ray detecting unit 601b. The photographing target region of the patient 602 on a bed 600 is irradiated with radioactive rays (for example, X-rays) from the X-ray generating unit 601a, and the X-ray detecting unit 601b detects an X-ray image transmitted through the patient 602. A pickup image detected at this time is output from the X-ray image pickup apparatus 601 to the insertion member movement information acquiring unit 107 through the input/output IF 111. The insertion member movement information acquiring unit 107 decides whether the tip of the insertion member is moved or stopped based on the image acquired through the detection. In this case, it is also possible to provide a moving apparatus 601D configured to move the X-ray image pickup apparatus 601 and a movement control unit 601C thereof with the movement of the guide wire 302. The movement control unit 601C controls the moving apparatus 601D based on information about the movement of the guide wire 302 which is acquired from the control apparatus 103 for the robot arm 102. By such a structure, for example, a desirable part such as a tip 302a of the guide wire 302 or a vicinity of the tip 302a can be set to be the photographing target region.

Description will be given to a method of deciding the movement of the tip of the insertion member in the insertion member movement information acquiring unit 107. In the insertion member movement information acquiring unit 107, a feature is extracted (for example, a side edge is extracted) from the pickup image acquired from the input/output IF 111 to recognize the tip position of the insertion member. The recognized tip position is compared by the insertion member movement information acquiring unit 107 every certain time (for example, every 1 ms), and the insertion member movement information acquiring unit 107 decides that movement is carried out if a change in the recognized tip position is equal to or greater than a threshold (for example, 0.03 mm) and decides that the movement is not carried out if the change in the recognized tip position is smaller than the threshold.

The insertion member movement information acquiring unit 107 sets the insertion member movement information to be 1 if the tip of the insertion member is moved, and sets the insertion member movement information to be 0 if the tip of the insertion member is not moved (is stopped). The case in which the insertion member movement information is 1 is referred to as a dynamic friction state, and the case in which the insertion member movement information is 0 is referred to as a static friction state. FIG. 7 shows the time information to be acquired by the insertion member movement information acquiring unit 107 and the insertion member movement information to be generated. The insertion member movement information is stored in a built-in storage unit of the insertion member movement information acquiring unit 107.

The insertion member movement information acquiring unit 107 outputs the insertion member movement information and the time information to the state specifying unit 108.

The state specifying unit 108 acquires the insertion information and the time information from the insertion information acquiring unit 106, acquires the insertion member movement information and the time information from the insertion member movement information acquiring unit 107, and specifies whether vibration control is to be carried out or not based on the acquired information, and furthermore, specifies the magnitude of a vibration when it is specified that the vibration control is to be carried out. The "vibration control" indicates that the tip hand of the robot arm 102 is controlled to be vibrated in order to remove the getting-stuck of the insertion member (details will be described later).

In the insertion work to be carried out by the robot arm 102, four states in total are present in combination of the insertion information of 1 (a state in which the hand tip of the robot arm 102 is moving) or the insertion information of 0 (a state in which the hand tip of the robot arm 102 is stopped) and the insertion member movement information of 1 (the tip of the insertion member is in the dynamic friction state) or the insertion member movement information of 0 (the tip of the insertion member is in the static friction state). The respective states will be described below with reference to FIGS. 8A to 8E. FIGS. 8A to 8E illustrate a work for, while holding the guide wire 302 by the hand 1701 on the hand tip of the robot arm 102 (see FIG. 17A and details will be described later), inserting the guide wire 302 into the blood vessel 301.

Figure 8C:
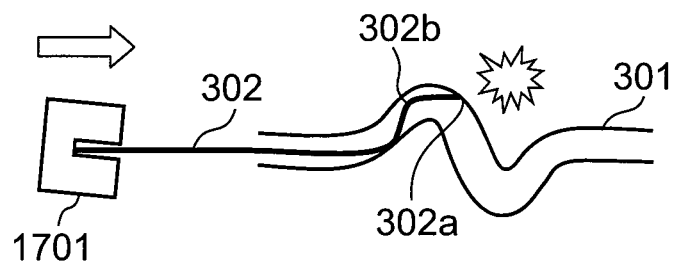
FIG. 8C is an explanatory view representing a state in the robot according to the first embodiment of the present disclosure.

FIG. 8A shows the state which is brought before the states in FIGS. 8B to 8E and in which the work for inserting the guide wire 302 into the blood vessel 301 by the robot arm 102 is started. The guide wire 302 held by the hand 1701 is inserted into the blood vessel 301 in a direction of an arrow together with the hand 1701 of the robot arm 102.

FIG. 8B shows a state following FIG. 8A and represents the state in which the insertion information is 1 and the insertion member movement information is 1. In other words, in this state, the hand 1701 of the robot arm 102 is moved in the insertion direction and the guide wire 302 is also moved. This state is referred to as a "first progress" state (a first tip area movement state). In the "first progress" state, the hand 1701 is moved in the insertion direction and the guide wire 302 is inserted along the blood vessel 301. In some cases, there is carried out the work for inserting the guide wire 302 into the blood vessel 301 with the guide wire 302 flexed in the blood vessel 301. Although the movement of the hand 1701 and the movement of the guide wire 302 are described in the explanation of four states including the "first progress" by the combination of the insertion information and the insertion member movement information, this is only illustrative and the movement of the tip 302a of the guide wire 302 may be used in place of the movement of the guide wire 302 and the movement of a portion other than the tip of the guide wire 302 (a non-tip area) (for example, a hand holding portion held by the hand 1701 or the like) may be used in place of the movement of the hand 1701.

FIG. 8C shows the state following FIG. 8A, and represents the state in which the insertion information is 1 and the insertion member movement information is 0 unlike the state in FIG. 8B. In other words, in this state, the hand 1701 of the robot arm 102 is moved in the insertion direction and the guide wire 302 is not moved. This state is referred to as a "first stop" state (a first tip stop state). In the "first stop" state, the tip 302a or a tip vicinal portion 302b of the guide wire 302 is pressed against the blood vessel 301 and the guide wire 302 is flexed in the blood vessel 301. Therefore, the guide wire 302 is not moved but stopped in the blood vessel 301.

Figure 8D:
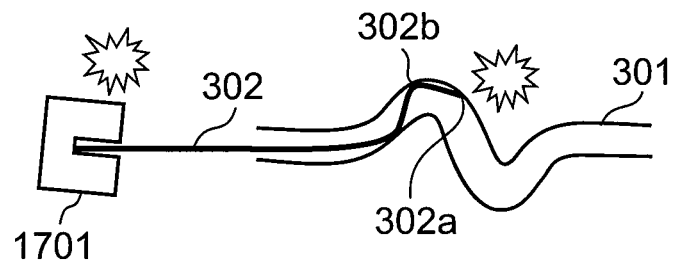
FIG. 8D is an explanatory view representing a state in the robot according to the first embodiment of the present disclosure.

FIG. 8D shows the state following FIG. 8A, and represents a state in which the insertion information is 0 and the insertion member movement information is 0 unlike the states in FIGS. 8B and 8C. In other words, in this state, the hand 1701 of the robot arm 102 is not moved in the insertion direction and the guide wire 302 is not moved. This state is referred to as a "second stop" state (a second tip stop state). In the "second stop" state, the tip 302a or the tip vicinal portion 302b of the guide wire 302 is pressed against the blood vessel 301 so that the guide wire 302 is completely flexed in the blood vessel 301 and the guide wire 302 does not advance. For this reason, the hand 1701 cannot be moved in the insertion direction.

Figure 8E:
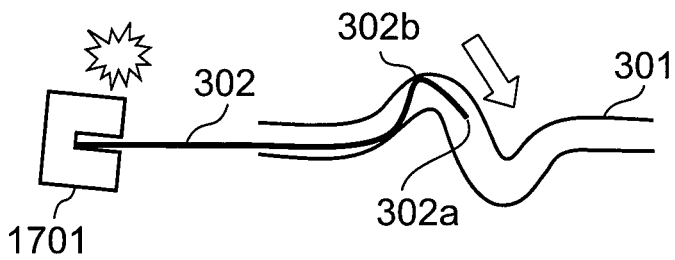
FIG. 8E is an explanatory view representing a state in the robot according to the first embodiment of the present disclosure.

FIG. 8E shows the state following FIG. 8A, and represents a state in which the insertion information is 0 and the insertion member movement information is 1 unlike the states in FIGS. 8B to 8D. In other words, in this state, the hand 1701 of the robot arm 102 is not moved in the insertion direction and the guide wire 302 is moved in the blood vessel 301. This state is referred to as a "second progress" state (a second tip area movement state). In the "second progress" state, a middle portion 302c of the guide wire 302 is pressed against the blood vessel 301 so that the hand 1701 cannot be moved in the insertion direction and only the tip 302a or the tip vicinal portion 302b of the guide wire 302 is moved.

With reference to a flowchart of FIG. 9, description will be given to a procedure for the state specifying unit 108 to specify whether the vibration control is to be carried out or not based on the insertion information and the time information about the robot arm 102 of the insertion information acquiring unit 106 and the insertion member movement information and the time information about the insertion member movement information acquiring unit 107 and to specify the magnitude of a vibration when specifying that the vibration control is to be carried out.

First of all, in step S901, the state specifying unit 108 acquires the insertion information and the time information from the insertion information acquiring unit 106 and acquires the insertion member movement information and the time information from the insertion member movement information acquiring unit 107.

In step S902, next, the specifying procedure proceeds to step S903 if the state specifying unit 108 decides that the insertion member movement information has a value of 0, and the specifying procedure proceeds to step S906 if the state specifying unit 108 decides that the insertion member movement information has a value of 1. In other words, the state specifying unit 108 specifies that the vibration control is to be carried out if the tip of the guide wire 302 is in a static friction state, and specifies that the vibration control is not to be carried out if the tip of the guide wire 302 is in a dynamic friction state.

In step S903, the specifying procedure proceeds to step S904 if the state specifying unit 108 decides that the insertion information has a value of 0, and the specifying procedure proceeds to step S905 if the state specifying unit 108 decides that the insertion information has a value of 1.

In step S904, the state specifying unit 108 specifies that the vibration control is to be carried out and specifies the magnitude of a vibration. At this time, the magnitude of the vibration has a predetermined value for a state in which the hand tip of the robot arm 102 is stopped (a first vibration state V1 of FIG. 9), and the serial processing is ended.

In step S905, the state specifying unit 108 specifies that the vibration control is to be carried out and specifies the magnitude of a vibration. At this time, the magnitude of the vibration has a predetermined value for a state in which the hand tip of the robot arm 102 is moved (a second vibration state V2 of FIG. 9), and the serial processing is ended. Herein, the state specifying unit 108 increases the magnitude of the vibration more greatly in the state in which the hand tip of the robot arm 102 is stopped (the first vibration state V1 of FIG. 9) as compared with the state in which the hand tip of the robot arm 102 is moved (the second vibration state V2 of FIG. 9).

In step S906, the state specifying unit 108 specifies that the vibration control is not to be carried out, and the serial processing is ended.

The processing of the flowchart is executed for every control cycle by the state specifying unit 108.

Next, the state information to be generated by the state specifying unit 108 will be described with reference to FIGS. 10A to 10D. FIGS. 10A to 10D sequentially correspond to the respective states described with reference to FIGS. 8B to 8E. The state information is constituted by the insertion information, the insertion member movement information, the control information, and the vibration information, and can be properly stored in an internal storage unit of the state specifying unit 108.

Figures 9, 10A, 10B:
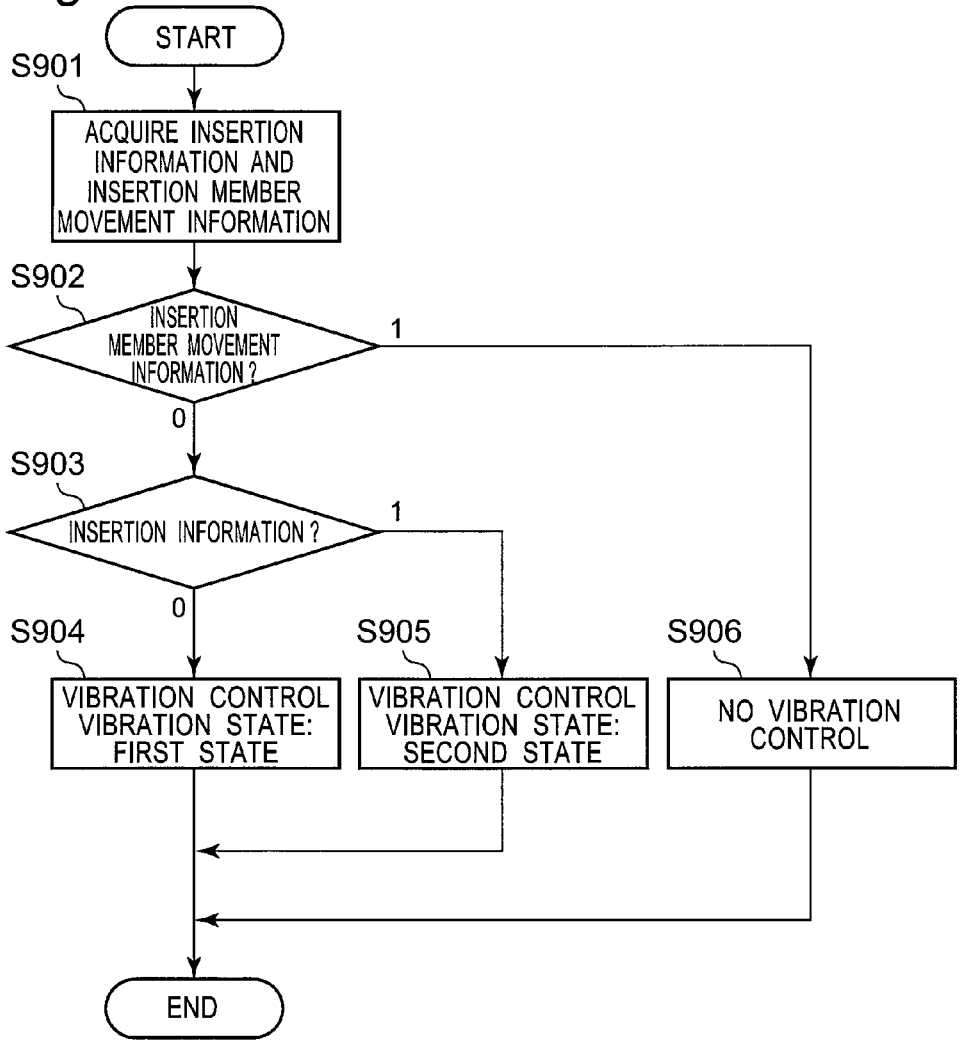
FIG. 9 is a flowchart showing a specifying method of a state specifying unit in the robot according to the first embodiment of the present disclosure.
FIG. 10A is a data diagram showing state information in the robot according to the first embodiment of the present disclosure.
FIG. 10B is a data diagram showing the state information in the robot according to the first embodiment of the present disclosure.

FIG. 10A corresponds to the "first progress" state of FIG. 8B, shows the control information to be generated by the state specifying unit 108 which is 0 because the insertion member movement information is 1, and represents to specify that the vibration control is not to be carried out. The "control information" is generated by the state specifying unit 108 and serves to specify whether the vibration control is to be carried out or not, and indicates to specify that the vibration control is to be carried out in the case of 1 and to specify that the vibration control is not to be carried out in the case of 0. Since it is specified that the vibration control is not to be carried out if the control information is 0, the vibration information is also 0. The "vibration information" represents the magnitude of a vibration in the execution of the vibration control and a greater value indicates a greater vibration.

FIG. 10B corresponds to the "first stop" state of FIG. 8C, shows the control information to be generated by the state specifying unit 108 which is 1 because the insertion member movement information is 0, and represents to specify that the vibration control is to be carried out. In addition, the vibration information is 15 and is shown to be smaller than a value of 30 in the vibration information of FIG. 10C. For instance, a vibration (repetition) motion having an amplitude of 0.06 mm is set as an example of the vibration. A manipulator can input the value to the state specifying unit 108 by using the input/output IF 111. However, it is impossible to input a greater value than the value of the vibration information in FIG. 10C.

FIG. 10C corresponds to the "second stop" state of FIG. 8D, shows the control information to be generated by the state specifying unit 108 which is 1 because the insertion member movement information is 0, and represents to specify that the vibration control is to be carried out. In addition, the vibration information is 30 and is shown to be greater than a value of 15 in the vibration information of FIG. 10B. For instance, a vibration (repetition) motion having an amplitude of 0.12 mm is set as an example of the vibration. The manipulator can input the value to the state specifying unit 108 by using the input/output IF 111. However, it is impossible to input a smaller value than the value of the vibration information in FIG. 10B.

FIG. 10D corresponds to the "second progress" state of FIG. 8E, shows the control information to be generated by the state specifying unit 108 which is 0 because the insertion member movement information is 1, and represents to specify that the vibration control is not to be carried out. If the control information is 0, it is specified that the vibration control is not to be carried out. For this reason, the vibration information is also 0.

Moreover, the manipulator can input a maximum value of the magnitude of the vibration to the state specifying unit 108 by using the input/output IF 111. For example, an amplitude of 0.3 mm is set. As an example of a method of determining a maximum value, a preliminary experiment is conducted in a simulated blood vessel in advance and a maximum amplitude which does not apply a load to the simulated blood vessel is measured to calculate the maximum value. In that case, a vibration having a greater magnitude than the maximum value is prevented from being applied.

Although control is carried out as vibration control by the control unit 110 which will be described below in order to perform the vibration to be the repetitive motion in the above description, it is also possible to adjust the strength of the movement in a certain direction.

It is also possible to vary the magnitude of the vibration depending on the region. For instance, the magnitude of the vibration is reduced in a blood vessel in a delicate part (for example, a capillary vessel) and is increased in a blood vessel in a part which is hardly damaged (for example, a femoral artery). By way of example, the vibration information depending on a region in which the tip 302a of the guide wire 302 is positioned is prestored in the internal storage unit of the state specifying unit 108. As described above, consequently, it is also possible to automatically change the vibration information depending on the region by providing the moving apparatus 601D configured to move the X-ray image pickup apparatus 601 and the movement control unit 601C thereof and thereby acquiring information about the position of the tip 302a of the guide wire 302. For example, it is also possible to reduce the magnitude of the vibration in a region in which a lesion such as arteriosclerosis is found by a previous X-ray diagnosis.

In the case in which the guide wire or the catheter is changed in the middle of the inserting work, moreover, it is also possible to vary the magnitude of the vibration depending on an individual (for example, a difference in flexibility, a difference in an outside diameter, or the like). In this case, vibration information depending each individual of the guide wire or the catheter is prestored in the internal storage unit of the state specifying unit 108. If the manipulator inputs information about the change in the individual of the guide wire or the catheter by using the input/output IF 111, consequently, it is also possible to automatically change the vibration information depending on the individual.

In the state specifying unit 108, the magnitude of the vibration is increased more greatly in the "second stop" state than in the "first stop" state. This can also be described from a result obtained by execution of the following experiment.

As shown in FIG. 11, a wire 1102 to be a simulated guide wire held by the hand 1701 was inserted into a tube 1101 to be a simulated blood vessel. The tube 1101 takes a meandering shape as shown in FIG. 11, and friction is increased with progress of the insertion so that advance is carried out with difficulty. The tube 1101 has an inside diameter of 3.0 mm and the wire 1102 has a diameter of 0.81 mm. In a state in which the vibration of the hand 1701 was controlled to vibrate the wire 1102 in the insertion direction, the wire 1102 was inserted into the tube 1101. In that case, the wire 1102 was inserted into the tube 1101 while a position at which the vibration of the wire 1102 was started was varied in the tube 1101. There was compared the magnitude of force acquired by the force sensor 1103 in the case in which a force sensor 1103 is disposed on the hand 1701 to vary the vibration start position. The magnitude of the vibration in the vibration control was set to be constant. The vibration start position was set to be two places represented by the symbols A and B in FIG. 11. The vibration start position represented by the symbol A represents the "second stop" state in which the position of the tip 1102a of the wire 1102 is stopped and the position of the hand 1701 is also stopped as shown in FIG. 12A. The vibration start position represented by the symbol B represents the "first stop" state in which the position of the tip 1102a of the wire 1102 is stopped and the position of the hand 1701 is moving as shown in FIG. 12B. FIG. 13 shows a result obtained by carrying out the insertion while controlling the vibration of the hand 1701 from the vibration start positions in these two places. In FIG. 13, the vibration start position indicates the positions represented by the symbols A and B in FIG. 11. A magnitude (N) of force indicates a value acquired by the force sensor 1103 at a time that the tip 1102a of the wire 1102 passes through the position represented by the symbol A in FIG. 12A and indicates a value acquired by the force sensor 1103 at a time that the tip 1102a of the wire 1102 passes through the position represented by the symbol B in FIG. 12B. A smaller magnitude of the force which is measured represents that the passage can be carried out by smaller force. From FIG. 13, it is apparent that the magnitude of the force is smaller in the vibration start position B than the vibration start position A. This indicates that the passage through the same position can be carried out with a smaller vibration in the start of the vibration in the "first stop" state (the start position represented by the symbol B) than in the "second stop" state (the start position represented by the symbol A).

When the state specifying unit 108 specifies that the vibration control is to be carried out, moreover, it is also possible to make a decision of the removing of getting-stuck during the vibration control, thereby adding a condition for ending the vibration control. In the case in which the vibration control is carried out in the "first stop" state or the "second stop" state so that the getting-stuck is removed and then the "first progress" state is brought, the vibration control is stopped. However, even when the vibration control is carried out in the "first stop" state or the "second stop" state, the getting-stuck may not removed in some cases. When the vibration control is continuously carried out in this case, a load to be applied to the blood vessel is increased, which is dangerous. As a countermeasure, it is possible to add a function for automatically stopping the vibration control when a certain time passes since the start of the vibration control. A manipulator can input a value of the certain time to the state specifying unit 108 by using the input/output IF 111 (for example, 5.0 s). The removal of the getting-stuck is detected by a state transition to the "first progress" state. Similarly, non-removal of the getting-stuck is detected by remaining in the "first stop" state or the "second stop" state in a predetermined time without the transition to the "first progress" state.

The state specifying unit 108 generates the state information shown in FIGS. 10A to 10D and outputs the state information together with the time information to the operation information generating unit 109.

The operation information generating unit 109 acquires the state information and the time information from the state specifying unit 108 in the automatic reproduction of the robot arm 102, determines whether the vibration control is added to the operation information or not and the magnitude of a parameter for a vibration in the addition of the vibration control based on the acquired information and on the operation information about the robot arm 102 in teaching stored in the internal storage unit of the operation information generating unit 109, generates operation information including the determined information, and outputs the generated operation information together with the time information to the control unit 110. In addition, the operation information generating unit 109 generates operation information based on the position information, the orientation information, the velocity information, the angular velocity information, and the time information about the hand 1701 of the robot arm 102 which are acquired from the insertion information acquiring unit 106 in the manipulation of the robot arm 102. Furthermore, the operation information generating unit 109 determines whether the vibration control is added to the operation information or not and the magnitude of the parameter for the vibration in the addition of the vibration control, and generates operation information including the determined information. The operation information is properly stored in the internal storage unit of the operation information generating unit 109.

Specifically, if the control information in the state information which is acquired from the state specifying unit 108 is 0, the operation information generating unit 109 outputs, to the control unit 110, the operation information which indicates not to carry out the vibration control. If the control information in the state information which is acquired from the state specifying unit 108 is 1, the operation information generating unit 109 outputs, to the control unit 110, the operation information which indicates to carry out the vibration control. In addition, if the control information is 1, the operation information generating unit 109 determines the magnitude of the vibration based on the vibration information.

A direction of the vibration can be any axial direction or rotation direction. In addition, it is also possible to carry out a vibration at the same time in a plurality of directions. Moreover, the rotation direction of the vibration can also be a normal-reverse rotation, either rotation direction, or the like. Furthermore, the vibration can be any combination of a forward-backward motion in an axial direction, a motion in the normal-reverse rotation direction, and a motion in either rotation direction. As an example, an insertion direction and a rotation direction with the insertion direction set to be a central axis will be described with reference to FIGS. 14A and 14B.

In FIG. 14A, the guide wire 302 is vibrated forward and backward to carry out a vibration in the insertion direction of the guide wire 302 into the blood vessel 301 as indicated by the symbol AA. In order to prevent an overload from acting on the blood vessel 301, at first vibration, the guide wire 302 is once moved backward and is vibrated forward and backward. As an effect for vibrating the guide wire 302 in the insertion direction, the guide wire 302 easily advances in a progress direction. In FIG. 14B, the guide wire 302 is vibrated in the rotation direction and is thus vibrated in the normal-reverse rotation direction with the insertion direction set as the central axis as indicated by the symbol AB. As an effect for carrying out the vibration in the rotation direction, a load to be applied to the blood vessel 301 is lessened and the blood vessel 301 is hard to be damaged.

Next, description will be given to a parameter to be varied in change in the magnitude of the vibration. Herein, the parameter to be varied includes at least one of an amplitude, a cycle, and an ratio of advance. FIGS. 15A to 15D illustrate a relationship between a time and a movement distance of the hand tip position of the robot arm 102 or a rotation angle of the hand tip orientation, and an axis of abscissa indicates the time and an axis of ordinate indicates the distance.

Figure 15A:
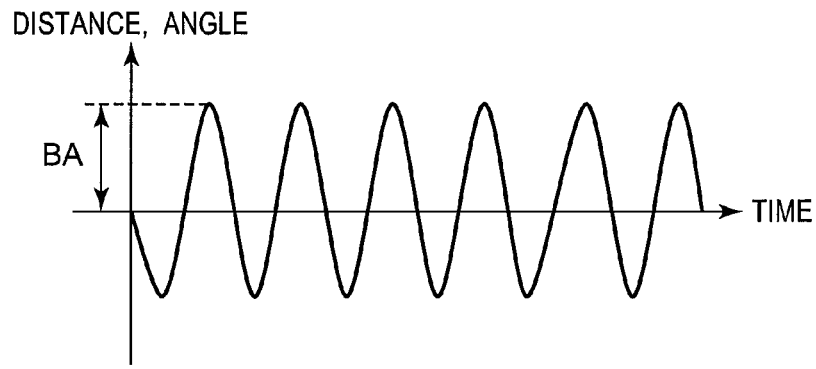
FIG. 15A is a chart for explaining the magnitude of a vibration in the robot according to the first embodiment of the present disclosure.

The amplitude represents a distance in a vibration as indicated by the symbol BA in FIG. 15A. In the case in which the magnitude of the vibration is increased, the distance to be amplitude is increased.

Figure 15B:
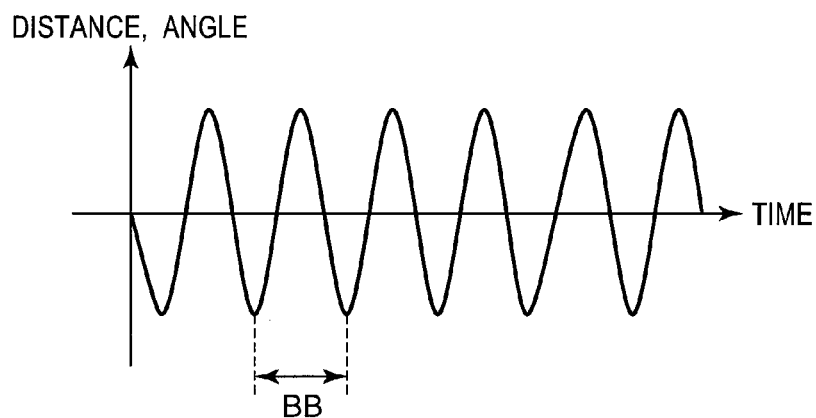
FIG. 15B is a chart for explaining the magnitude of the vibration in the robot according to the first embodiment of the present disclosure.

The cycle represents a time for 1 cycle in the vibration as indicated by the symbol BB in FIG. 15B. In the case in which the magnitude of the amplitude is increased, the time for 1 cycle to be the cycle is reduced.

Figure 15C:
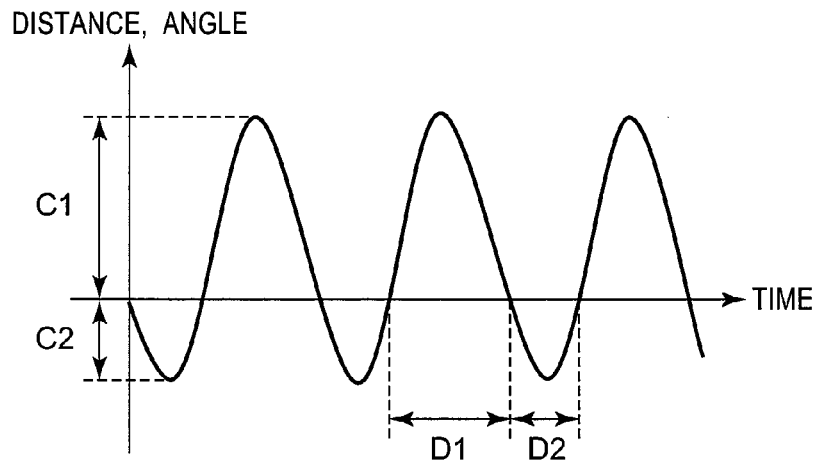
FIG. 15C is a chart for explaining the magnitude of the vibration in the robot according to the first embodiment of the present disclosure.

The ratio of advance is represented by a ratio of the amplitude and that of the time. As shown in FIG. 15C, the ratio of the amplitude represents a ratio of a distance in a positive direction (the symbol C1 in FIG. 15C) to a distance in a negative direction (the symbol C2 in FIG. 15C). It is represented that the ration of the distance in the positive direction is increased when the ratio of the amplitude is increased. The ratio of the time represents a ratio of a time in the positive direction (the symbol D1 in FIG. 15C) to a time in a negative direction (the symbol D2 in FIG. 15C) as shown in FIG. 15C. In other words, increase in the ratio of the advance represents easiness of the advance in the positive direction. For example, in the case in which the ratio of the advance is increased when the vibration is carried out in the insertion direction, the insertion distance is increased in the relationship between the time and the insertion distance as shown in FIG. 15D.

In the three parameters, the ratio of the advance, the amplitude, and the cycle are arranged in descending order of importance. As an effect for increasing the ratio of the advance, the advance is easily carried out in the insertion direction. As an effect for increasing the amplitude, the advance is easily carried out in the insertion direction following the ratio of the advance. As an effect for increasing the cycle, the load to be applied to the blood vessel 301 is lessened and the blood vessel 301 is hard to be damaged.

Referring to FIGS. 15A to 15D, although the vibration is carried out in a reward movement direction with respect to the insertion direction at time of start of the vibration (a negative direction on the axis of ordinate), it is also possible to start with the vibration in the insertion direction. As shown in FIG. 15E, it is also possible to cause the amplitude of the vibration at time of start of the vibration to be smaller than the amplitude of the vibration at the other time.

For each of the three parameters including the amplitude, the cycle, and the ratio of the advance, an effect obtained by the increase in the amplitude will be described by using the experiment shown in FIG. 11. Herein, FIGS. 16A to 16C show results obtained by varying the amplitude, the cycle, and the ratio of the advance to perform the experiment, respectively. The wire 1102 is inserted into the tube 1101 while controlling the vibration of the hand 1701. The vibration start position is set to position B. The experiment was performed with cases changed into two ways, that is, the case in which the respective parameters including the amplitude, the cycle, and the ratio of the advance are great and the case in which they are small. The experiment was started in the stop state shown in FIG. 12B. There are compared the insertion distances until the wire 1102 cannot advance due to the getting-stuck in the middle of the tube 1101. Herein, the "insertion distance" implies an inserted distance where the advance cannot be carried out due to the getting-stuck.

FIG. 16A shows the result of the experiment which is obtained by changing the amplitude. In this case, the small amplitude is 0.6 mm and the great amplitude is 3.6 mm. Both of the cycles are 60 ms, and concerning the ratio of the advance, the ratio of the positive direction to the negative direction for the amplitude is 2 to 1, and the ratio of the positive direction to the negative direction for the time is 1 to 1. From FIG. 16A, it is apparent that the insertion distance is longer in the case of the great amplitude than the case of the small amplitude.

FIG. 16B shows the result of the experiment which is obtained by changing the cycle. In this case, the fast cycle is 30 ms and the slow cycle is 120 ms. Both of the amplitudes are 1.8 mm, and concerning the ratio of the advance, the ratio of the positive direction to the negative direction for the amplitude is 2 to 1, and the ratio of the positive direction to the negative direction for the time is 1 to 1. From FIG. 16B, it is apparent that the insertion distance is longer in the case of the fast cycle than the slow cycle.

FIG. 16C shows the result of the experiment which is obtained by changing the ratio of the advance. In this case, the ratio of the amplitude is 6 to 1 and the ratio of the time is 3 to 1 when the ratio of the advance is high. The ratio of the amplitude is 12 to 1 and the ratio of the time is 6 to 1 when the ratio of the advance is low. From FIG. 16C, it is apparent that the insertion distance is longer in the case of the high ratio than the low ratio.

The manipulator can input these vibration direction or the parameters to be changed to the operation information generating unit 109 by using the input/output IF 111 and can determine the parameter by the operation information generating unit 109.

Description will be given to a method of generating operation information in the operation information generating unit 109. The method of generating operation information differs between in the automatic reproduction and in the manipulation of the robot arm 102.

The "automatic reproduction" represents that the robot arm 102 automatically reproduces a taught operation, and FIG. 17B shows an example of the automatic reproduction through the robot arm 102.

The "manipulation" represents the manipulator holds the robot arm 102 with a hand 2001 to carry out a manipulation, and FIG. 17C shows an example of the manipulation of the robot arm 102.

In the automatic reproduction of the robot arm 102, the operation information is generated by the operation information generating unit 109 based on the operation information about the robot arm 102 in the teaching which is stored in the internal storage unit of the operation information generating unit 109. In the case in which the vibration control is not carried out based on the information transmitted from the state specifying unit 108, the operation information is generated directly from the operation information in the teaching by the operation information generating unit 109. In the case in which the vibration control is carried out based on the information transmitted from the state specifying unit 108, information obtained by adding the operation information about the vibration control to the operation information in the teaching is generated as the operation information by the operation information generating unit 109.

In the manipulation of the robot arm 102, the operation information is generated by the operation information generating unit 109 based on the position information, the orientation information, the velocity information, the angular velocity information, and the time information about the hand 1701 which are input from the insertion information acquiring unit 106. In the case in which the vibration control is not carried out based on the information transmitted from the state specifying unit 108, the operation information is generated directly from the position information, the orientation information, the velocity information, the angular velocity information, and the time information about the hand 1701 which are input from the insertion information acquiring unit 106 by the operation information generating unit 109. In the case in which the vibration control is carried out based on the information transmitted from the state specifying unit 108, the operation information is generated directly from information obtained by adding the operation information about the vibration control to the position information, the orientation information, the velocity information, the angular velocity information, and the time information about the hand 1701 which are input from the insertion information acquiring unit 106.

The manipulator can select a mode of automatic reproduction (an automatic reproduction mode) and a mode of a manipulation (a manipulation mode) by using the input/output IF 111. Also in the case of a structure of a master slave apparatus, operation information to be a basis is replaced with operation information about a master robot arm so that the operation information can be generated by the same generating method. Also in the master slave apparatus, both the automatic reproduction mode and the manipulation mode are present.

The operation information generating unit 109 determines whether the vibration control is to be carried out or the magnitude of a parameter for the vibration, generates the operation information, and outputs the operation information together with the time information to the control unit 110.

The control unit 110 acquires the operation information and the time information from the operation information generating unit 109 and controls the operation of the robot arm 102 based on the acquired information. In the control unit 110, the input operation information is output to the input/output IF 111 every certain time (for example, every 1 ms) to control the operation of the robot arm 102 by utilizing a timer provided in the input/output IF 111.

<Explanation of Peripheral Apparatus>

Figure 17A:
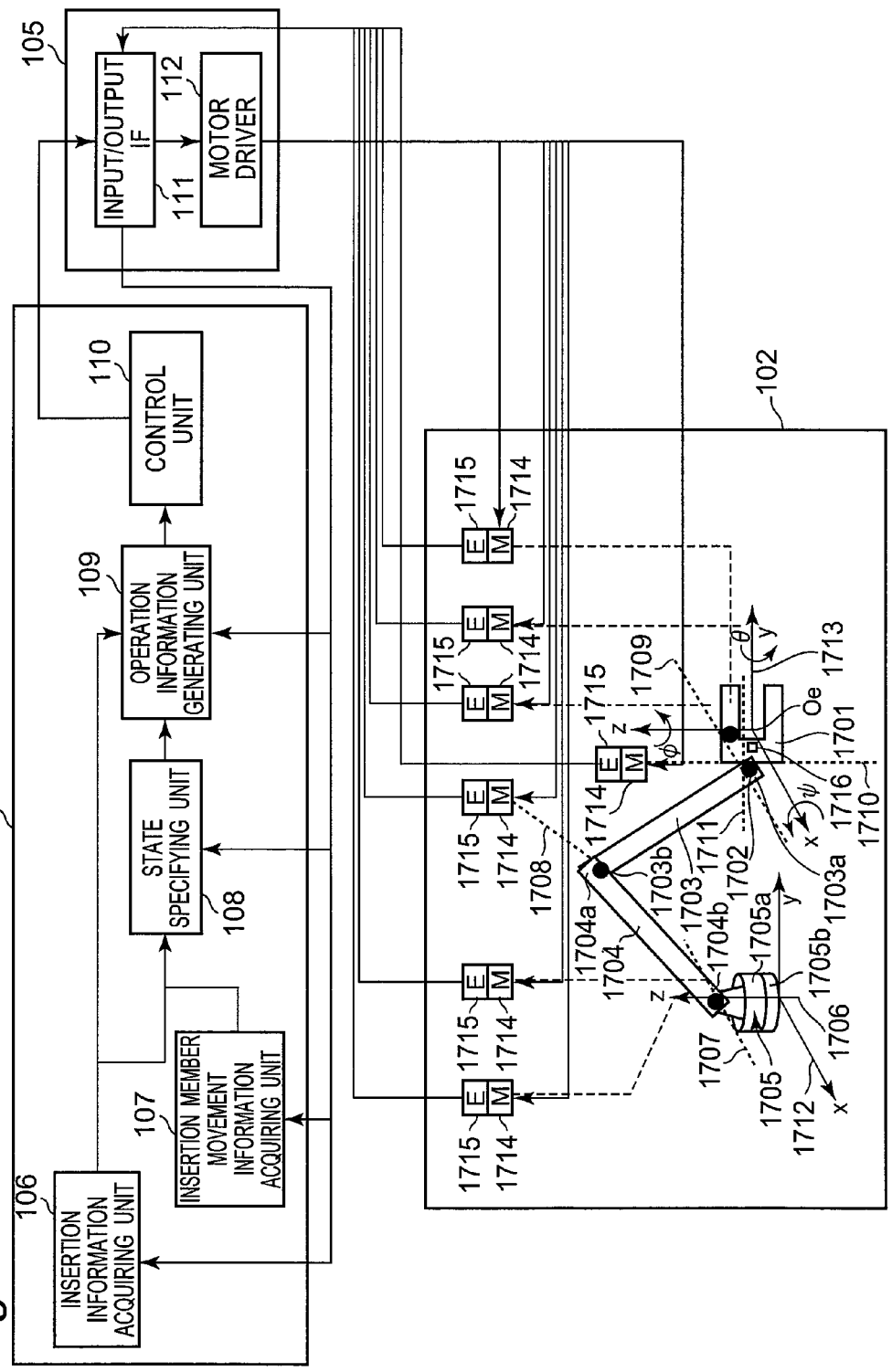
FIG. 17A is a view for explaining a robot arm and a control apparatus body unit in the robot according to the first embodiment of the present disclosure.

As shown in FIG. 17A, the input/output IF 111 outputs the operation information input from the control unit 110 to the motor driver 112. In addition, information calculated and output by a calculation unit in the encoder 1715 is input as position information and orientation information from the encoder 1715 to the input/output IF 111. The position information and the orientation information about the robot arm 102 (mainly, the hand 1701) input from the encoder 1715 to the input/output IF 111 and the time information transmitted from the timer provided in the input/output IF 111 are output from the control unit 110 to the insertion information acquiring unit 106.

Figure 1B:
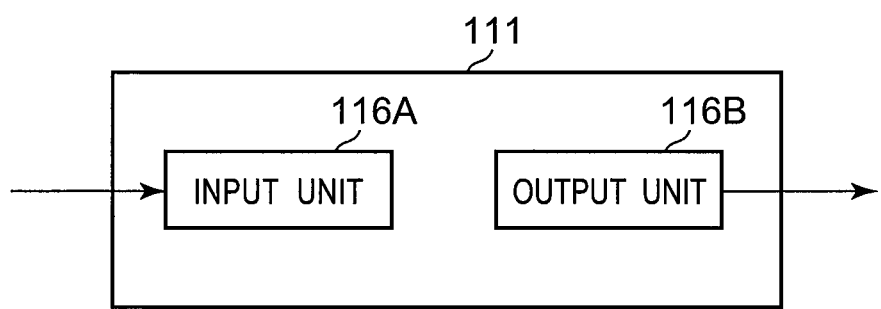
FIG. 1B is a block diagram showing an input/output IF in the robot according to the first embodiment of the present disclosure.

Moreover, the input/output IF 111 outputs a pickup image acquired from the X-ray image pickup apparatus 601 by the input/output IF 111 together with the time information to the insertion member movement information acquiring unit 107. The input/output IF 111 is configured from the input unit 116A and the output unit 116B as shown in FIG. 1B. The input unit 116A serves as an input IF (interface) and is used in the case in which the manipulator selects information to be selected by a keyboard, a mouse, a touch panel, a voice input, or the like or the case in which the manipulator inputs a numeral by the keyboard, the mouse, the touch panel, the voice input, or the like. The output unit 116B serves as an output IF (interface) and is used in the case in which the acquired information, the information to be selected, or the like is output to an outside or the case in which the information is displayed on a display or the like.

The motor driver 112 outputs, to the robot arm 102, a command value to be given to a motor 1714 in each joint part (see FIG. 17A) in the robot arm 102 in order to control the operation of the robot arm 102 based on the operation information acquired from the input/output IF 111.

<Explanation of Robot Arm>

In the robot arm 102, the timer provided in the input/output IF 111 is utilized to obtain the operation information about the robot arm 102 by the calculating unit in the encoder 1715 of the robot arm 102 and to output the operation information from the encoder 1715 to the input/output IF 111 per certain time (for example, every 1 ms). The robot arm 102 is controlled in accordance with the command values sent from the motor driver 112.

These details will be described below with reference to FIG. 17A. The robot arm 102 forms, as an example, a multilink manipulator having a freedom degree of 6 rotatably around six axes in total.

As shown in FIG. 17A, the robot arm 102 is a multijoint robot arm as an example, and specifically, a multilink manipulator having a freedom degree of 6.

The robot arm 102 includes a hand 1701, a front arm link 1703, an upper arm link 1704, and a base portion 1705. The front arm link 1703 includes, on a tip 1703a thereof, a wrist portion 1702 having the hand 1701 attached thereto. A tip 1704a of the upper arm link 1704 is rotatably coupled to a base end 1703b of the front arm link 1703. A base end 1704b of the upper arm link 1704 is rotatably coupled to and supported on the base portion 1705. Although the base portion 1705 is fixed into a certain position, the base portion 1705 may be movably coupled to a rail which is not shown.

The wrist portion 1702 has three rotation axes at which a fourth joint portion 1709, a fifth joint portion 1710, and a sixth joint portion 1711 are orthogonal to each other, and can change a relative orientation (a direction) of the hand 1701 to the front arm link 1703. In other words, in FIG. 17A, the fourth joint portion 1709 can change the relative orientation of the hand 1701 to the wrist portion 1702 around a transverse axis. The fifth joint portion 1710 can change the relative orientation of the hand 1701 to the wrist portion 1702 around a vertical axis which is orthogonal to the transverse axis of the fourth joint portion 1709. The sixth joint portion 1711 can change the relative orientation of the hand 1701 to the wrist portion 1702 around a transverse axis which is orthogonal to the transverse axis of the fourth joint portion 1709 and to the vertical axis of the fifth joint portion 1710. The base end 1703b of the front arm link 1703 can be rotated around a third joint portion 1708 with respect to the tip 1704a of the upper arm link 1704, that is, around a transverse axis which is parallel with the transverse axis of the fourth joint portion 1709. The other end of the upper arm link 1704 can be rotated around a second joint portion 1707 with respect to the base portion 1705, that is, around a transverse axis which is parallel with the transverse axis of the fourth joint portion 1709. Furthermore, an upper movable portion 1705a of the base portion 1705 can be rotated around the first joint portion 1706 with respect to a lower fixed portion 1705b of the base portion 1705, that is, around a vertical axis which is parallel with the vertical axis of the fifth joint portion 1710.

As a result, the robot arm 102 forms the multilink manipulator having the freedom degree of 6 rotatably around the six axes in total.

Each of the joint portions forming a rotation part of each axis of the robot arms 102 is provided with a rotation driving apparatus such as the motor 1714 for driving the joint portion, and the encoder 1715 configured to detect a rotation phase angle (that is, a joint angle) of the rotation shaft of the motor 1714 and to calculate the detected information in the calculating unit in the encoder 1715, thereby outputting the information as position information and orientation information (which is actually disposed in each of the joint portions of the robot arm 102). The motor 1714 (which is actually disposed in each of the joint portions of the robot arm 102) is provided on one of a pair of members forming the joint portion (for example, a rotation side member and a support side member supporting the rotation side member) and is controlled to be driven by the motor driver 112. The rotation shaft of the motor 1714 provided in the one of the members of the joint portion is coupled to the other member of the joint portion to rotate the rotation shaft normally and reversely, thereby enabling the rotation of the other member around each axis with respect to the one of the members.

In addition, reference numeral 1712 indicates an absolute coordinate system having a relative positional relationship fixed with respect to the lower fixed portion 1705b of the base portion 1705, and reference numeral 1713 indicates a hand tip coordinate system having a relative positional relationship fixed with respect to the hand 1701. An origin position $O_e$ (x, y, z) of the hand tip coordinate system 1713 seen from the absolute coordinate system 1712 is defined as the hand tip position of the robot arm 102, and ($\Phi$, $\theta$, $\phi$) representing the orientation of the hand tip coordinate system 1713 seen from the absolute coordinate system 1712 by a roll angle, a pitch angle, and a yaw angle is defined as the hand tip orientation (orientation information) of the robot arm 102, and a hand tip position and orientation vector are defined as a vector $r=[x, y, z, \Phi, \theta, \phi]^T$. As an example, accordingly, the vertical axis of the first joint portion 1706 can be positioned in parallel with a z-axis of the absolute coordinate system 1712 and the transverse axis of the second joint portion 1707 can be positioned in parallel with an x-axis of the absolute coordinate system 1712. As an example, the transverse axis of the fourth joint portion 1709 can be positioned in parallel with an x-axis of the hand tip coordinate system 1713, the transverse axis of the sixth joint portion 1711 can be positioned in parallel with a y-axis of the hand tip coordinate system 1713, and the vertical axis of the fifth joint portion 1710 can be positioned in parallel with a z-axis of the hand tip coordinate system 1713. A rotation angle with respect to the x-axis of the hand tip coordinate system 1713 is defined as the yaw angle $\phi$, a rotation angle with respect to the y-axis is defined as a pitch angle $\theta$, and a rotation angle with respect to the z-axis is defined as a roll angle $\Phi$.

Figure 18A:
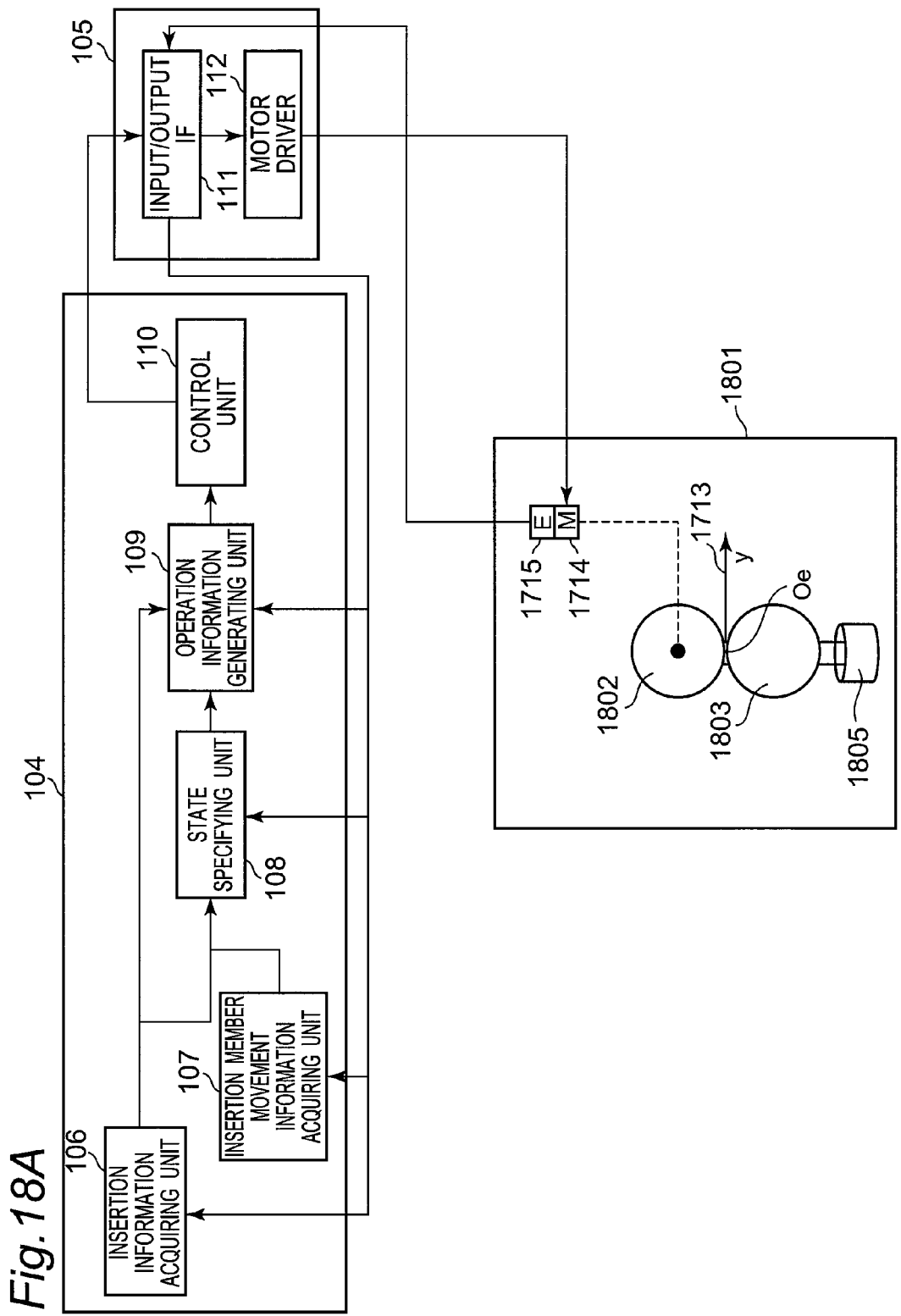
FIG. 18A is a view for explaining a 1-axial roller type feeding apparatus and a control apparatus body unit according to the first embodiment of the present disclosure.
Figure 18B:
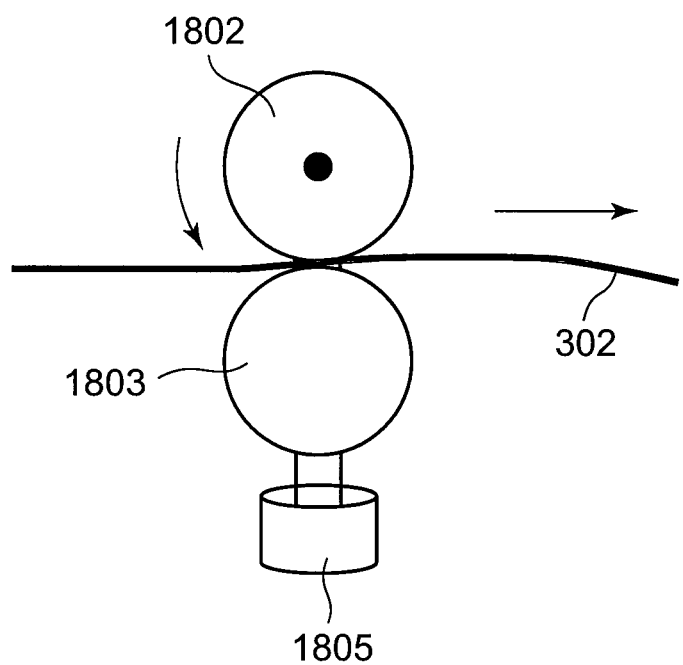
FIG. 18B is a view for explaining the 1-axial roller type feeding apparatus and the control apparatus body unit according to the first embodiment of the present disclosure.

The insertion apparatus according to the first embodiment of the present disclosure does not need to be the robot arm 102 but can also be configured in an apparatus such as a roller which will be described below. In addition, a 6-axis operation is not required but the number of the axes is arbitrary if the operation is carried out with 1 or more axes. However, the insertion apparatus needs to be operated in the insertion direction. With reference to FIGS. 18A and 18B, description will be given to a roller type feeding apparatus to be operated with 1 axis in the insertion direction and a roller type feeding apparatus to be operated with 2 axes in the insertion direction and the rotation direction with the insertion direction set as an axis as two other examples of the insertion apparatus.

FIG. 18A shows a roller type feeding apparatus 1801 to be operated with only 1 axis in the insertion direction. An insertion member such as the guide wire 302 is held by an upper roller (a first roller) 1802 and a lower roller (a second roller) 1803, and operations of the rollers 1802 and 1803 are controlled to feed the guide wire 302 (see FIG. 18B). Herein, the roller to be controlled may be the upper roller 1802 or the lower roller 1803. The roller to be controlled is provided with the motor 1714 and the encoder 1715 in the same manner as the joint portion of the robot arm 102 and is controlled by the motor driver 112 in the same manner as the case of the robot arm 102. The upper roller 1802 and the lower roller 1803 are rotatably supported on a base portion 1805.

FIG. 18C shows another roller type feeding apparatus 1801B to be operated in two-axis directions including an insertion direction and a rotation direction with the insertion direction set as a central axis. Methods of holding and feeding the insertion member are the same as those in the 1-axis type roller type feeding apparatus 1801 described with reference to FIG. 18A. Differently from the 1-axis type, a feeding unit 1806 having a third roller 1804 and configured from an upper roller 1802 and a lower roller 1803 through the third roller 1804 can be controlled to be rotated around a central axis with the insertion direction set as the central axis. A bracket 1806a is fixed to the third roller 1804, and the upper roller 1802 and the lower roller 1803 are rotatably supported on the bracket 1806a. The third roller 1804 is provided with a motor 1714 and an encoder 1715 in the same manner as the joint portion of the robot arm 102, and is controlled by the motor driver 112 in the same manner as in the case of the robot arm 102. The third roller 1804 is rotatably supported on the base portion 1805. Consequently, the operation of the insertion member can also be controlled in the rotation direction with the insertion direction set as the central axis, in addition to the insertion direction.

By using the roller type feeding apparatuses 1801 and 1801B shown in FIGS. 18A to 18C, the rollers 1802, 1803, and 1804 can usually feed the insertion member without holding again the insertion member in the same position in the case in which the insertion member to be a holding target is a very long thing. In the case of the robot arm 102, the insertion member is held by the hand 1701. When inserting the insertion member which is longer than a movable range of the robot arm 102, therefore, it is necessary to change and hold again a position in which the insertion member is to be held by the hand 1701.

The above-described respects are effects obtained by using the roller type feeding apparatuses 1801 and 1801B.

As an example of the execution of the vibration control, moreover, the hand 1701 is provided with an ultrasonic vibrator 1716 or the like, and the ultrasonic vibrator 1716 is vibrated to carry out vibration control.

Signals for turning on/off a vibration and controlling the magnitude are input from the input/output IF 111 to the ultrasonic vibrator 1716 or the like. In addition, it is also possible to add a vibration by carrying out the operation control of the robot arm 102.

<Explanation of Operation Procedure>

A procedure for inserting the insertion member through the insertion apparatus according to the first embodiment will be described for the automatic reproduction and the manipulation.

Referring to the selection of the automatic reproduction mode or the manipulation mode, a manipulator can input information about which mode is to be selected, to the operation information generating unit 109 by using the input/output IF 111.

<Explanation of Automatic Reproduction>

In the automatic reproduction, the operation of the robot arm 102 is controlled by the control unit 110 based on the operation information about the robot arm 102 in the teaching which is stored in the internal storage unit of the operation information generating unit 109. Under control of the control unit 110, the operation in the teaching is carried out by the control unit 110 in the case in which the vibration control is not performed, and an operation obtained by adding a vibration to the operation in the teaching is carried out by the control unit 110 in the case in which the vibration control is performed.

A procedure for inserting the guide wire 302 held by the hand 1701 into the blood vessel 301 through the automatic reproduction will be described with reference to respective different states in FIGS. 19A to 19D.

Figure 19A:
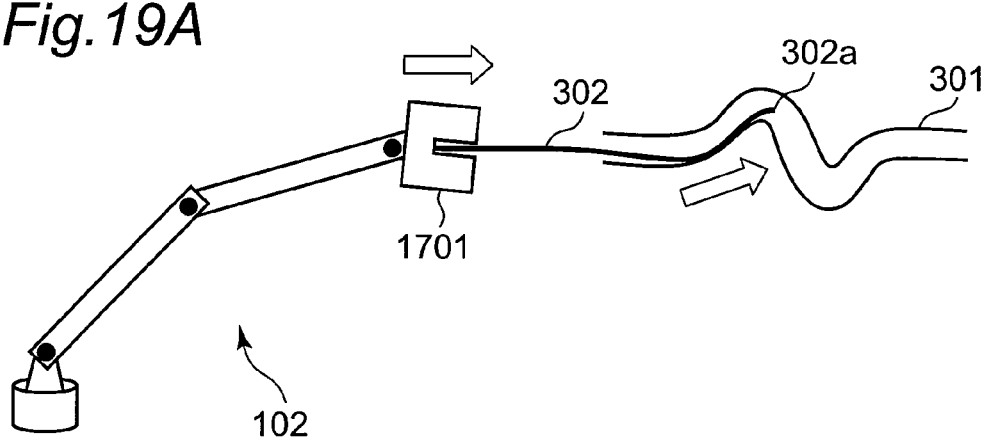
FIG. 19A is a view for explaining an operation procedure of a work for inserting a guide wire into a blood vessel (in automatic reproduction) in the robot according to the first embodiment of the present disclosure.

FIG. 19A shows a time that reproduction of teaching data is started by the control unit 110. At this time, both the insertion information and the insertion member movement information are 1, the vibration control is not carried out, and the teaching data is generated as the operation information by the operation information generating unit 109 and is reproduced by the control unit 110. In the automatic reproduction, a person turns on the vibration control mode in the state specifying unit 108 by using the input/output IF 111 at start of the reproduction in this example.

The "vibration control mode" serves to specify whether the vibration control is to be carried out or not in the state specifying unit 108. If it is decided that the vibration control mode is ON in the state specifying unit 108, the state specifying unit 108 specifies whether the vibration control is to be carried out or not. If it is decided that the vibration control mode is OFF in the state specifying unit 108, however, a mode for performing no vibration control is set. The state specifying unit 108 specifies that the vibration control is not to be carried out even when a condition for performing the vibration control is satisfied (in other words, the control information is set to be 0 and the vibration information is set to be 0 as the state information in the state specifying unit 108). In the automatic reproduction, the state specifying unit 108 decides that the vibration control mode is ON at the start of the reproduction. However, the manipulator can also input a timing for turning ON the vibration control mode to the state specifying unit 108 by using the input/output IF 111.

Figure 19B:
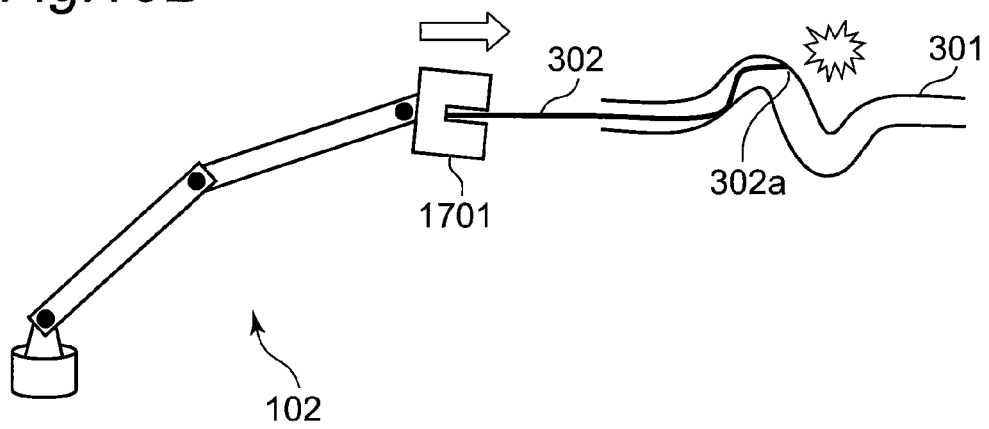
FIG. 19B is a view for explaining the operation procedure of the work for inserting the guide wire into the blood vessel (in the automatic reproduction) in the robot according to the first embodiment of the present disclosure.

Furthermore, FIG. 19B shows a time that the tip 302a of the guide wire 302 is gotten stuck in the blood vessel 301 and the movement of the tip 302a is thus stopped during the reproduction of the teaching data through the control unit 110. At this time, the insertion information is 1 and the insertion member movement information is 0, and the vibration control is started by the control unit 110. In other words, when the state information in which the insertion information is 1, the insertion member movement information is 0, and the control information is 1 is input from the state specifying unit 108 to the operation information generating unit 109, and the operation information for starting the vibration control is generated by the operation information generating unit 109 based on the state information, the vibration control is started based on the operation information by the control unit 110. This state is the "first stop" state. For this reason, the vibration has a small magnitude.

Figure 19C:
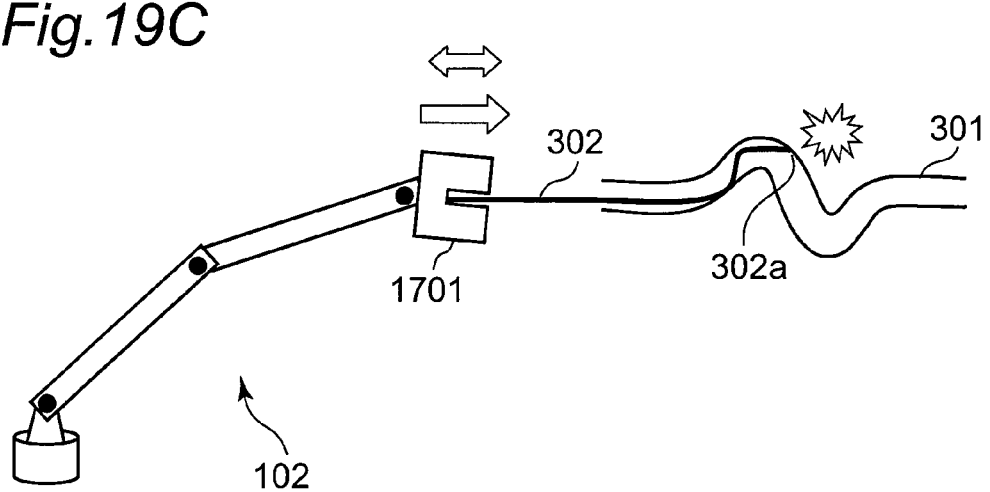
FIG. 19C is a view for explaining the operation procedure of the work for inserting the guide wire into the blood vessel (in the automatic reproduction) in the robot according to the first embodiment of the present disclosure.

On the other hand, FIG. 19C shows a time that the vibration control is carried out by the control unit 110 in addition to the reproduction of the teaching data during the reproduction of the teaching data through the control unit 110. Herein, the vibration control in the insertion direction is carried out over the guide wire 302 by the control unit 110.

Figure 19D:
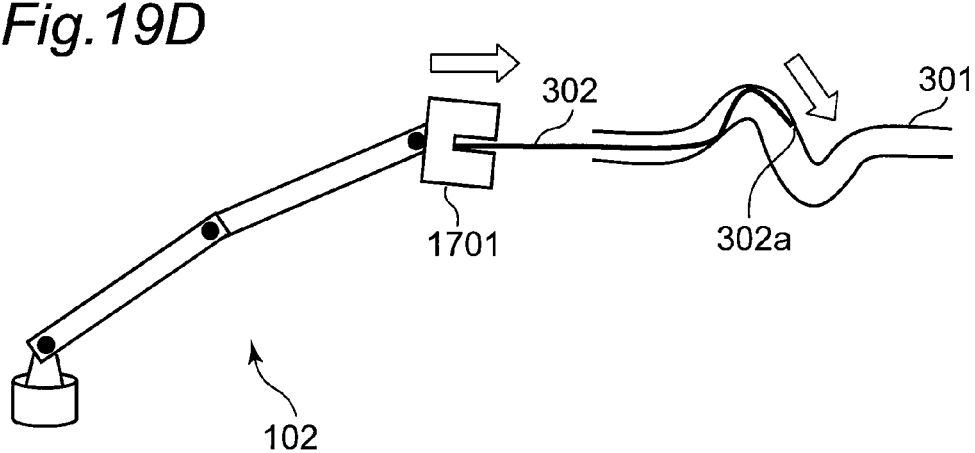
FIG. 19D is a view for explaining the operation procedure of the work for inserting the guide wire into the blood vessel (in the automatic reproduction) in the robot according to the first embodiment of the present disclosure.

FIG. 19D shows a time that the getting-stuck of the tip 302a of the guide wire 302 can be removed and the tip 302a can be moved as a result of the execution of the vibration control during the reproduction of the teaching data through the control unit 110. Herein, both the insertion information and the insertion member movement information are 1 and the vibration control is not carried out by the control unit 110. If the state specifying unit 108 decides that both the insertion information and the insertion member movement information are 0 (the "second stop" state) when the vibration control performed in FIG. 19C is to be carried out, the state specifying unit 108 decides that the getting-stuck of the tip 302a of the guide wire 302 cannot be removed and the magnitude of the vibration is set to be a magnitude in the "second stop" state (for example, the vibration information in FIG. 10C is 30) so that the vibration control is continuously carried out.

As described above, the vibration control is carried out by the control unit 110 to remove the getting-stuck of the tip 302a of the guide wire 302 in the automatic reproduction.

<Explanation in Manipulation>

In the manipulation, the operation of the robot arm 102 is controlled by the control unit 110 based on the operation information input from the operation information generating unit 109. An operation based on the operation information input from the operation information generating unit 109 is carried out by the control unit 110 in the case in which the vibration control is not performed, while an operation obtained by adding a vibration to the operation based on the operation information input from the operation information generating unit 109 is carried out by the control unit 110 if the vibration control is performed.

Referring to a manipulating method in the manipulation, a hand 2001 of the manipulator holds a force sensor 2002 for front arm link which is attached to the front arm link 1703 in the robot arm 102 as shown in FIGS. 20A to 20D. The magnitude of force applied to the robot arm 102 by the hand 2001 of the manipulator is measured by the force sensor 2002 for front arm link, and a value of the force measured by the force sensor 2002 for front arm link is input to the operation information generating unit 109 through the input/output IF 111. A movement amount of the robot arm 102 is generated depending on the input force value. As an example, a value obtained by multiplying the input force value by a gain is derived as the movement amount of the hand tip of the robot arm 102. As a result, the operation of the robot arm 102 is controlled by the control unit 110 depending on the value of the force measured by the force sensor 2002 for front arm link. This is one example.

In the manipulation, moreover, the manipulator can input ON or OFF of the vibration control mode to the state specifying unit 108 by using the input/output IF 111. The manipulator can also set the state specifying unit 108 to turn ON the vibration control mode at the start of the manipulation.

Figure 20A:
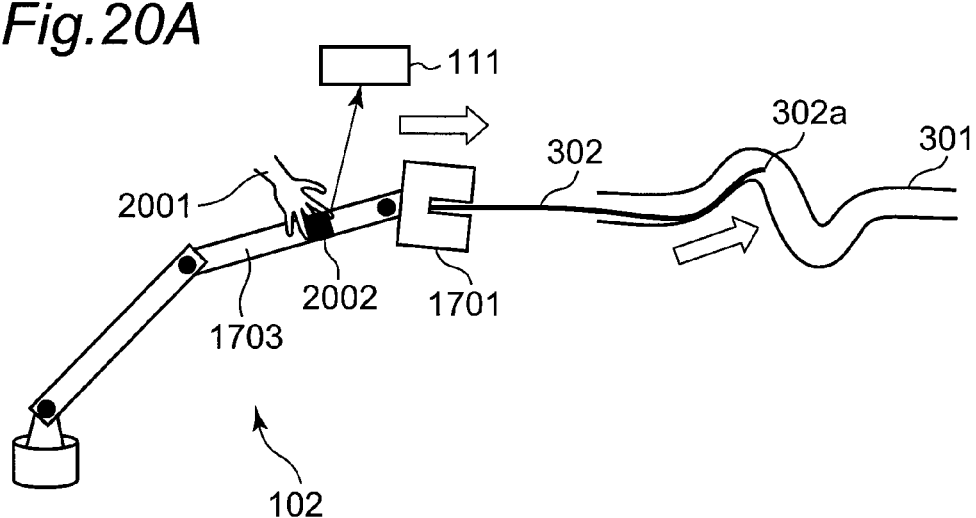
FIG. 20A is a view for explaining an operation procedure of a work for inserting a guide wire into a blood vessel (in manipulation) in the robot according to the first embodiment of the present disclosure.

FIG. 20A shows a time that a hand 2001 of the manipulator starts the manipulation of the robot arm 102. At this time, both the insertion information and the insertion member movement information are 1 and the vibration control is not carried out but an operation according to the manipulation of the hand 2001 of the manipulator is carried out by the control unit 110. In other words, when the state information in which the insertion information is 1, the insertion member movement information is 1, and the control information is 0 is input from the state specifying unit 108 to the operation information generating unit 109 and operation information having no vibration control is generated by the operation information generating unit 109 based on the state information, the operation of the robot arm 102 is started without the vibration control based on the operation information by the control unit 110. The manipulator turns ON the vibration control mode in the state specifying unit 108 by using the input/output IF 111 at this time.

Figure 20B:
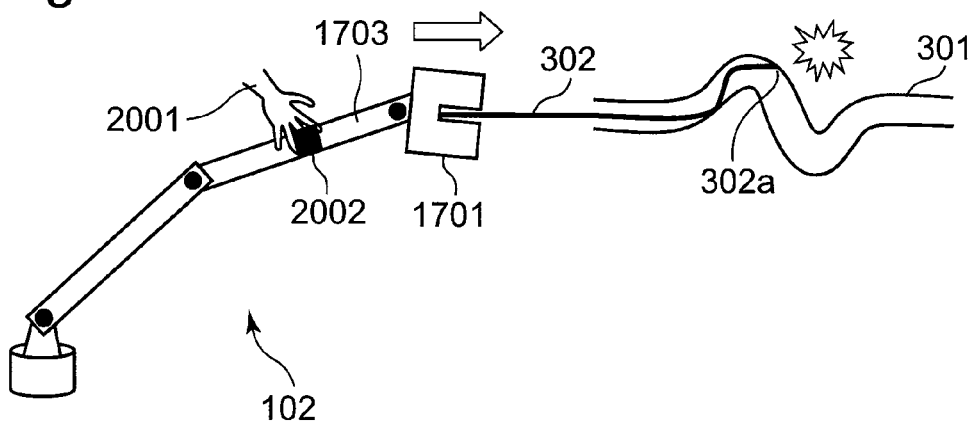
FIG. 20B is a view for explaining the operation procedure of the work for inserting the guide wire into the blood vessel (in manipulation) in the robot according to the first embodiment of the present disclosure.

FIG. 20B shows a time that the tip 302a of the guide wire 302 is gotten stuck in the blood vessel 301 and the movement of the tip 302a is thus stopped during the manipulation of the robot arm 102 through the hand 2001 of the manipulator. At this time, the insertion information is 1 and the insertion member movement information is 0, and the vibration control is started by the control unit 110. In other words, when the state information in which the insertion information is 1, the insertion member movement information is 0, and the control information is 1 is input from the state specifying unit 108 to the operation information generating unit 109, and the operation information for starting the vibration control is generated by the operation information generating unit 109 based on the state information, the vibration control is started based on the operation information by the control unit 110. This state is the "first stop" state. For this reason, the vibration has a small magnitude.

Figure 20C:
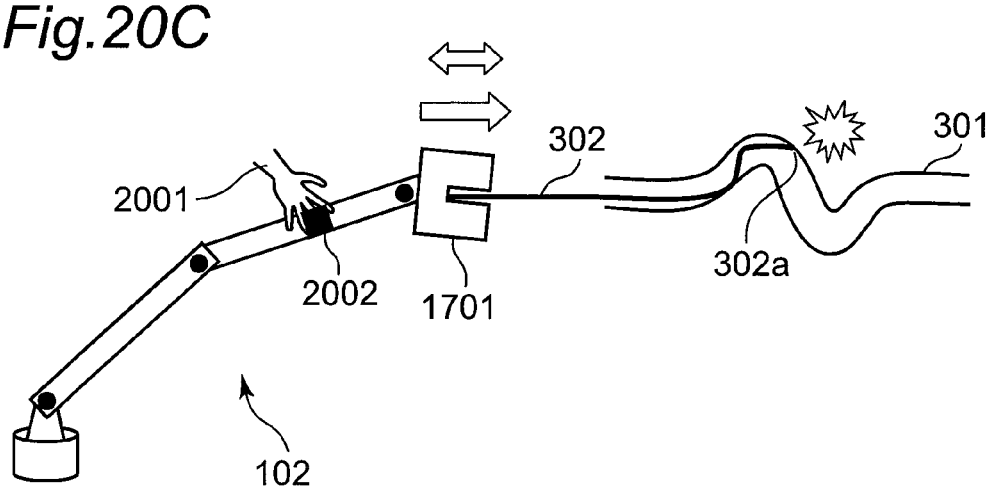
FIG. 20C is a view for explaining the operation procedure of the work for inserting the guide wire into the blood vessel (in the manipulation) in the robot according to the first embodiment of the present disclosure.

On the other hand, FIG. 20C shows a time that the vibration control is carried out by the control unit 110 in addition to the manipulation carried out by the hand 2001 of the manipulator during the manipulation of the robot arm 102 through the hand 2001 of the manipulator. Herein, the vibration control in the insertion direction is carried out over the guide wire 302 by the control unit 110.

Figure 20D:
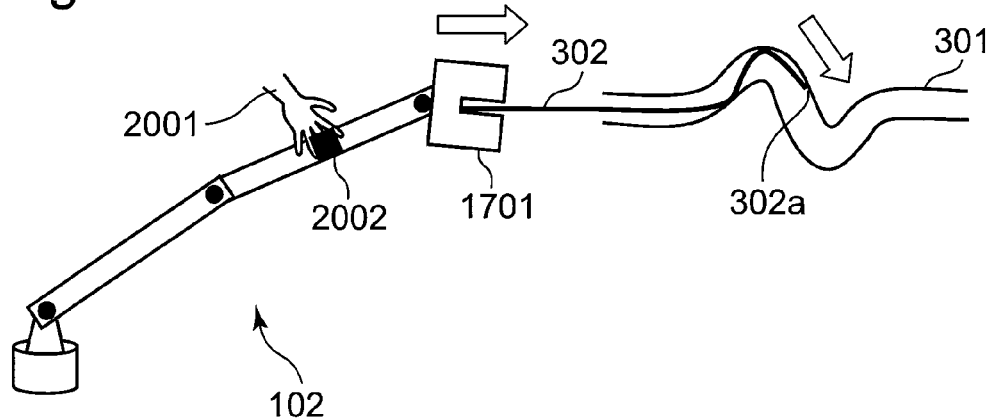
FIG. 20D is a view for explaining the operation procedure of the work for inserting the guide wire into the blood vessel (in the manipulation) in the robot according to the first embodiment of the present disclosure.

FIG. 20D shows a time that the getting-stuck of the tip 302a of the guide wire 302 can be removed and the tip 302a can be moved as a result of the execution of the vibration control during the manipulation of the robot arm 102 through the hand 2001 of the manipulator. Herein, both the insertion information and the insertion member movement information are 1 and the vibration control is not carried out by the control unit 110. If the state specifying unit 108 decides that both the insertion information and the insertion member movement information are 0 (the "second stop" state) when the vibration control performed in FIG. 20C is to be carried out, the state specifying unit 108 decides that the getting-stuck of the tip 302a of the guide wire 302 cannot be removed and the magnitude of the vibration is set to be a magnitude in the "second stop" state (for example, the vibration information in FIG. 10C is 30) so that the vibration control is continuously carried out.

As described above, the vibration control is carried out by the control unit 110 to remove the getting-stuck of the tip 302a of the guide wire 302 in the manipulation.

Although the description has been given by taking, as an example, the insertion of the guide wire 302 into the blood vessel 301 in the catheter inserting work, any insertion member can be inserted into a target such as a connector of a flexible substrate.

Figure 21:
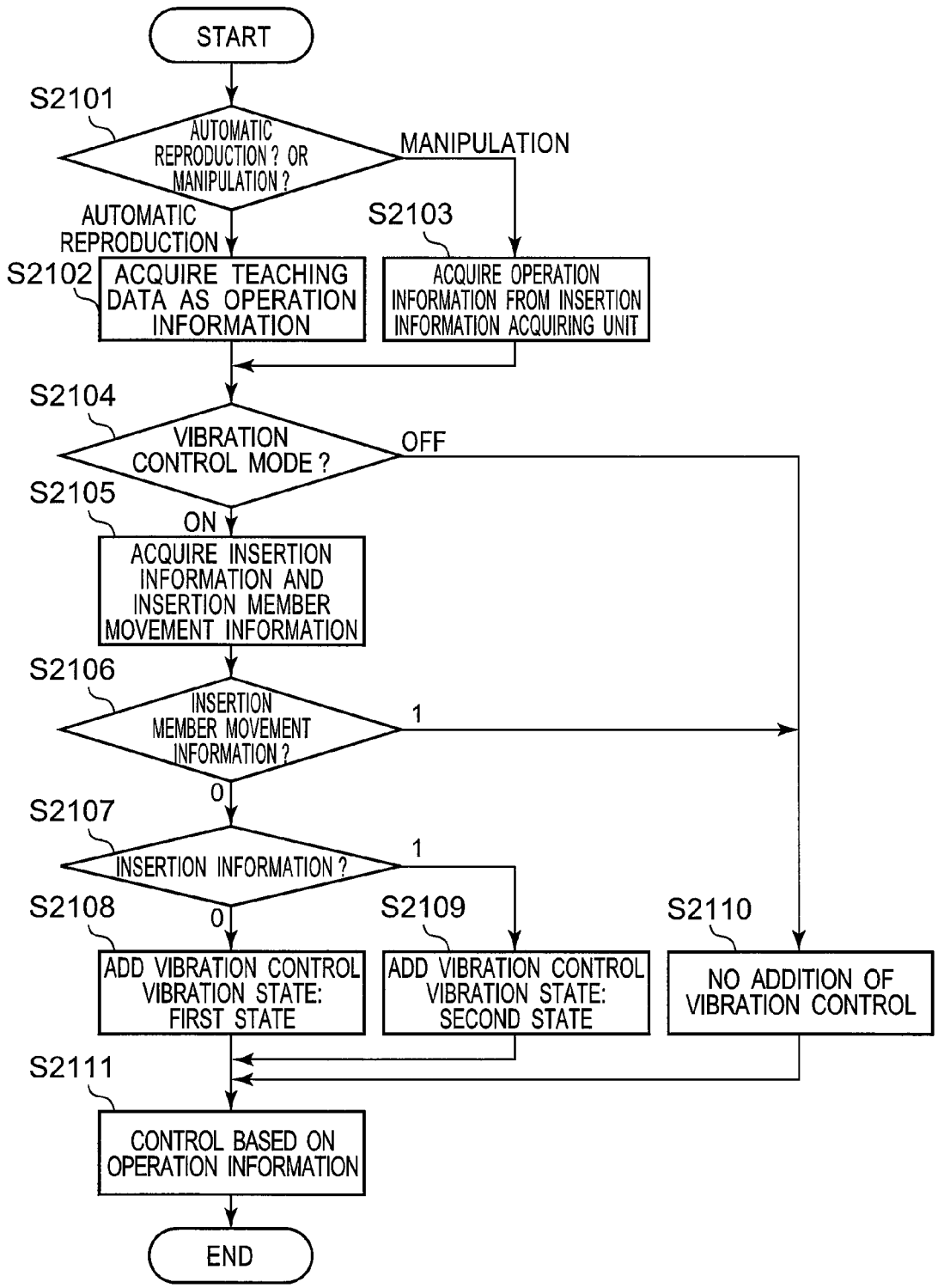
FIG. 21 is a flowchart showing a procedure for manipulating a control apparatus for the robot according to the first embodiment of the present disclosure.

Next, a procedure for manipulating the control apparatus 103 for the robot arm 102 according to the first embodiment will be described with reference to a flowchart of FIG. 21.

First of all, in step S2101, the manipulating procedure proceeds to step S2102 if the mode input from the input/output IF 111 to the state specifying unit 108 is the automatic reproduction mode, and the manipulating procedure proceeds to step S2103 if the input mode is the manipulation mode, in the input/output IF 111.

In step S2102, the teaching data stored in the internal storage unit of the operation information generating unit 109 is set to be the operation information in the operation information generating unit 109, and the manipulating procedure proceeds to step S2104.

In step S2103, information acquired from the insertion information acquiring unit 106 is set to be the operation information in the operation information generating unit 109, and the manipulating procedure proceeds to step S2104.

In step S2104, the state specifying unit 108 decides whether the vibration control mode is ON or OFF in the state specifying unit 108. If the state specifying unit 108 decides that the vibration control mode is ON, the manipulating procedure proceeds to step S2105. If the state specifying unit 108 decides that the vibration control mode is OFF, the manipulating procedure proceeds to step S2110. The manipulator selects the ON/OFF of the vibration control mode based on the information input to the state specifying unit 108 by using the input/output IF 111. The selection can be carried out for the following reason. The manipulator can select the case in which the inserting work is performed by only the manipulator or the case in which the vibration control is added to perform the inserting work, by his (her) intention.

In step S2105, the state specifying unit 108 acquires the insertion information from the insertion information acquiring unit 106 and acquires the insertion member movement information from the insertion member movement information acquiring unit 107, and the manipulating procedure proceeds to step S2106.

In step S2106, the manipulating procedure proceeds to step S2107 if the state specifying unit 108 decides that the value of the insertion member movement information acquired from the insertion member movement information acquiring unit 107 is 0, and the manipulating procedure proceeds to step S2110 if the state specifying unit 108 decides that the value of the insertion member movement information is 1.

In step S2107, the manipulating procedure proceeds to step S2108 if the state specifying unit 108 decides that the value of the insertion information acquired from the insertion information acquiring unit 106 is 0, and the manipulating procedure proceeds to step S2109 if the state specifying unit 108 decides that the value of the insertion information is 1.

In step S2108, the state specifying unit 108 generates the state information for carrying out the vibration control, and the manipulating procedure proceeds to step S2111. Herein, the magnitude of a vibration is made greater than that in the case of step S2109 (the first state in FIG. 21). Then, the manipulating procedure proceeds to step S2111.

In step S2109, the state specifying unit 108 generates the state information for carrying out the vibration control, and the manipulating procedure proceeds to step S2111. Herein, the magnitude of a vibration is made smaller than that in the case of step S2108 (the second state in FIG. 21). Then, the manipulating procedure proceeds to step S2111.

In step S2110, the state specifying unit 108 generates the state information for carrying out no vibration control, and the manipulating procedure proceeds to step S2111.

In step S2111, the operation information generating unit 109 acquires the state information from the state specifying unit 108, and adds the operation information for the vibration control to generate operation information if the vibration control is to be carried out. The operation information generating unit 109 generates the operation information directly from the acquired operation information if the vibration control is not to be carried out. The operation information is output from the operation information generating unit 109 to the control unit 110, and the operation of the robot arm 102 is controlled based on the operation information acquired in the control unit 110.

Modification Example

As a modification example of the first embodiment, there is provided a function for carrying out vibration control in the "first progress" state (the insertion information: 1, the insertion member movement information: 1) in addition to the function of the state specifying unit 108.

Figure 22:
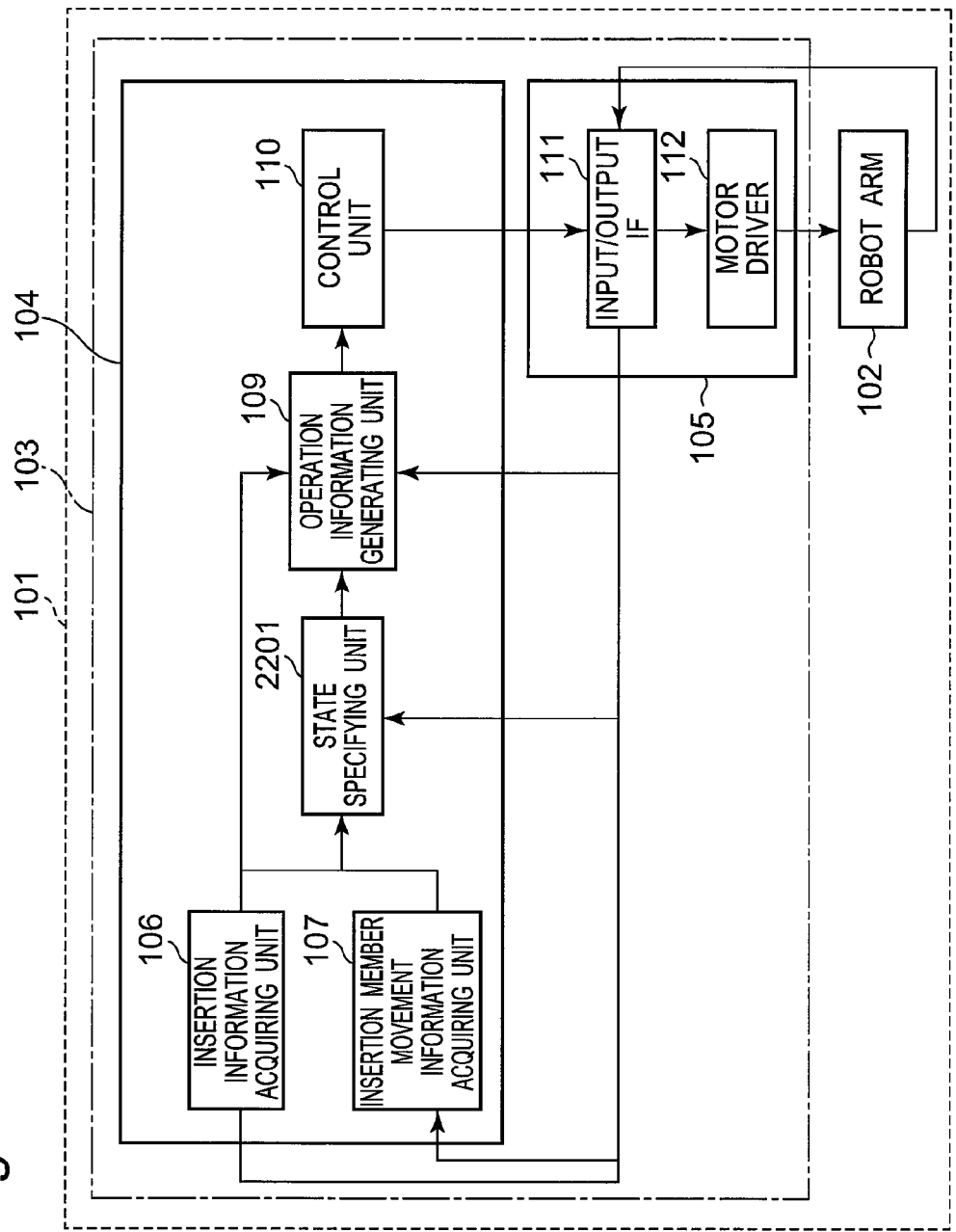
FIG. 22 is a block diagram showing a robot arm in a robot according to a modification example of the first embodiment of the present disclosure.

FIG. 22 is a block diagram showing a robot 101 according to the modification example. Since the robot arm 102; the peripheral apparatus 105; and the insertion information acquiring unit 106, the insertion member movement information acquiring unit 107, the operation information generating unit 109, and the control unit 110 in the control apparatus body unit 104 in the robot 101 according to the modification example are the same as those in the first embodiment, they have common reference numerals and the description of common parts are omitted, and only different parts will be explained below in detail.

A state specifying unit 2201 is provided in the control apparatus body unit 104 in place of the state specifying unit 108 according to the first embodiment, and has a function for carrying out vibration control in a "first progress" state (insertion information: 1, insertion member movement information: 1) in addition to the function of the state specifying unit 108 according to the first embodiment. The additional function will be described below.

Description will be given to that the vibration control is carried out also in the "first progress" state (the insertion information: 1, the insertion member movement information: 1). In the first embodiment, the vibration control is carried out in only the state in which the insertion member movement information is 0 (the "first stop" state and the "second stop" state). On the other hand, in the modification example of the first embodiment, the vibration control is carried out in the "first progress" state in addition to the two states. However, in the "second progress" state (the insertion information: 0, the insertion member movement information: 1), the vibration control is not carried out in the same manner as in the first embodiment. It is because the control is disabled in the "second progress" state and such a phenomenon that the insertion member jumps occurs, so that a more dangerous state is brought in the case in which the vibration control is applied in comparison between the case in which the vibration control is applied and the case in which the vibration control is not applied.

The state information will be described with reference to FIGS. 23A to 23D. FIGS. 23A to 23D correspond to the states described with FIGS. 8B to 8E, respectively.

FIG. 23A corresponds to the state of FIG. 8B and a "first progress" state in which the insertion information is 1 and the insertion member movement information is 1. For this reason, the control information is 1 which represents to carry out the vibration control. In addition, the vibration information is five and is shown to be smaller than the values of the vibration information in FIGS. 23B and 23C. For instance, a vibration (repetition) motion having an amplitude of 0.02 mm is taken as an example of the vibration. A manipulator can input the value to the state specifying unit 108 by using the input/output IF 111. However, it is impossible to input a greater value than the value of the vibration information in FIGS. 23B and 23C. The modification example of the first embodiment has a feature that the control information of FIG. 23A is 1.

FIG. 23B corresponds to the state of FIG. 8C and a "first stop" state in which the insertion information is 1 and the insertion member movement information is 0. For this reason, the control information is 1 which represents to carry out the vibration control. In addition, the vibration information is 15 and is shown to be greater than the value of the vibration information of FIG. 23A and smaller than the value of the vibration information in FIG. 23C. For instance, a vibration (repetition) motion having an amplitude of 0.06 mm is taken as an example of the vibration. The manipulator can input the value to the state specifying unit 108 by using the input/output IF 111. However, it is impossible to input a smaller value than the value of the vibration information in FIG. 23A and to input a greater value than the value of the vibration information in FIG. 23C.

FIG. 23C corresponds to the state of FIG. 8D and a "second stop" state in which the insertion information is 0 and the insertion member movement information is 0. For this reason, the control information is 1 which represents to carry out the vibration control. In addition, the vibration information is 30 and is shown to be greater than the values of the vibration information in FIGS. 23A and 23B. For instance, a vibration (repetition) motion having an amplitude of 0.12 mm is taken as an example of the vibration. The manipulator can input the value to the state specifying unit 108 by using the input/output IF 111. However, it is impossible to input a smaller value than the values of the vibration information in FIGS. 23A and 23B.

FIG. 23D corresponds to the state of FIG. 8E and presents a "second progress" state in which the insertion information is 0 and the insertion member movement information is 1. For this reason, the control information is 0 which represents that the vibration control is not to be carried out.

In the state specifying unit 2201, the magnitude of the vibration is made smaller in the "first progress" state than in the "first stop" state or the "second stop" state. This can be explained from a result obtained by execution of the following experiment.

Figure 24:
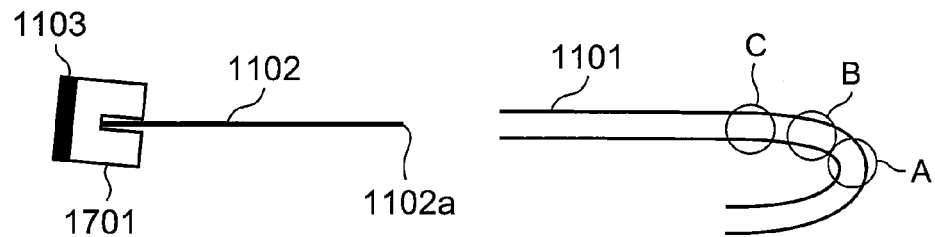
FIG. 24 is a view for explaining an insertion experiment of a wire into a tube in the robot according to the modification example of the first embodiment of the present disclosure.
Figure 25A:
FIG. 25A is a view for explaining a vibration start position in the insertion experiment of the wire into the tube in the robot according to the modification example of the first embodiment of the present disclosure.
Figure 25B:
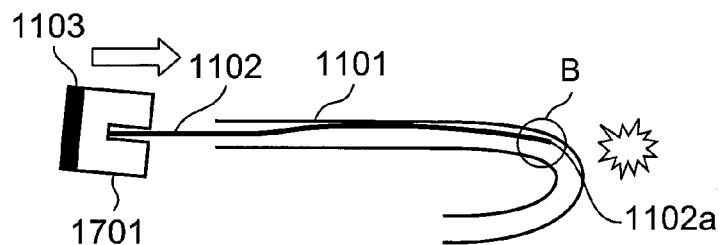
FIG. 25B is a view for explaining the vibration start position in the insertion experiment of the wire into the tube in the robot according to the modification example of the first embodiment of the present disclosure.
Figure 25C:
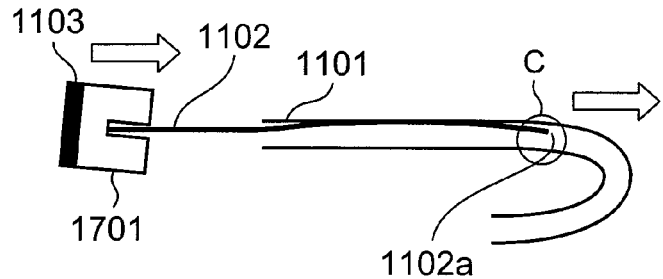
FIG. 25C is a view for explaining the vibration start position in the insertion experiment of the wire into the tube in the robot according to the modification example of the first embodiment of the present disclosure.

In the experiment in which the wire 1102 is inserted into the tube 1101 described with reference to FIG. 11, a vibration start position indicated by the symbol C of FIG. 24 is added. A vibration start position indicated by the symbol A represents the "second stop" state shown in FIG. 25A. A vibration start position indicated by the symbol B represents the "first stop" state shown in FIG. 25B. On the other hand, the vibration start position indicated by the symbol C represents a "first progress" state in which a position of a tip 1102a of a wire 1102 is moved and a position of a hand 1701 is also moved as shown in FIG. 25C. FIG. 26 shows results of three experiments in which the hand 1701 is vibrated and inserted from the vibration start positions in three places in total in which the "first progress" state is added. There are compared insertion distances at which the wire 1102 is gotten stuck in the middle part of the tube 1101 and the wire 1102 cannot advance.

In FIG. 26, the vibration start position represents values of the symbols A, B, and C in FIG. 24. An insertion distance (mm) indicates a distance at which the wire 1102 is inserted into the tube 1101, and a longer distance represents that the wire 1102 is inserted into a further inner part. From FIG. 26, it is apparent that the insertion distance is longer in the vibration start position C as compared with the vibration start position A or the vibration start position B. This indicates that the wire 1102 can be inserted into a further inner part by a vibration with the vibration started in the "first progress" state as compared with the case in which the vibration is started in the "first stop" state or the "second stop" state. In other words, the start of the vibration in the vibration start position represented by the symbol A and the vibration start position represented by the symbol B implies that the vibration is not started in the vibration start position represented by the symbol C and the insertion distance is longer and the wire 1102 can be inserted into the further inner part by the vibration more easily in the case of the vibration start position represented by the symbol C in comparison between the case of the vibration start positions represented by the symbols A and B and the case of the vibration start position represented by the symbol C in FIG. 26.

Figure 27:
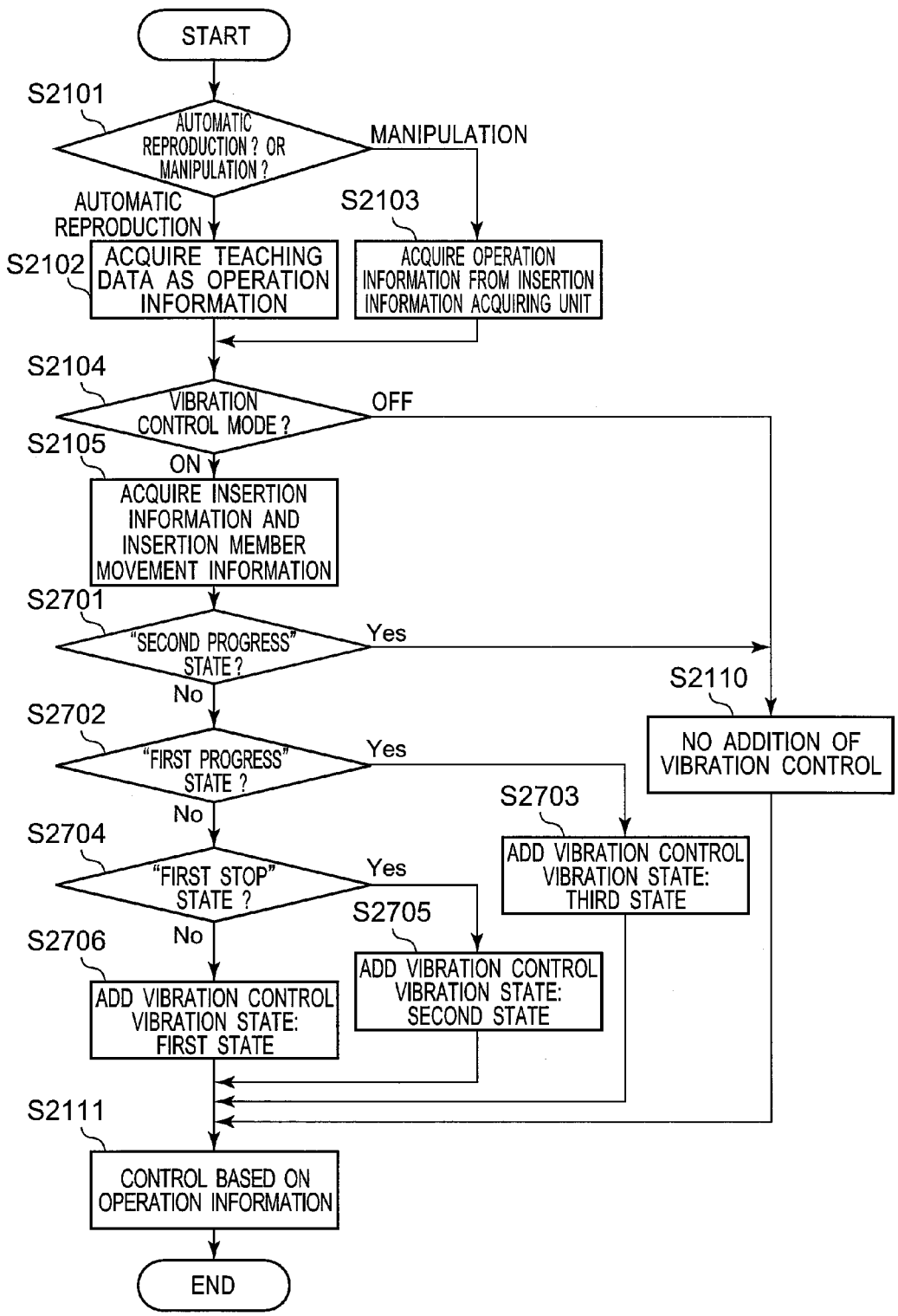
FIG. 27 is a flowchart in a manipulation procedure of a control apparatus for the robot according to the modification example of the first embodiment of the present disclosure.

A procedure for manipulating the control apparatus 103 for the robot arm 102 according to the modification example of the first embodiment will be described with reference to a flowchart of FIG. 27.

In step S2101, the manipulating procedure proceeds to step S2102 if the mode input from the input/output IF 111 to the state specifying unit 108 is the automatic reproduction mode, and the manipulating procedure proceeds to step S2103 if the input mode is the manipulation mode, in the input/output IF 111.

In step S2102, the teaching data stored in the internal storage unit of the operation information generating unit 109 is set to be the operation information in the operation information generating unit 109, and the manipulating procedure proceeds to step S2104.

In step S2103, information acquired from the insertion information acquiring unit 106 is set to be the operation information in the operation information generating unit 109, and the manipulating procedure proceeds to step S2104.

In step S2104, the state specifying unit 108 decides whether the vibration control mode is ON or OFF in the state specifying unit 108. If the state specifying unit 108 decides that the vibration control mode is ON, the manipulating procedure proceeds to step S2105. If the state specifying unit 108 decides that the vibration control mode is OFF, the manipulating procedure proceeds to step S2110. The manipulator selects the ON/OFF of the vibration control mode based on the information input to the state specifying unit 108 by using the input/output IF 111.

In step S2105, the state specifying unit 2201 acquires the insertion information from the insertion information acquiring unit 106 and acquires the insertion member movement information from the insertion member movement information acquiring unit 107, and the manipulating procedure proceeds to step S2701.

In step S2701, the manipulating procedure proceeds to step S2110 if the state specifying unit 2201 makes a decision of the "second progress" state in which the value of the insertion information acquired from the insertion information acquiring unit 106 is 0 and the value of the insertion member movement information acquired from the insertion member movement information acquiring unit 107 is 1, and the manipulating procedure proceeds to step S2702 if the state specifying unit 2201 does not make a decision of the "second progress" state.

In step S2110, the state specifying unit 2201 generates the state information for carrying out no vibration control, and the manipulating procedure proceeds to step S2111.

In step S2702, the manipulating procedure proceeds to step S2703 if the state specifying unit 2201 makes a decision of the "first progress" state in which the value of the insertion information acquired from the insertion information acquiring unit 106 is 1 and the value of the insertion member movement information acquired from the insertion member movement information acquiring unit 107 is 1, and the manipulating procedure proceeds to step S2704 if the state specifying unit 2201 does not make a decision of the "first progress" state.

In step S2703, the state specifying unit 2201 generates state information for carrying out the vibration control, and the manipulating procedure proceeds to step S2111. Herein, the magnitude of the vibration is set to be the smallest as compared with the cases of the other steps (State 3 in FIG. 27).

In step S2704, if the state specifying unit 2201 makes a decision of the "first stop" state in which the value of the insertion information acquired from the insertion information acquiring unit 106 is 1 and the value of the insertion member movement information acquired from the insertion member movement information acquiring unit 107 is 0, the manipulating procedure proceeds to step S2705. If the state specifying unit 2201 makes a decision of the "second stop" state in which the value of the insertion information acquired from the insertion information acquiring unit 106 is 0 and the value of the insertion member movement information acquired from the insertion member movement information acquiring unit 107 is 0, the manipulating procedure proceeds to step S2706.

The state specifying unit 2201 generates the state information for carrying out the vibration control in step S2705, and the manipulating procedure proceeds to step S2111. Herein, the magnitude of a vibration is made greater than that in the case of step S2703 and is made smaller than that in the case of step S2706 (the second state in FIG. 27).

The state specifying unit 2201 generates the state information for carrying out the vibration control in step S2706, and the manipulating procedure proceeds to step S2111. Herein, the magnitude of a vibration is made the greatest as compared with the cases of the other steps (the first state in FIG. 27).

In step S2111, the operation information generating unit 109 acquires the state information from the state specifying unit 2201 and adds the operation information for the vibration control to generate operation information if the vibration control is to be carried out. The operation information generating unit 109 generates the operation information directly from the acquired operation information if the vibration control is not to be carried out. The operation information is output from the operation information generating unit 109 to the control unit 110, and the operation of the robot arm 102 is controlled based on the operation information acquired in the control unit 110.

Effect of the First Embodiment

In the case in which the getting-stuck of the tip 302a of the guide wire 302 occurs in the work for inserting the insertion member such as the guide wire 302, the state of the guide wire 302 is specified by the state specifying unit 108 and there is carried out vibration control having such a magnitude as not to apply an excessive load to the blood vessel 301 depending on the state. Consequently, it is possible to remove the getting-stuck with a vibration having such a magnitude as not to cause the overload. Specifically, the four states of the guide wire 302 (the "first progress" state, the "first stop" state, the "second stop" state, and the second "progress" state) are distinguished from each other, and it is automatically decided whether the vibration is to be applied to the guide wire 302 or not depending on the respective states, thereby carrying out the control. Thus, it is possible to remove the getting-stuck without applying the excessive load to the blood vessel 301. Herein, the "first progress" state represents a state in which a part other than the tip of the insertion member (a non-tip area) (a hand holding portion for example, however, the portion is not restricted to the hand holding portion but any portion other than the tip may be employed) is moved and the tip of the insertion member is also moved, specifically, a state in which the hand 1701 is moved in the insertion direction and the guide wire 302 is also moved. The "first stop" state represents a state in which a portion other than the tip of the insertion member is moved but the tip of the insertion member is not moved, specifically, a state in which the hand 1701 is moved in the insertion direction and the guide wire 302 is not moved. The "second stop" state represents a state in which the portion other than the tip of the insertion member is not moved and the tip of the insertion member is not moved, specifically, a state in which the hand 1701 is not moved in the insertion direction and the guide wire 302 is not moved. The "second progress" state represents a state in which the portion other than the tip of the insertion member is not moved and the tip of the insertion member is moved, specifically, a state in which the hand 1701 is not moved in the insertion direction and the guide wire 302 is moved.

Second Embodiment

Figure 28:
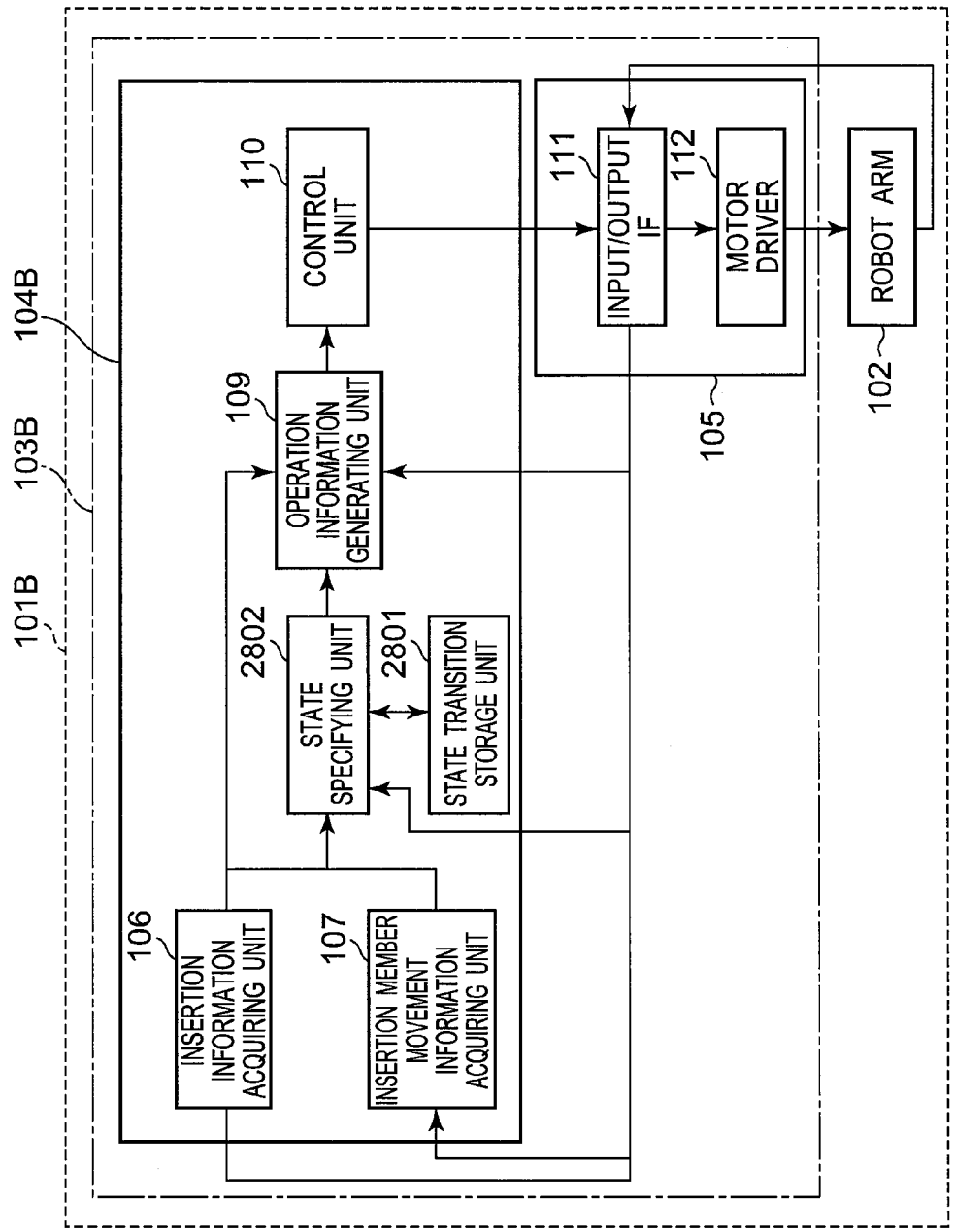
FIG. 28 is a block diagram showing a robot arm in a robot according to a second embodiment of the present disclosure.

FIG. 28 is a block diagram showing a robot 101B according to an example of an insertion apparatus in accordance with a second embodiment of the present disclosure. A control apparatus 103B of the robot arm 102 according to an example of a control apparatus of an insertion apparatus in accordance with the second embodiment of the present disclosure has a feature that a control apparatus body unit 104B is provided with a state transition storage unit 2801 and a state specifying unit 2802. Since the robot arm 102; the peripheral apparatus 105; and the insertion information acquiring unit 106, the insertion member movement information acquiring unit 107, the operation information generating unit 109, and the control unit 110 in the control apparatus body unit 104B of the control apparatus 103B in the robot 101B according to the second embodiment of the present disclosure are the same as those in the first embodiment, they have common reference numerals and the description of common parts are omitted, and only different parts will be explained below in detail.

The state transition storage unit 2801 acquires insertion information, insertion member movement information, and time information from the state specifying unit 2802, generates state transition information, and outputs the generated state transition information to the state specifying unit 2802. FIG. 29 shows the state transition information to be generated by the state transition storage unit 2801. The state transition information has the insertion information and the insertion member movement information arranged in time-series order, and the newest information is stored in a rearmost part (as an example, a lowermost column in FIG. 29). Referring to the state transition information shown in FIG. 29, the state makes the following transition and the newest state is a "first stop" state (the insertion information: 1, the insertion member movement information: 0):

"First progress" state (insertion information: 1, insertion member movement information: 1)→

"First stop" state (insertion information: 1, insertion member movement information: 0)→

"Second stop" state (insertion information: 0, insertion member movement information: 0)→

"First stop" state (insertion information: 1, insertion member movement information: 0).

Figure 30:
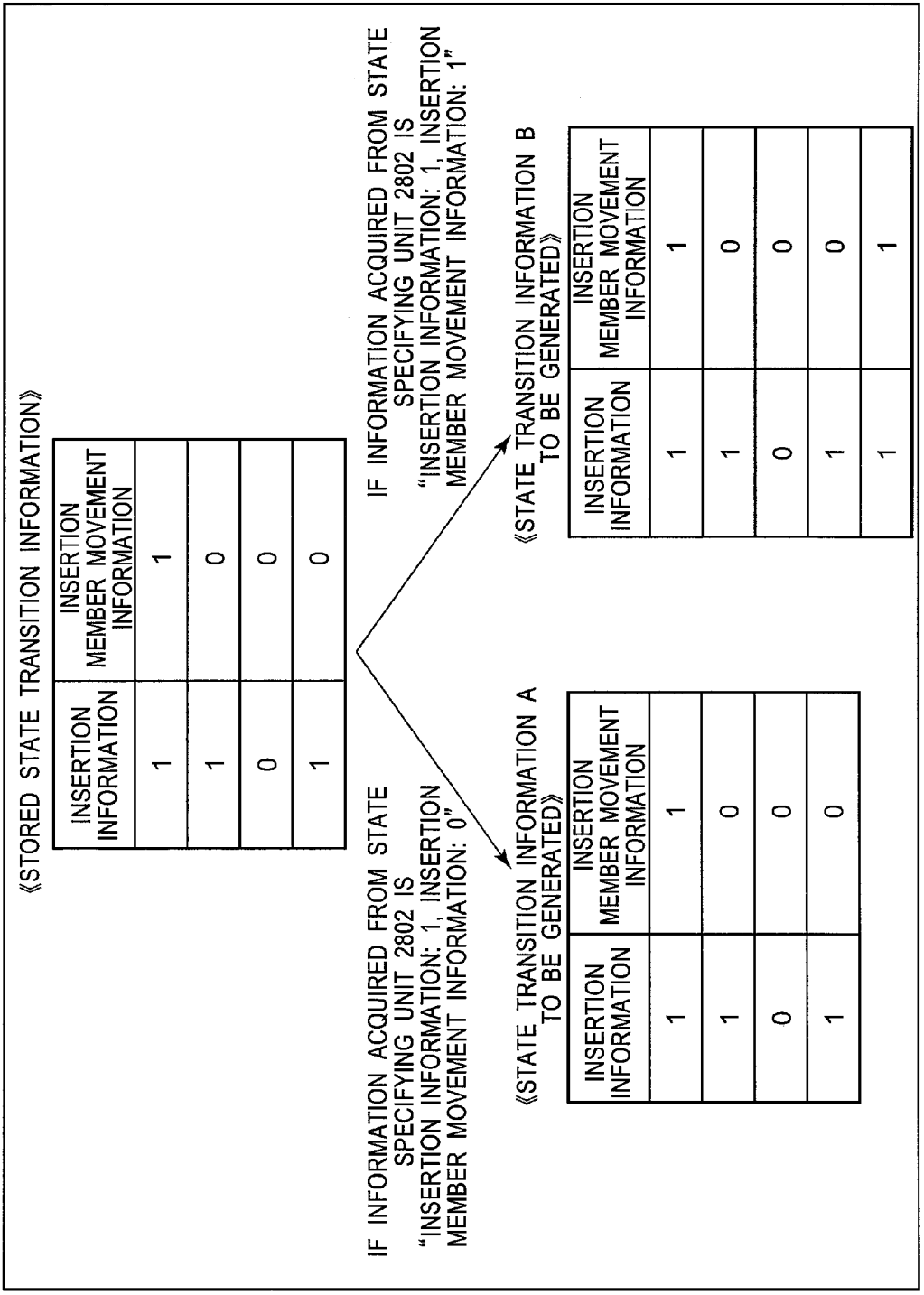
FIG. 30 is a view for explaining a method of generating the state transition information in the robot according to the second embodiment of the present disclosure.

A method of generating state transition information in the state transition storage unit 2801 will be descried with reference to FIG. 30. In the case in which the state transition information stored in the state transition storage unit 2801 (see a table of "stored state transition information" in FIG. 30) is the state transition information shown in FIG. 29, the newest state is the "first stop" state (the insertion information: 1, the insertion member movement information: 0). The newest state and the insertion information and insertion member movement information acquired from the state specifying unit 2802 are compared with each other by the state transition storage unit 2801. If the state transition storage unit 2801 decides that the newest state (the "first stop" state) and the information (the "first stop" state) acquired from the state specifying unit 2802 are identical to each other as a result of the comparison, nothing is carried out over the state transition information (see a table of "generated state transition information A" in FIG. 30). If the state transition storage unit 2801 decides that the newest state (the "first stop" state) is different from the state (the "first progress" state) acquired from the state specifying unit 2802, the acquired insertion information and the acquired insertion member movement information are added to the state transition information in order (in a lowermost column) (see a table of "generated state transition information B" in FIG. 30).

The state transition storage unit 2801 outputs the generated state transition information to the state specifying unit 2802.

The state specifying unit 2802 is provided in the control apparatus body unit 104B in place of the state specifying unit 2201, and has a function for changing the magnitude of a vibration based on the state transition information in addition to the function of the state specifying unit 2201 according to the first embodiment. The adding function will be described below.

Description will be given to that the magnitude of the vibration is changed based on the state transition information in the state specifying unit 2802. The state specifying unit 2802 generates the state information based on the state transition information acquired from the state transition storage unit 2801. A method of generating the state information by the state specifying unit 2802 will be explained below. The generating method differs for every newest state of the state transition information which is acquired from the state transition storage unit 2801.

Figure 31:
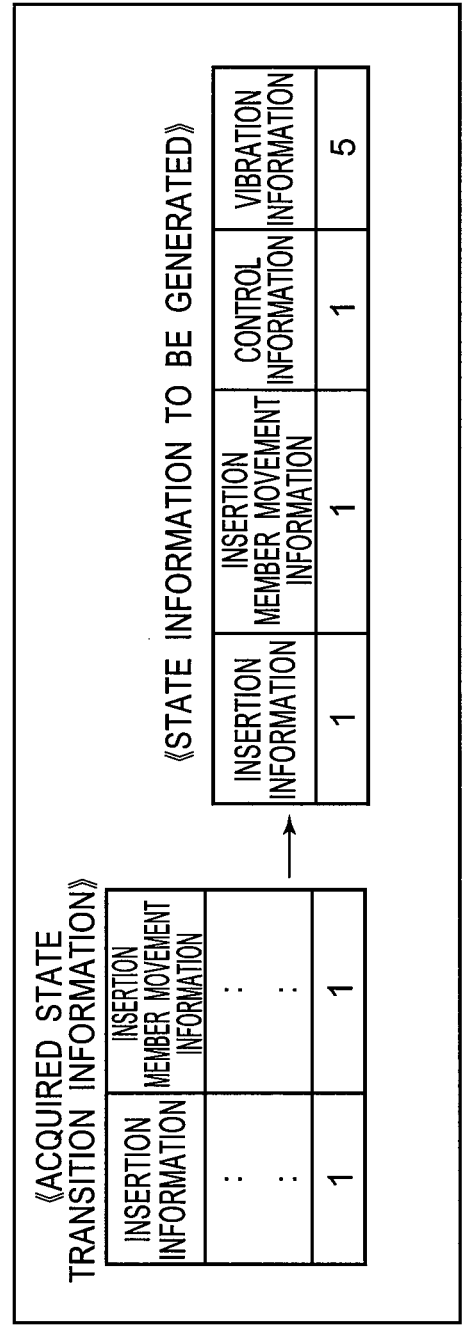
FIG. 31 is a view for explaining a method of generating state information (the newest state is a "first progress" state) in the robot according to the second embodiment of the present disclosure.

The case in which the newest state is the "first progress" state (the insertion information: 1, the insertion member movement information: 1) will be described with reference to FIG. 31. In the case in which the newest state of the acquired state transition information is the "first progress" state (see a lowermost column in a table of the "acquired state transition information" on a left side in FIG. 31), the control information is set to be 1 in the state specifying unit

2802 in order to carry out vibration control. In the state specifying unit 2802, the magnitude of the vibration is set to have a certain value (for example, 5) irrespective of the state transition to reach the newest state (see a table of the "generated state information" on a right side of FIG. 31). As an example of the vibration, a vibration (repetition) motion having an amplitude of 0.02 mm is taken. However, the magnitude of the vibration needs to have a smaller value than the vibration information in the case in which the newest state is the "first stop" state or the "second stop" state. The manipulator can input the value to the state specifying unit 2802 by using the input/output IF 111. However, the manipulator cannot input a greater value than values of vibration information in FIGS. 32A, 32B, and 33A to 33C.

The case in which the newest state is the "first stop" state (the insertion information: 1, the insertion member movement information: 0) will be described with reference to FIGS. 32A and 32B.

Figure 32B:
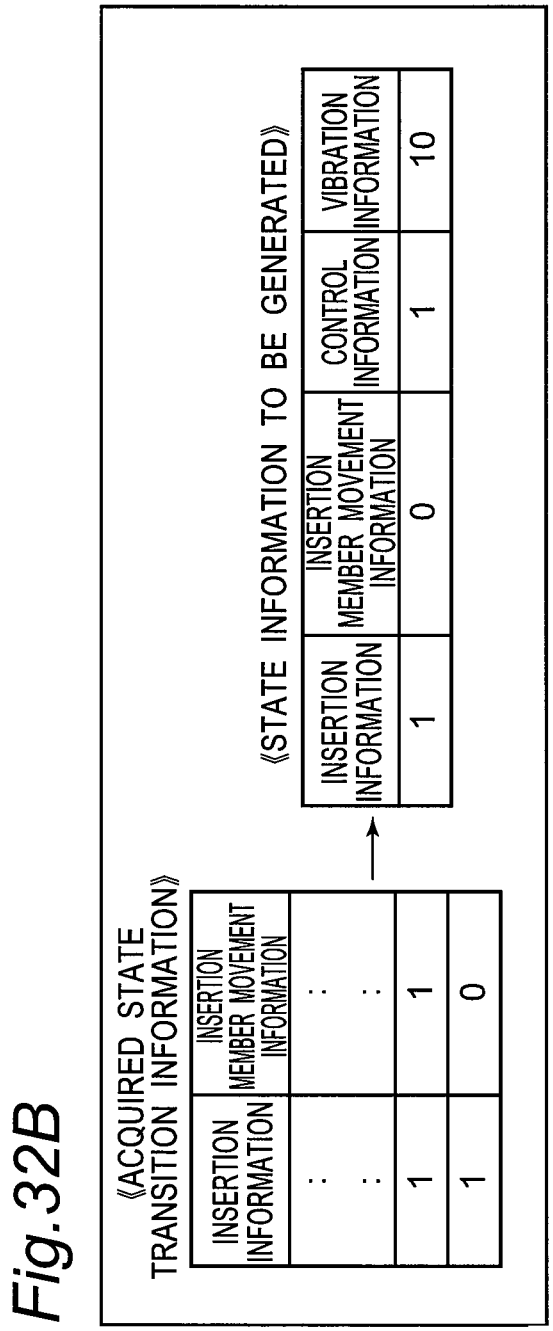
FIG. 32B is a view for explaining the method of generating state information (the newest state is the "first stop" state) in the robot according to the second embodiment of the present disclosure.

In the case in which the newest state of the acquired state transition information is the "first stop" state (see a lowermost column in a table of "acquired state transition information" on a left side of FIG. 32A), the control information is set to be 1 in order to carry out the vibration control. Referring to the magnitude of the vibration, the value of the vibration information is varied (see a table of "generated state information" on the right side of FIG. 32A) depending on a state brought immediately before the newest state. A previous state to the state brought immediately before the newest state is not taken into consideration. In the case in which the state brought immediately before the newest state is the "first progress" state (see a lowermost column in a table of "acquired state transition information" on a left side of FIG. 32B), the magnitude of the vibration is set to be smaller (see a table of "generated state information" on the right side of FIG. 32B) as compared with the case in which the state brought immediately before the newest state is a state other than the "first progress" state (see the lowermost column in the table of "the acquired state transition information" on the left side of FIG. 32A). As an example, the vibration information is set to be 15 (for instance, a vibration (repetition) motion having an amplitude of 0.06 mm) in the case of FIG. 32A and the vibration information is set to be 10 (for instance, a vibration (repetition) motion having an amplitude of 0.04 mm) in the case of FIG. 32B. This is caused by the fact that getting-stuck can be removed with a smaller vibration in the case in which the vibration control is started in a state having small flexure than the case in which the vibration is started in a state having great flexure. Furthermore, it is necessary to set the value of the vibration information to be greater than that in the case in which the newest state is the "first progress" state and to be smaller than that in the case in which the newest state is the "second stop" state. The manipulator can input the value of the vibration information to the state specifying unit 2802 by using the input/output IF 111. However, a smaller value than the value of the vibration information in FIG. 31 or a greater value than the value of the vibration information in FIGS. 33A to 33C cannot be input as the value of the vibration information.

The case in which the newest state is the "second stop" state (the insertion information: 0, the insertion member movement information: 0) will be described with reference to FIGS. 33A to 33C.

Figure 33A:
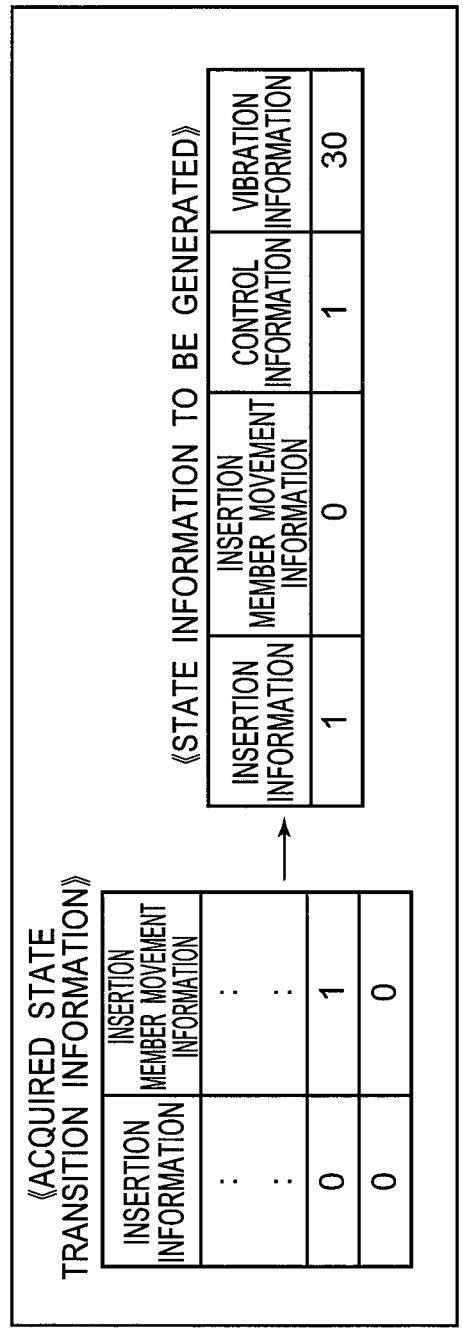
FIG. 33A is a view for explaining the method of generating state information (the newest state is a "second stop" state) in the robot according to the second embodiment of the present disclosure.
Figure 33B:
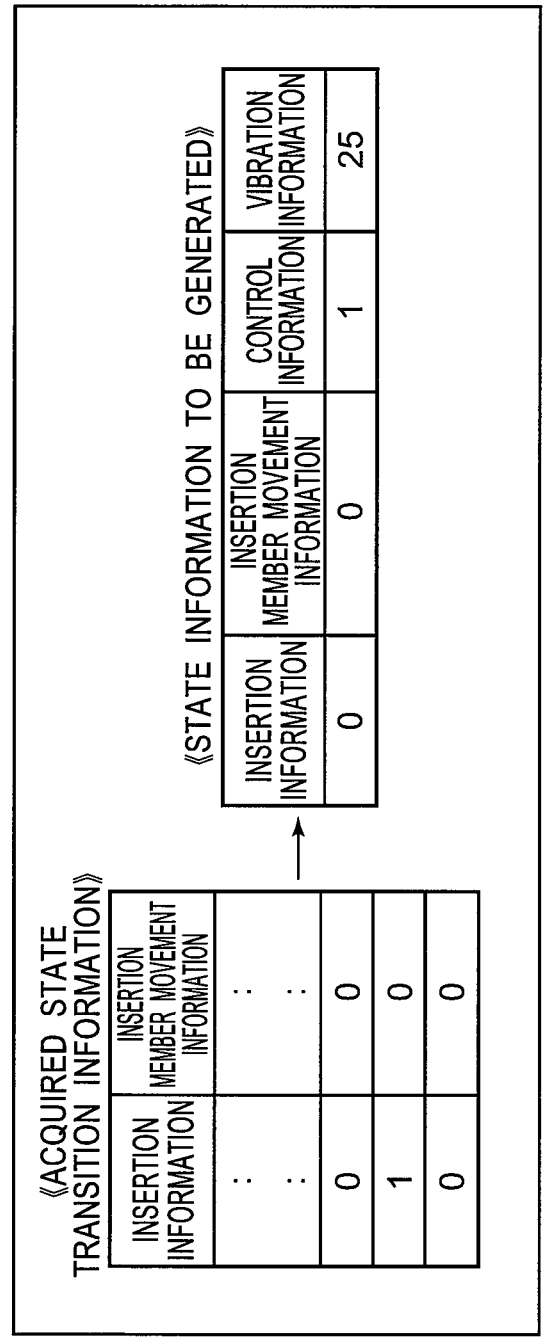
FIG. 33B is a view for explaining the method of generating state information (the newest state is the "second stop" state) in the robot according to the second embodiment of the present disclosure.

In the case in which the newest state of the acquired state transition information is the "second stop" state (see a lowermost column in a table of "acquired state transition information" on a left side of FIGS. 33A to 33C), the control information is set to be 1 in the state specifying unit 2802 in order to carry out the vibration control. Referring to the magnitude of the vibration, the value of the vibration information is varied depending on a state brought immediately before the newest state and a second previous state brought from the newest state (see a table of "generated state information" on the right side of FIGS. 33A to 33C). A previous state to the second previous state brought from the newest state is not taken into consideration. In the case in which the state brought immediately before the newest state is the "first stop" state in the state specifying unit 2802 (FIGS. 33B and 33C), the magnitude of the vibration is set to be smaller as compared with the case in which the state brought immediately before the newest state is a state other than the "first stop" state (FIG. 33A (for example, a vibration (repetition) motion having an amplitude of 0.12 mm)). In the case in which the state brought immediately before the newest state is the "first stop" state in the state specifying unit 2802 and the second previous state to the newest state is the "first progress" state (FIG. 33C ((for example, a vibration (repetition) motion having an amplitude of 0.08 mm))), furthermore, the magnitude of the vibration is reduced as compared with the case in which the second previous state to the newest state is a state other than the "first progress" state (FIG. 33B (for example, a vibration (repetition) motion having an amplitude of 0.10 mm)). This is caused by the fact that the getting-stuck can be removed with a smaller vibration in the case in which the vibration control is started in a state having small flexure than the case in which the vibration is started in a state having great flexure. Furthermore, it is necessary to set the value of the vibration information to be greater than that in the case in which the newest state is the "first progress" state or the "first stop" state. The manipulator can input the value of the vibration information to the state specifying unit 2802 by using the input/output IF 111. However, a smaller value than the value of the vibration information in FIGS. 31, 32A, and 32B cannot be input as the value of the vibration information.

Figure 34:
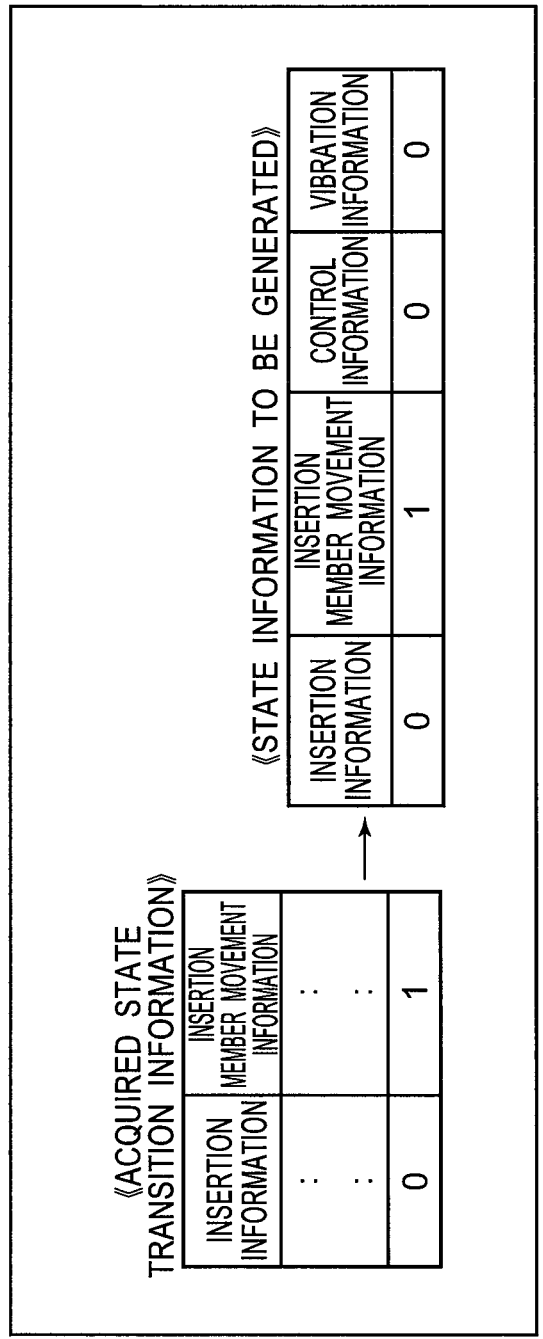
FIG. 34 is a view for explaining the method of generating state information (the newest state is a "second progress" state) in the robot according to the second embodiment of the present disclosure.

The case in which the newest state is the "second progress" state (the insertion information: 0, the insertion member movement information: 1) will be described with reference to FIG. 34. In the case in which the newest state of the acquired state transition information is the "second progress" state (see a lowermost column in a table of "acquired state transition information" on a left side of FIG. 34), the control information is set to be 0 in order not to carry out the vibration control. Moreover, the vibration information is also set to be 0 (see a table of the "generated state information" on a right side of FIG. 34).

The function described above is added in the state specifying unit 2802 according to the second embodiment.

<Explanation of Operation Procedure>

A procedure for inserting the insertion member through the insertion apparatus according to the second embodiment will be described for the automatic reproduction and the manipulation. Referring to the selection of the automatic reproduction mode or the manipulation mode, a manipulator can input information about which mode is to be selected, to the operation information generating unit 109 by using the input/output IF 111.

<Explanation of Automatic Reproduction>

In the automatic reproduction, the operation of the robot arm 102 is controlled by the control unit 110 based on the operation information about the robot arm 102 in the teaching which is stored in the internal storage unit of the operation information generating unit 109. Under the control of the control unit 110, the operation in the teaching is carried out by the control unit 110 in the case in which the vibration control is not performed, and an operation obtained by adding a vibration to the operation in the teaching is carried out by the control unit 110 in the case in which the vibration control is performed.

A procedure for inserting the guide wire 302 held by the hand 1701 into the blood vessel 301 through the automatic reproduction will be described with reference to respective different states in FIGS. 35A to 35C.

Figure 35A:
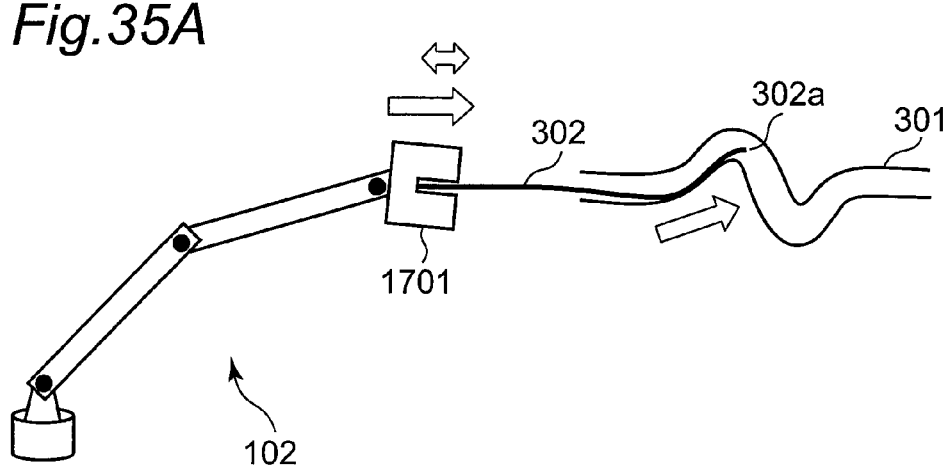
FIG. 35A is a view for explaining an operation procedure of a work for inserting a guide wire into a blood vessel (in automatic reproduction) in the robot according to the second embodiment of the present disclosure.

FIG. 35A shows a time that reproduction of teaching data is started by the control unit 110. At this time, both the insertion information and the insertion member movement information are 1, and the teaching data is generated as the operation information by the operation information generating unit 109 and is reproduced by the control unit 110 while the vibration control is carried out. Since this state is the "first progress" state, the vibration has a small magnitude. Herein, the vibration control in the insertion direction is carried out. In the automatic reproduction, a person turns on the vibration control mode in the state specifying unit 2802 by using the input/output IF 111 at start of the reproduction in this example.

The "vibration control mode" is a mode for specifying whether the vibration control is to be carried out or not in the state specifying unit 2802. If it is decided that the vibration control mode is ON in the state specifying unit 2802, the state specifying unit 2802 specifies whether the vibration control is to be carried out or not. If it is decided that the vibration control mode is OFF in the state specifying unit 2802, however, a mode for performing no vibration control is set. The state specifying unit 2802 specifies that the vibration control is not to be carried out even when a condition for performing the vibration control is satisfied (in other words, the control information is set to be 0 and the vibration information is set to be 0 as the state information in the state specifying unit 2802). In the automatic reproduction, the state specifying unit 2802 decides that the vibration control mode is ON at the start of the reproduction. However, the manipulator can also input a timing for turning ON the vibration control mode to the state specifying unit 2802 by using the input/output IF 111.

Figure 35B:
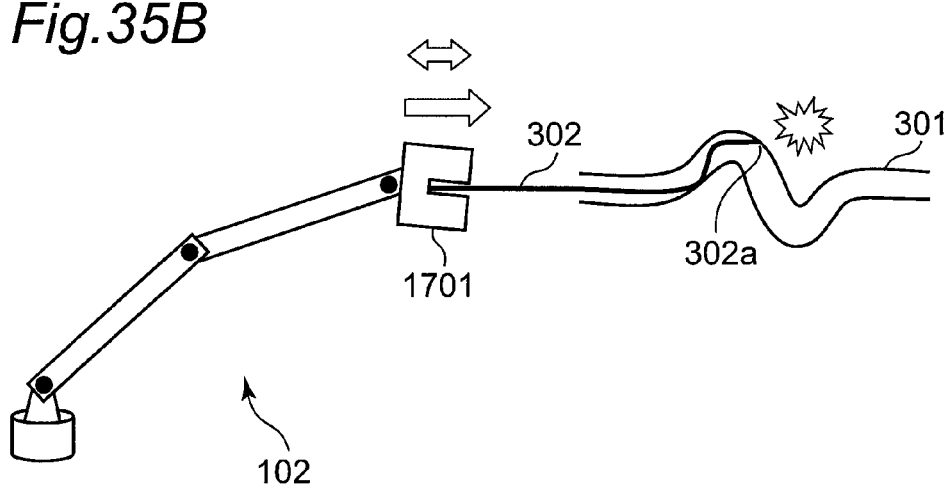
FIG. 35B is a view for explaining the operation procedure of the work for inserting the guide wire into the blood vessel (in the automatic reproduction) in the robot according to the second embodiment of the present disclosure.

Furthermore, FIG. 35B shows a time that the tip 302a of the guide wire 302 is gotten stuck in the blood vessel 301 and the movement of the tip 302a is thus stopped during the reproduction of the teaching data through the control unit 110. At this time, the insertion information is 1 and the insertion member movement information is 0, and the vibration control is continued by the control unit 110. In other words, when the state information in which the insertion information is 1, the insertion member movement information is 0, and the control information is 1 is input from the state specifying unit 2802 to the operation information generating unit 109, and the operation information for continuously carrying out the vibration control is generated by the operation information generating unit 109 based on the state information, the vibration control is consecutively performed based on the operation information by the control unit 110. At this time, the state makes a transition from the "first progress" state to the "first stop" state, and the magnitude of the vibration is increased by the state specifying unit 2802.

Figure 35C:
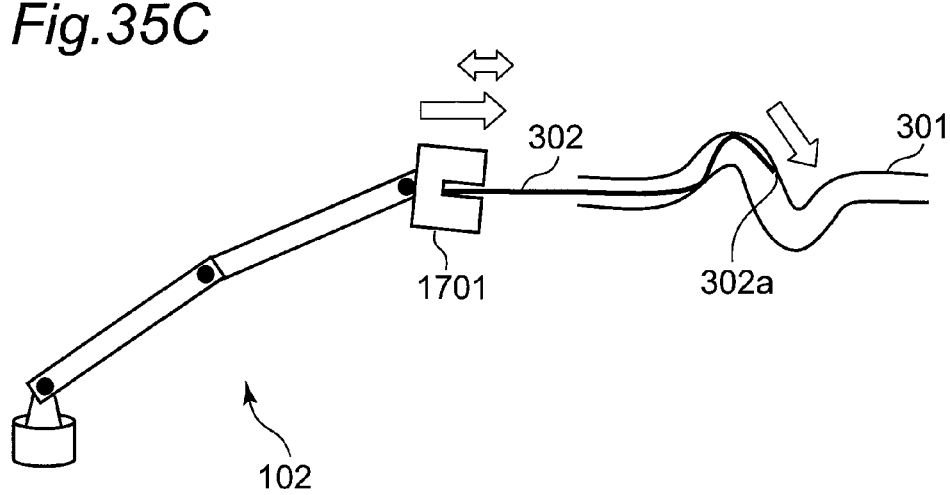
FIG. 35C is a view for explaining the operation procedure of the work for inserting the guide wire into the blood vessel (in the automatic reproduction) in the robot according to the second embodiment of the present disclosure.

On the other hand, FIG. 35C shows a time that the getting-stuck of the tip 302a of the guide wire 302 can be removed and the tip 302a can be moved as a result of the execution of the vibration control by the control unit 110 during the reproduction of the teaching data through the control unit 110. Herein, both the insertion information and the insertion member movement information are 1, the magnitude of the vibration in the vibration control through the control unit 110 is reduced by the state specifying unit 2802 (the magnitude of the vibration in FIG. 35A), and the vibration control is continuously carried out by the control unit 110. In the case in which the getting-stuck of the tip 302a of the guide wire 302 cannot be removed by the vibration control carried out in FIG. 35B so that both the insertion information and the insertion member movement information are 0, the magnitude of the vibration can further be increased by the state specifying unit 2802 so that the vibration control is continuously carried out by the control unit 110.

As described above, in the automatic reproduction, the vibration control is carried out by the control unit 110, thereby removing the getting-stuck of the tip 302a of the guide wire 302.

<Explanation in Manipulation>

As shown in FIGS. 36A to 36D, a manipulating method in the manipulation is taken as an example in which the robot arm 102 is manipulated by a hand 2001 of the manipulator by the same method as that in the case of FIGS. 20A to 20D.

In the manipulation, moreover, the manipulator can input ON or OFF of the vibration control mode to the state specifying unit 2802 by using the input/output IF 111. The manipulator can also set the state specifying unit 2802 to turn ON the vibration control mode at the start of the manipulation.

Figure 36A:
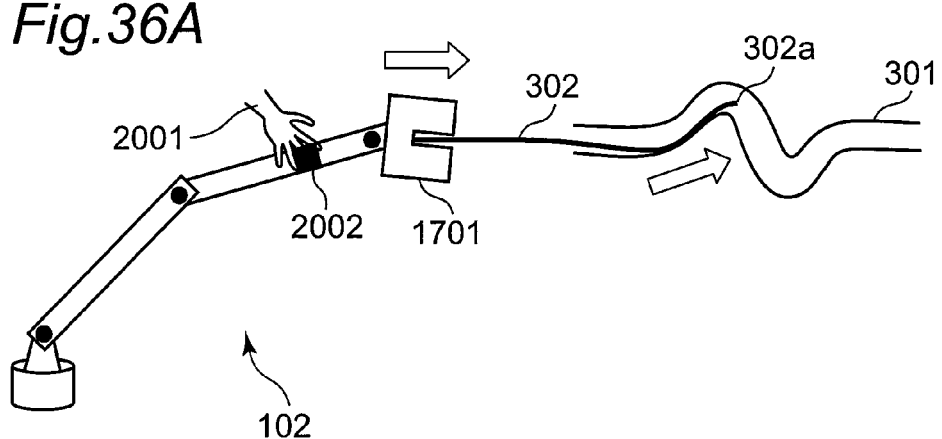
FIG. 36A is a view for explaining the operation procedure of the work for inserting a guide wire into a blood vessel (in manipulation) in the robot according to the second embodiment of the present disclosure.

FIG. 36A shows a time that the hand 2001 of the manipulator starts the manipulation of the robot arm 102. At this time, the vibration control mode is OFF and this state is the "first progress" state in which both the insertion information and insertion member movement information are 1. However, the vibration control is not carried out but an operation according to the manipulation of the hand 2001 of the manipulator is carried out. In other words, when the state information in which the insertion information is 1, the insertion member movement information is 1, and the control information is 0 is input from the state specifying unit 2802 to the operation information generating unit 109 and operation information having no vibration control is generated by the operation information generating unit 109 based on the state information, the operation is started without the vibration control based on the operation information by the control unit 110.

Figure 36B:
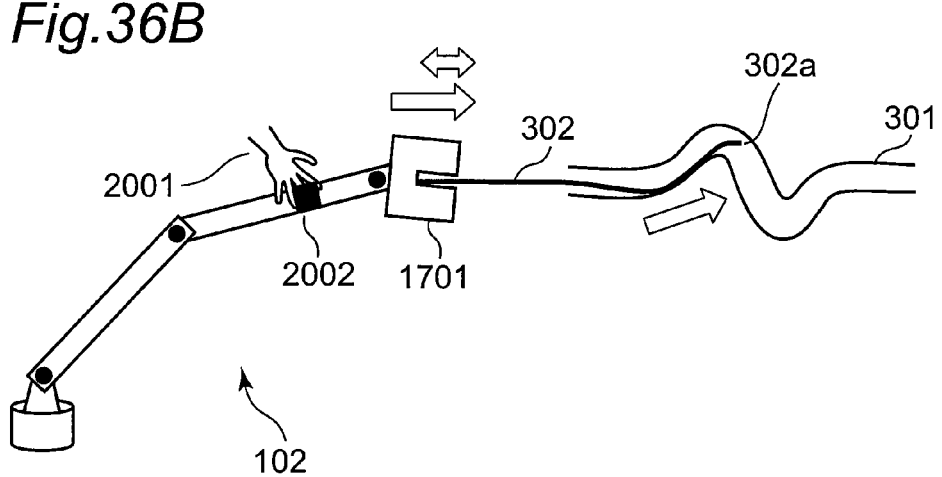
FIG. 36B is a view for explaining the operation procedure of the work for inserting the guide wire into the blood vessel (in the manipulation) in the robot according to the second embodiment of the present disclosure.

Next, FIG. 36B shows a time that the manipulator turns ON the vibration control mode during the manipulation of the robot arm 102 through the hand 2001 of the manipulator. There is the "first progress" state in which both the insertion information and the insertion member movement information are 1, and the vibration control is started by the control unit 110. In other words, when the state information in which the insertion information is 1, the insertion member movement information is 1, and the control information is 1 is input from the state specifying unit 2802 to the operation information generating unit 109, and the operation information for starting the vibration control is generated by the operation information generating unit 109 based on the state information, the vibration control is started based on the operation information by the control unit 110. This state is the "first progress" state. For this reason, the vibration has a small magnitude by the state specifying unit 2802. Herein, the vibration control in the insertion direction is carried out over the guide wire 302 by the control unit 110.

Figure 36C:
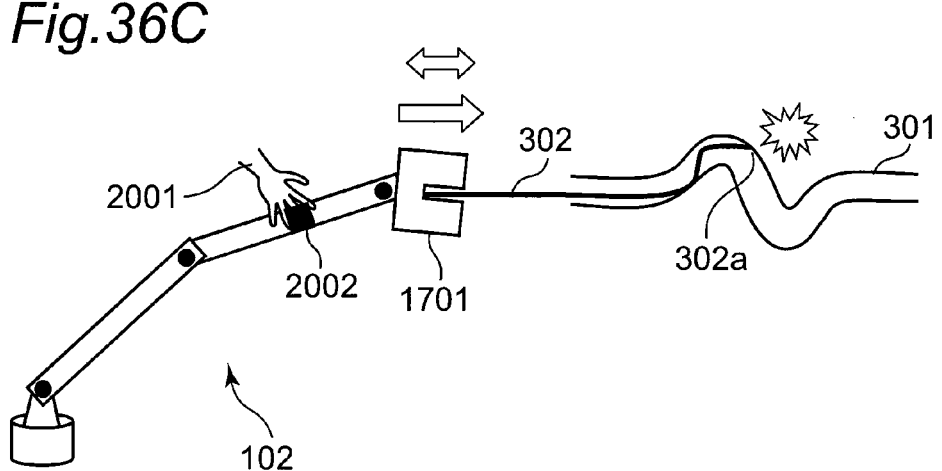
FIG. 36C is a view for explaining the operation procedure of the work for inserting the guide wire into the blood vessel (in the manipulation) in the robot according to the second embodiment of the present disclosure.

On the other hand, FIG. 36C shows a time that the tip 302a of the guide wire 302 is gotten stuck in the blood vessel 301 so that the movement of the tip 302a is stopped during the manipulation of the robot arm 102 through the hand 2001 of the manipulator. At this time, there is the "first stop" state in which the insertion information is 1 and the insertion member movement information is 0, and the vibration control is continuously carried out by the control unit 110. In other words, when the state information in which the insertion information is 1, the insertion member movement information is 0, and the control information is 1 is input from the state specifying unit 2802 to the operation information generating unit 109 and operation information for continuously carrying out the vibration control is generated by the operation information generating unit 109 based on the state information, the vibration control is continuously performed based on the operation information by the control unit 110. At this time, there is brought a state making a transition from the "first progress" state to the "first stop" state, and the magnitude of the vibration is increased by the state specifying unit 2802.

Figure 36D:
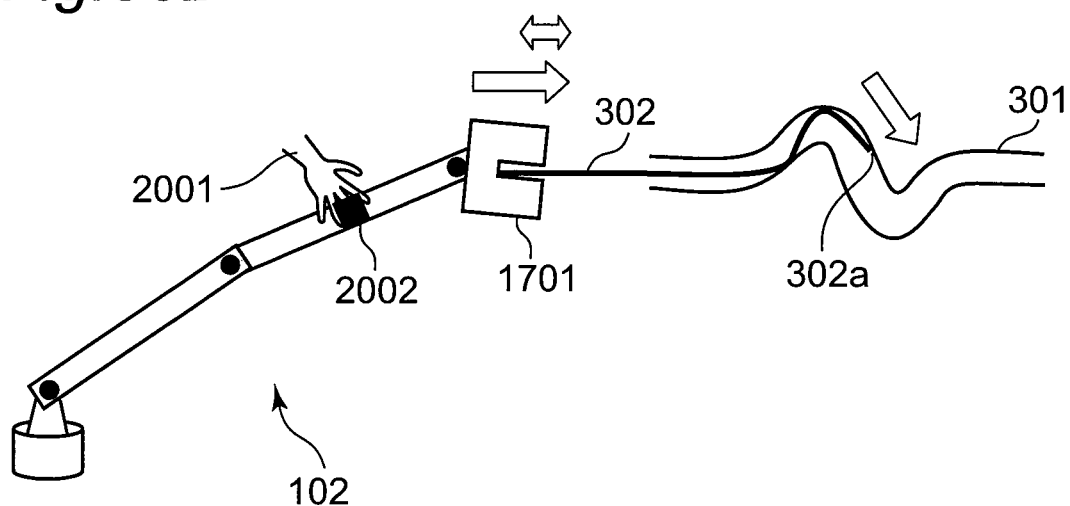
FIG. 36D is a view for explaining the operation procedure of the work for inserting the guide wire into the blood vessel (in the manipulation) in the robot according to the second embodiment of the present disclosure.

FIG. 36D shows a time that the getting-stuck of the tip 302a of the guide wire 302 can be removed and the tip 302a can be moved as a result of the execution of the vibration control during the manipulation of the robot arm 102 through the hand 2001 of the manipulator. Herein, there is the "first progress" state in which both the insertion information and the insertion member movement information are 1, the state specifying unit 2802 reduces the magnitude of the vibration in the vibration control of the control unit 110 (the magnitude of the vibration in FIG. 36B), and the vibration control is continuously carried out by the control unit 110. In the case in which the getting-stuck of the tip 302a of the guide wire 302 cannot be removed by the vibration control carried out in FIG. 36C and there is brought the "second stop" state in which both the insertion information and the insertion member movement information are 0, the magnitude of the vibration is further increased to continuously carry out the vibration control by the state specifying unit 2802.

As described above, the vibration control is carried out by the control unit 110 to remove the getting-stuck of the tip 302a of the guide wire 302 in the manipulation.

Figure 37:
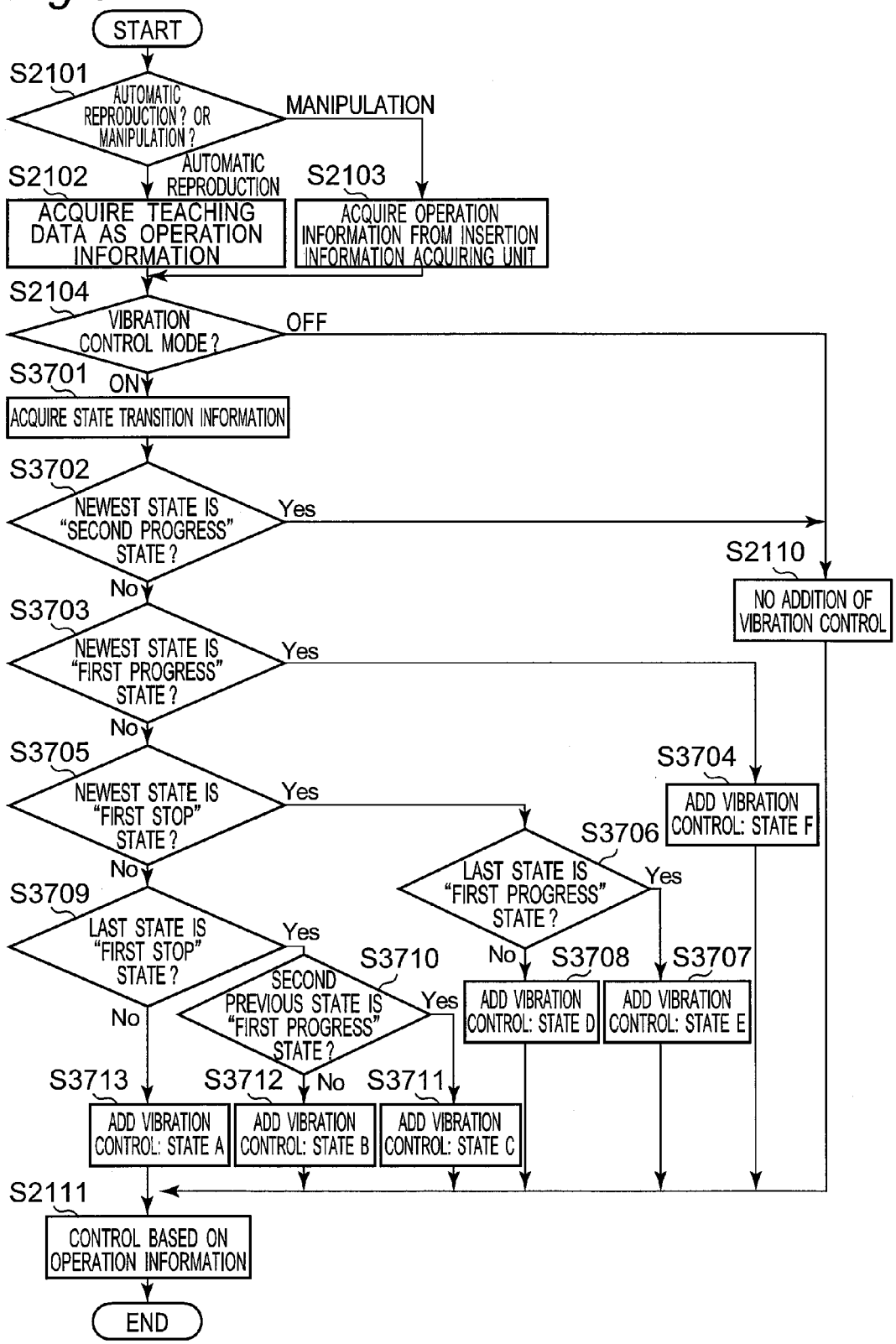
FIG. 37 is a flowchart in a manipulation procedure of a control apparatus for the robot according to the second embodiment of the present disclosure.

A procedure for manipulating the control apparatus 103B for the robot arm 102 according to the second embodiment will be described with reference to a flowchart of FIG. 37.

First of all, in step S2101, the manipulating procedure proceeds to step S2102 if the mode input from the input/output IF 111 to the state specifying unit 2802 is the automatic reproduction mode, and the manipulating procedure proceeds to step S2103 if the input mode is the manipulation mode, in the input/output IF 111.

In step S2102, the teaching data stored in the internal storage unit of the operation information generating unit 109 is set to be the operation information in the operation information generating unit 109, and the manipulating procedure proceeds to step S2104.

In step S2103, information acquired by the insertion information acquiring unit 106 is set to be the operation information in the operation information generating unit 109, and the manipulating procedure proceeds to step S2104.

In step S2104, the state specifying unit 2802 decides whether the vibration control mode is ON or OFF in the state specifying unit 2802. If the state specifying unit 2802 decides that the vibration control mode is ON, the manipulating procedure proceeds to step S3701. If the state specifying unit 2802 decides that the vibration control mode is OFF, the manipulating procedure proceeds to step S2110. The manipulator selects the ON/OFF of the vibration control mode based on the information input to the state specifying unit 2802 by using the input/output IF 111.

In step S3701, the state specifying unit 2802 acquires the state transition information by the state transition storage unit 2801, and the manipulating procedure proceeds to step S3702.

In step S3702, the manipulating procedure proceeds to step S2110 if the state specifying unit 2802 decides that the newest state in the state transition information acquired from the state transition storage unit 2801 is the "second progress" state, and the manipulating procedure proceeds to step S3703 if the state specifying unit 2802 decides that the newest state is not the "second progress" state.

In step S2110, the state specifying unit 2802 generates the state information for carrying out no vibration control, and the manipulating procedure proceeds to step S2111.

In step S3703, the manipulating procedure proceeds to step S3704 if the state specifying unit 2802 decides that the newest state in the state transition information acquired from the state transition storage unit 2801 is the "first progress" state, and the manipulating procedure proceeds to step S3705 if the state specifying unit 2802 decides that the newest state is not the "first progress" state.

In step S3704, the state specifying unit 2802 generates the state information for carrying out the vibration control, and the manipulating procedure proceeds to step S2111. Herein, the magnitude of the vibration is made the smallest as compared with the other cases (a state F in FIG. 37).

In step S3705, the manipulating procedure proceeds to step S3706 if the state specifying unit 2802 decides that the newest state in the state transition information acquired from the state transition storage unit 2801 is the "first stop" state, and the manipulating procedure proceeds to step S3709 if the state specifying unit 2802 decides that the newest state is not the "first stop" state.

In step S3706, the manipulating procedure proceeds to step S3707 if the state specifying unit 2802 decides that a last state from the newest state in the state transition information acquired from the state transition storage unit 2801 is the "first progress" state, and the manipulating procedure proceeds to step S3708 if the state specifying unit 2802 decides that the last state is not the "first progress" state.

In step S3707, the state specifying unit 2802 generates the state information for carrying out the vibration control, and the manipulating procedure proceeds to step S2111. Herein, the magnitude of the vibration is made greater than that in the case of step S3704 and is made smaller than that in the case of step S3708 (a state E in FIG. 37).

In step S3708, the state specifying unit 2802 generates the state information for carrying out the vibration control, and the manipulating procedure proceeds to step S2111. Herein, the magnitude of the vibration is made greater than that in the case of step S3707 and is made smaller than that in the case of step S3711 (a state D in FIG. 37).

In step S3709, the manipulating procedure proceeds to step S3710 if the state specifying unit 2802 decides that a last state from the newest state in the state transition information acquired from the state transition storage unit 2801 is the "first stop" state, and the manipulating procedure proceeds to step S3713 if the state specifying unit 2802 decides that the last state is not the "first stop" state.

In step S3710, the manipulating procedure proceeds to step S3711 if the state specifying unit 2802 decides that a second previous state to the newest state in the state transition information acquired from the state transition storage unit 2801 is the "first progress" state, and the manipulating procedure proceeds to step S3712 if the state specifying unit 2802 decides that the second previous state is not the "first progress" state.

In step S3711, the state specifying unit 2802 generates the state information for carrying out the vibration control, and the manipulating procedure proceeds to step S2111. Herein, the magnitude of the vibration is made greater than that in the case of step S3708 and is made smaller than that in the case of step S3712 (a state C in FIG. 37).

In step S3712, the state specifying unit 2802 generates the state information for carrying out the vibration control, and the manipulating procedure proceeds to step S2111. Herein, the magnitude of the vibration is made greater than that in the case of step S3711 and is made smaller than that in the case of step S3713 (a state B in FIG. 37).

In step S3713, the state specifying unit 2802 generates the state information for carrying out the vibration control, and the manipulating procedure proceeds to step S2111. Herein, the magnitude of the vibration is made the greatest as compared with the others (a state A in FIG. 37).

In step S2111, the operation information generating unit 109 acquires the state information from the state specifying unit 2802, and adds the operation information for the vibration control to generate operation information if the vibration control is to be carried out. The operation information generating unit 109 generates the operation information directly from the acquired operation information if the vibration control is not to be carried out. The operation information is output from the operation information generating unit 109 to the control unit 110, and the operation of the robot arm 102 is controlled based on the operation information acquired in the control unit 110.

Effect of the Second Embodiment

In the work for inserting the insertion member such as the guide wire 302, the vibration control is carried out in a small flexure state and the magnitude of the vibration is regulated depending on the transition of the state by the state specifying unit 2802. Consequently, it is possible to reduce a load to be applied to the blood vessel 301 as compared with the first embodiment. Thus, it is possible to remove getting-stuck with a vibration having smaller force applied to the blood vessel 301.

Third Embodiment

Figure 38:
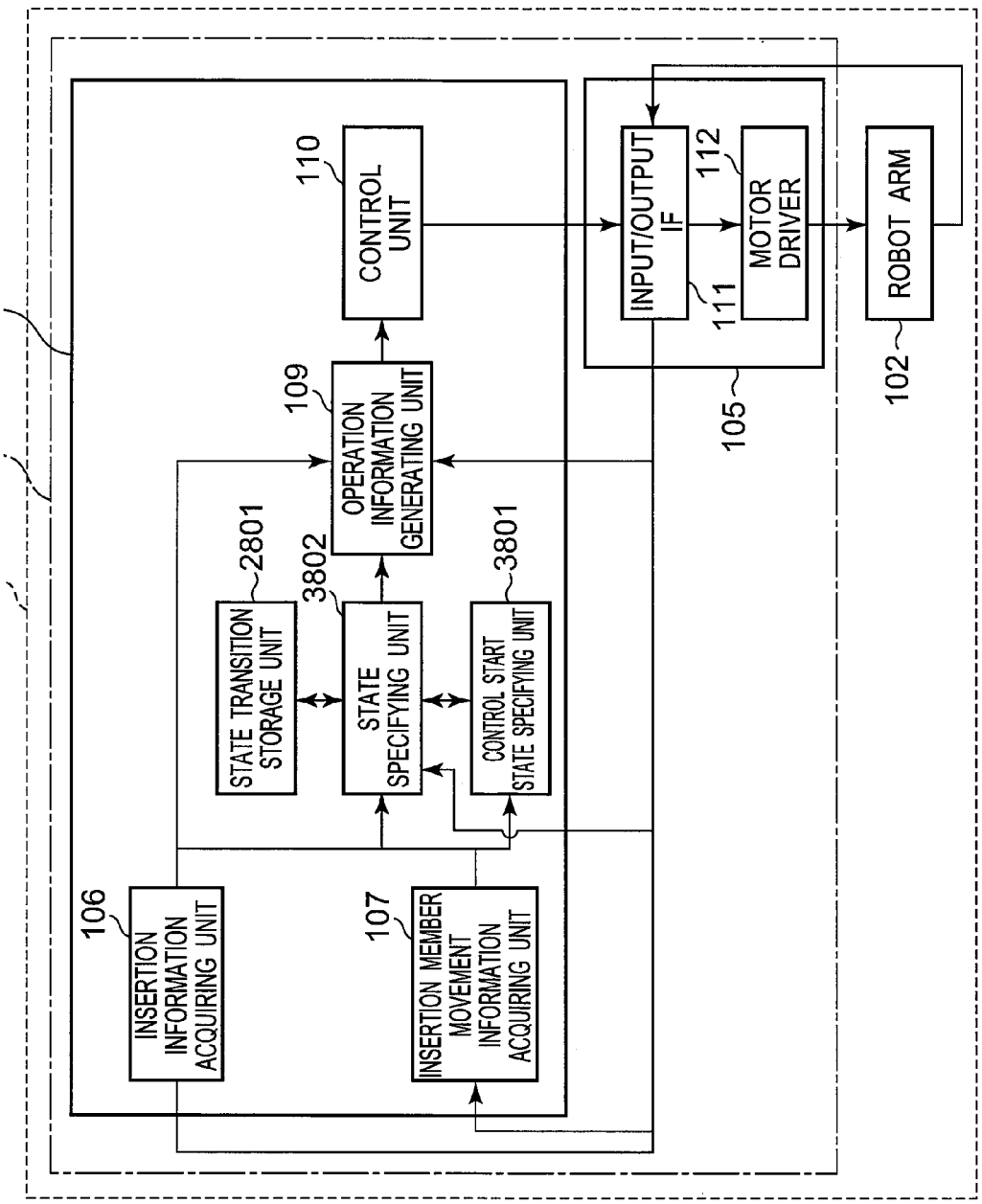
FIG. 38 is a block diagram showing a robot arm in a robot according to a third embodiment of the present disclosure.

FIG. 38 is a block diagram showing a robot 101C according to an example of an insertion apparatus in accordance with a third embodiment of the present disclosure. A control apparatus 103C of the robot arm 102 according to an example of a control apparatus of an insertion apparatus in accordance with the third embodiment of the present disclosure has a feature that a control apparatus body unit 104C is provided with a state specifying unit 3802 and a control start state specifying unit 3801. Since the robot arm 102; the peripheral apparatus 105; and the insertion information acquiring unit 106, the insertion member movement information acquiring unit 107, the operation information generating unit 109, the control unit 110, and the state transition storage unit 2801 in the control apparatus body unit 104C of the control apparatus 103C in the robot 101C according to the third embodiment of the present disclosure are the same as those in the second embodiment, they have common reference numerals and the description of common parts are omitted, and only different parts will be explained below in detail.

The control start state specifying unit 3801 acquires insertion member movement information and time information from the insertion member movement information acquiring unit 107, acquires state information and time information from the state specifying unit 3802, generates control start state information, and outputs the generated control start state information together with the time information to the state specifying unit 3802.

The control start state information has a value of 0 or 1. If the value is 0, it is indicated that the tip of the insertion member is not moved at the start of control. If the value is 1, it is indicated that the tip of the insertion member is moved at the start of the control.

At the start of the vibration control, the control start state specifying unit 3801 outputs 1 as the control start state information if the tip of the insertion member is moved and outputs 0 as the control start state information if the tip is not moved. If it is decided by the control start state specifying unit 3801 that the vibration control is stopped based on the state information transmitted from the state specifying unit 3802, 0 is output as the control start state information from the control start state specifying unit 3801.

Figure 39:
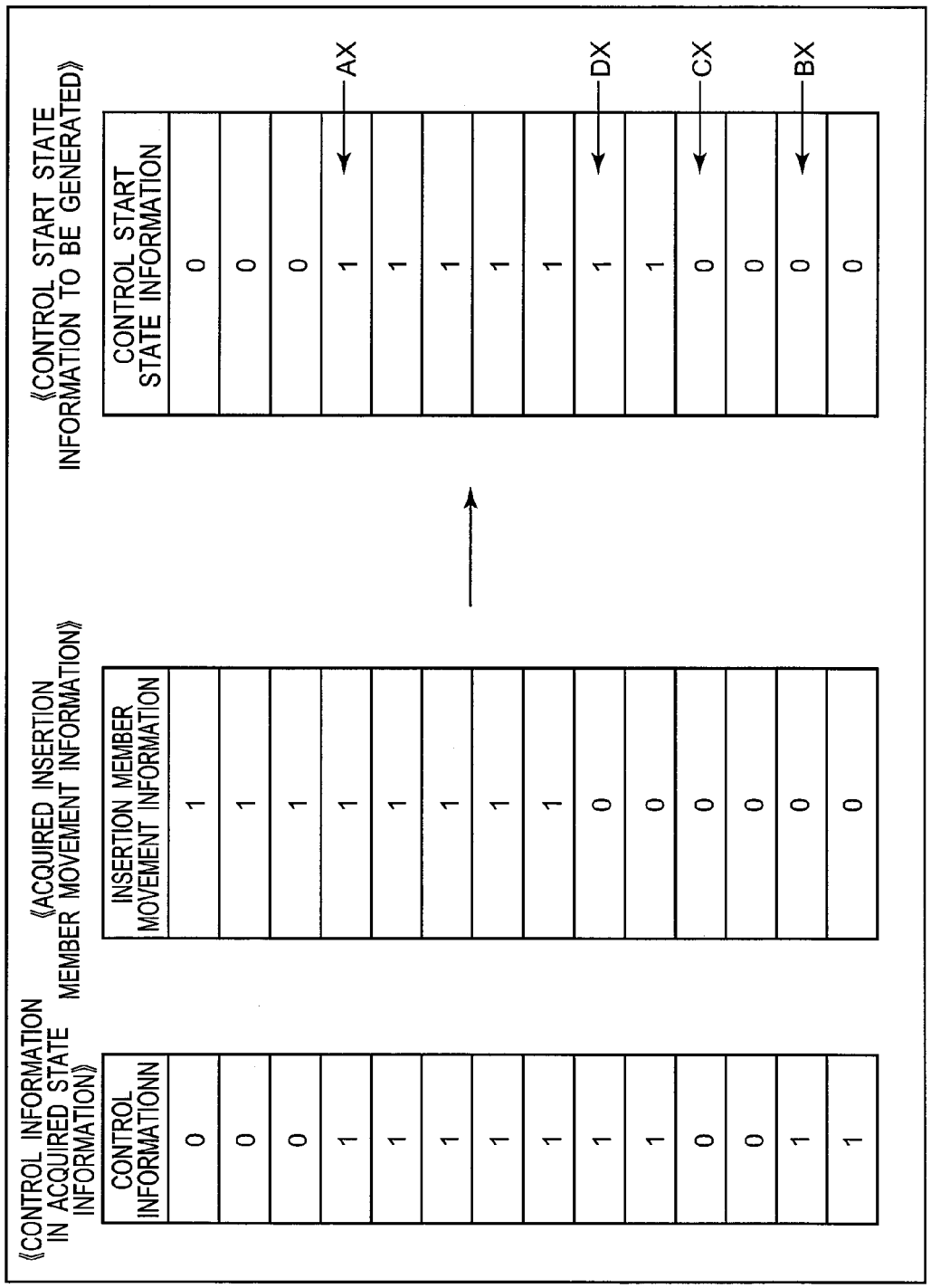
FIG. 39 is a view for explaining a method of generating control start state information in the robot according to the third embodiment of the present disclosure.

A method of generating the control start state information in the control start state specifying unit 3801 will be described with reference to FIG. 39.

A condition for outputting the control start state information of 1 from the control start state specifying unit 3801 is that the insertion member movement information is 1 when the control information is changed from 0 to 1. At a time of the symbol AX in FIG. 39, the insertion member movement information is 1 when the control information is changed from 0 to 1. Consequently, the control start state information is 1. At a time of the symbol BX in FIG. 39, the insertion member movement information is 0 when the control information is changed from 0 to 1. Consequently, the control start state information is maintained to be 0.

When outputting 1 as the control start state information, the control start state specifying unit 3801 continuously outputs 1 as the control start state information until the ending condition is satisfied. The ending condition is that the control information is changed from 1 to 0. At a time of the symbol CX in FIG. 39, the control information is changed from 1 to 0. Therefore, the control start state information is 0. At a time of the symbol DX in FIG. 39, the insertion member movement information is changed from 1 to 0. However, the control information is maintained to be 1. Therefore, the control start state information is maintained to be 1.

The control start state specifying unit 3801 outputs the generated control start state information and time information to the state specifying unit 3802.

The state specifying unit 3802 is provided in the control apparatus body unit 104C in place of the state specifying unit 2802, and has a function for varying the magnitude of a vibration based on the control start state information acquired from the control start state specifying unit 3801, in addition to the function of the state specifying unit 2802 according to the second embodiment. The additional function will be described below.

Figure 40:
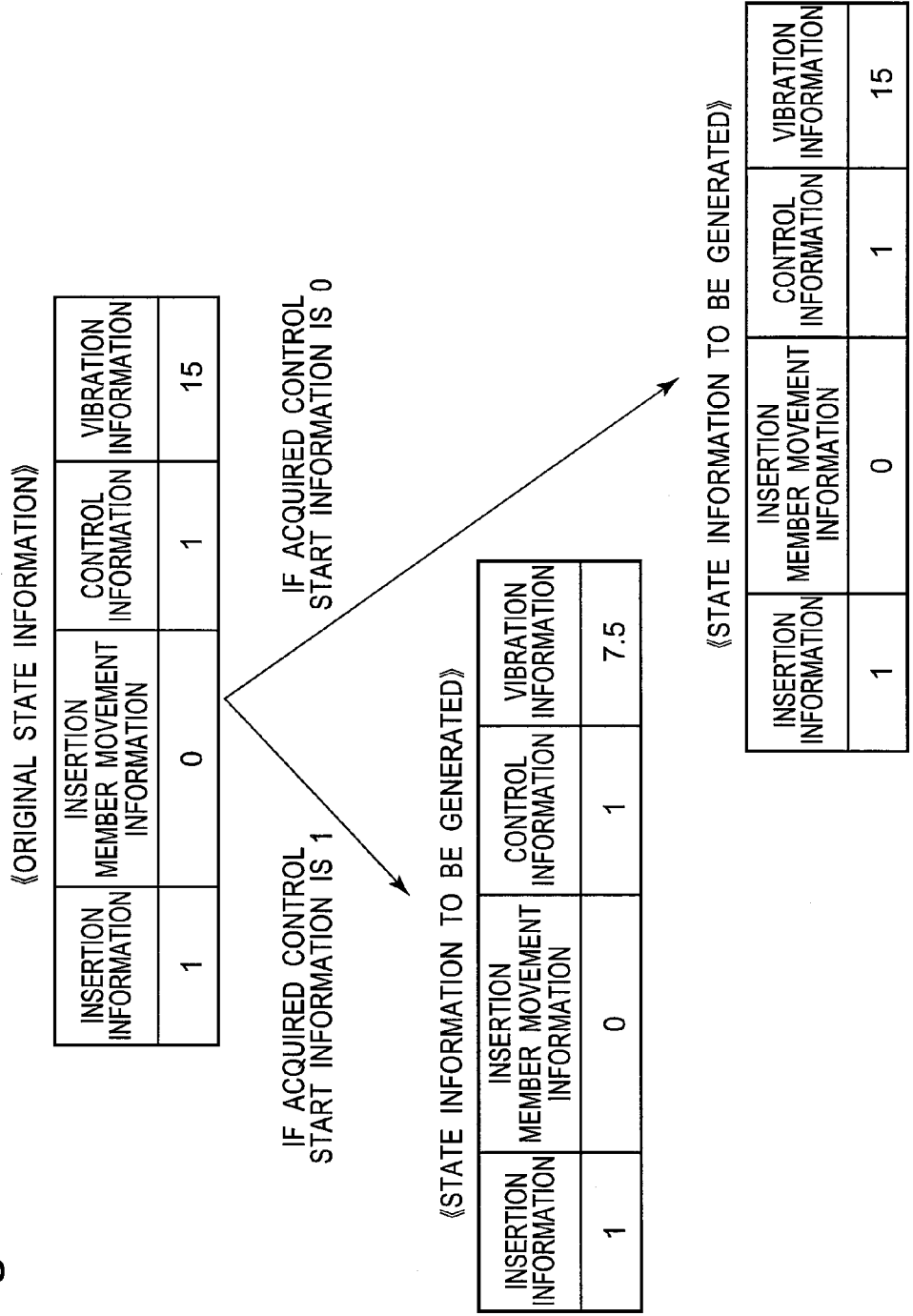
FIG. 40 is a view for explaining a method of generating state information in the robot according to the third embodiment of the present disclosure.

In the case in which the control start state information acquired from the control start state specifying unit 3801 is 1, the state specifying unit 3802 reduces the value of the vibration information in the state information. Specifically, the state specifying unit 3802 multiplies the value of the vibration information by a constant, thereby reducing the value. The constant is set to be a value which is greater than 0 and is smaller than 1 (for example, 0.5). In the case in which the control start state information acquired from the control start state specifying unit 3801 is 0, the state specifying unit 3802 performs nothing. A specific example will be shown in FIG. 40.

The state specifying unit 3802 outputs the generated state information together with the time information to the operation information generating unit 109.

In the state specifying unit 3802, the magnitude of the vibration is reduced more greatly in the case in which the insertion member is moved at the start of the vibration control than the case in which the insertion member is not moved. This can be explained based on a result obtained by executing an experiment which will be described below.

In the experiment in which the wire 1102 is inserted into the tube 1101 as described with referenced to FIG. 24, the vibration control was started in the vibration start position indicated by the symbol C of FIG. 24. The vibration start position represents a "first progress" state in which the position of the tip 1102a of the wire 1102 is moved and the position of the hand 1701 is also moved as shown in FIG. 25C. The experiment was carried out by two starting methods, that is, in the case in which the vibration control is started in the position indicated by the symbol C with the tip 1102a of the wire 1102 moved at the start of the vibration control, and the case in which the movement of the tip 1102a of the wire 1102 is once stopped in the position indicated by the symbol C and the vibration control is then started. FIG. 41 shows a result of the experiment. In FIG. 41, at the start of the vibration control, the case in which the tip 1102a of the wire 1102 is moved represents "movement", and the case in which the tip 1102a of the wire 1102 is not moved but stopped represents "stop". An insertion distance (mm) indicates an inserted distance at which the wire 1102 is inserted into the tube 1101, and a longer distance represents that the wire 1102 is inserted into a further inner part. A magnitude (N) of force indicates a value acquired by the force sensor 1103 at a time that the tip 1102a of the wire 1102 passes through a position placed immediately forward a position A, and a smaller magnitude represents that the passage can be carried out by smaller force. From FIG. 41, it is apparent that the insertion distance is longer and the magnitude of the force is smaller in the case in which the tip 1102a of the wire 1102 is moved at the start of the vibration control than in the case in which the tip 1102a of the wire 1102 is stopped at the start of the vibration control. This indicates that the passage through the same position can be carried out with a smaller vibration in the case in which the vibration control is started with the tip 1102a of the wire 1102 moved than in the case in which the vibration control is started with the tip 1102a of the wire 1102 stopped.

<Explanation of Operation Procedure>

A procedure for inserting the insertion member through the insertion apparatus according to the third embodiment will be described for the automatic reproduction and the manipulation. Referring to the selection of the automatic reproduction mode or the manipulation mode, a manipulator can input information about which mode is to be selected, to the operation information generating unit 109 by using the input/output IF 111.

<Explanation of Automatic Reproduction>

In the automatic reproduction, the operation of the robot arm 102 is controlled by the control unit 110 based on the operation information about the robot arm 102 in the teaching which is stored in the internal storage unit of the operation information generating unit 109. Under the control of the control unit 110, the operation in the teaching is carried out by the control unit 110 in the case in which the vibration control is not performed, and an operation obtained by adding a vibration to the operation in the teaching is carried out by the control unit 110 in the case in which the vibration control is performed.

A procedure for inserting the guide wire 302 held by the hand 1701 into the blood vessel 301 through the automatic reproduction will be described with reference to respective different states in FIGS. 42A to 42C.

FIG. 42A shows a time that reproduction of teaching data is started by the control unit 110. At this time, both the insertion information and the insertion member movement information are 1, and the teaching data is generated as the operation information by the operation information generating unit 109 and is reproduced by the control unit 110 while the vibration control is carried out. This state is the "first progress" state. For this reason, the magnitude of the vibration is reduced by the state specifying unit 3802. Moreover, the insertion member movement information is 1 when the vibration is started. For this reason, the magnitude of the subsequent vibration is reduced by the state specifying unit 3802. Thus, the third embodiment has a feature that the magnitude of the vibration is reduced by the state specifying unit 3802 depending on the insertion member movement information at the start of the vibration control. Herein, the vibration control in the insertion direction is carried out. In the automatic reproduction, at the start of the reproduction, the vibration control mode is ON. The vibration control mode is a mode for deciding whether the vibration control is to be carried out or not in the state specifying unit 3802. If it is decided that the vibration control mode is ON in the state specifying unit 3802, the state specifying unit 3802 decides whether the vibration control is to be carried out or not. If it is decided that the vibration control mode is OFF in the state specifying unit 3802, however, a mode for performing no vibration control is set. The state specifying unit 3802 decides that the vibration control is not to be carried out even when a condition for performing the vibration control is satisfied (in other words, the control information is set to be 0 and the vibration information is set to be 0 as the state information in the state specifying unit 3802). In the automatic reproduction, the vibration control mode is ON at the start of the reproduction. However, the manipulator can also input a timing for turning ON the vibration control mode to the state specifying unit 3802 by using the input/output IF 111.

Furthermore, FIG. 42B shows a time that the tip 302a of the guide wire 302 is gotten stuck in the blood vessel 301 and the movement of the tip 302a is thus stopped during the reproduction of the teaching data through the control unit 110. At this time, the insertion information is 1 and the insertion member movement information is 0, and the vibration control is continued by the control unit 110. In other words, when the state information in which the insertion information is 1, the insertion member movement information is 0, and the control information is 1 is input from the state specifying unit 3802 to the operation information generating unit 109, and the operation information for continuously carrying out the vibration control is generated by the operation information generating unit 109 based on the state information, the vibration control is consecutively performed based on the operation information by the control unit 110. At this time, the state makes a transition from the "first progress" state to the "first stop" state, and the magnitude of the vibration is increased. The magnitude is obtained through multiplication, by a constant (for example, 0.5), of the magnitude of the vibration in the case of FIG. 35B according to the second embodiment.

Figure 42C:
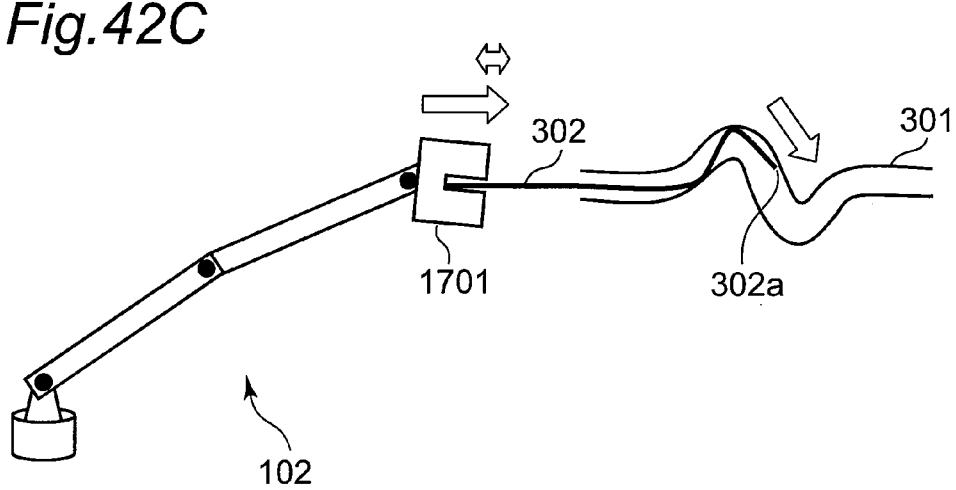
FIG. 42C is a view for explaining the operation procedure of the work for inserting the guide wire into the blood vessel (in the automatic reproduction) in the robot according to the third embodiment of the present disclosure.

On the other hand, FIG. 42C shows a time that the getting-stuck of the tip 302a of the guide wire 302 can be removed and the tip 302a can be moved as a result of the execution of the vibration control by the control unit 110 during the reproduction of the teaching data through the control unit 110. Herein, both the insertion information and the insertion member movement information are 1, the magnitude of the vibration in the vibration control through the control unit 110 is reduced (the magnitude of the vibration in FIG. 42A), and the vibration control is continuously carried out by the control unit 110. At this time, the magnitude of the vibration is obtained through multiplication, by a constant (for example, 0.5), of the magnitude of the vibration in the case of FIG. 35O according to the second embodiment. In the case in which the getting-stuck of the tip 302a of the guide wire 302 cannot be removed by the vibration control carried out in FIG. 42B so that both the insertion information and the insertion member movement information are 0, the magnitude of the vibration can further be increased by the state specifying unit 3802 so that the vibration control is continuously carried out by the control unit 110.

As described above, in the automatic reproduction, the vibration control is carried out by the control unit 110, thereby removing the getting-stuck of the tip of the guide wire 302.

<Explanation in Manipulation>

As shown in FIGS. 43A to 43D, a manipulating method in the manipulation is taken as an example in which the robot arm 102 is manipulated by a hand 2001 of the manipulator by the same method as that in the case of FIGS. 20A to 20D.

In the manipulation, moreover, the manipulator can input ON or OFF of the vibration control mode to the state specifying unit 3802 by using the input/output IF 111. The manipulator can also set the state specifying unit 3802 to turn ON the vibration control mode to at the start of the manipulation.

Figure 43A:
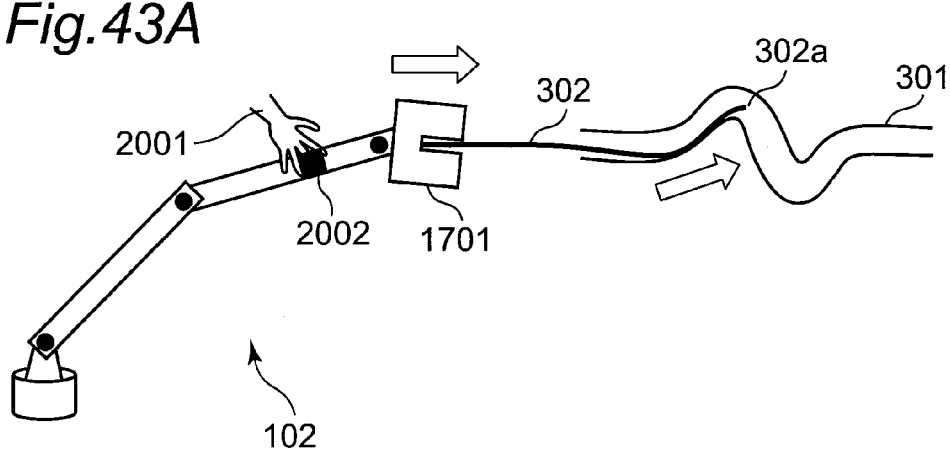
FIG. 43A is a view for explaining the operation procedure of the work for inserting a guide wire into a blood vessel (in manipulation) in the robot according to the third embodiment of the present disclosure.

FIG. 43A shows a time that the hand 2001 of the manipulator starts the manipulation of the robot arm 102. At this time, the vibration control mode is OFF and this state is the "first progress" state in which both the insertion information and insertion member movement information are 1. However, the vibration control is not carried out but an operation according to the manipulation of the hand 2001 of the manipulator is carried out. In other words, when the state information in which the insertion information is 1, the insertion member movement information is 1, and the control information is 0 is input from the state specifying unit 3802 to the operation information generating unit 109 and operation information having no vibration control is generated by the operation information generating unit 109 based on the state information, the operation is started without the vibration control based on the operation information by the control unit 110.

Figure 43B:
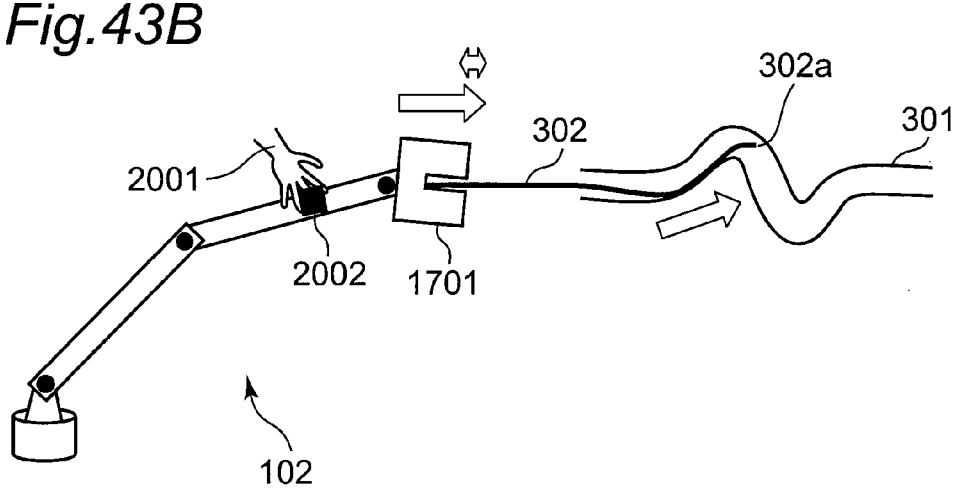
FIG. 43B is a view for explaining the operation procedure of the work for inserting the guide wire into the blood vessel (in the manipulation) in the robot according to the third embodiment of the present disclosure.

Next, FIG. 43B shows a time that the manipulator turns ON the vibration control mode during the manipulation of the robot arm 102 through the hand 2001 of the manipulator. This state is the "first progress" state in which both the insertion information and the insertion member movement information are 1, and the vibration control is started by the control unit 110. In other words, when the state information in which the insertion information is 1, the insertion member movement information is 1, and the control information is 1 is input from the state specifying unit 3802 to the operation information generating unit 109, and the operation information for starting the vibration control is generated by the operation information generating unit 109 based on the state information, the vibration control is started based on the operation information by the control unit 110. This state is the "first progress" state. For this reason, the vibration has a small magnitude. Moreover, the insertion member movement information is 1 at the start of the vibration. Therefore, the magnitude of the subsequent vibration is reduced by the state specifying unit 3802. Thus, the third embodiment has a feature that the magnitude of the vibration is reduced by the state specifying unit 3802 depending on the insertion member movement information at the start of the vibration control. Herein, the vibration control in the insertion direction is carried out over the guide wire 302 by the control unit 110. The magnitude of the vibration is obtained through multiplication, by a constant (for example, 0.5), of the magnitude of the vibration in the case of FIG. 36B according to the second embodiment.

Figure 43C:
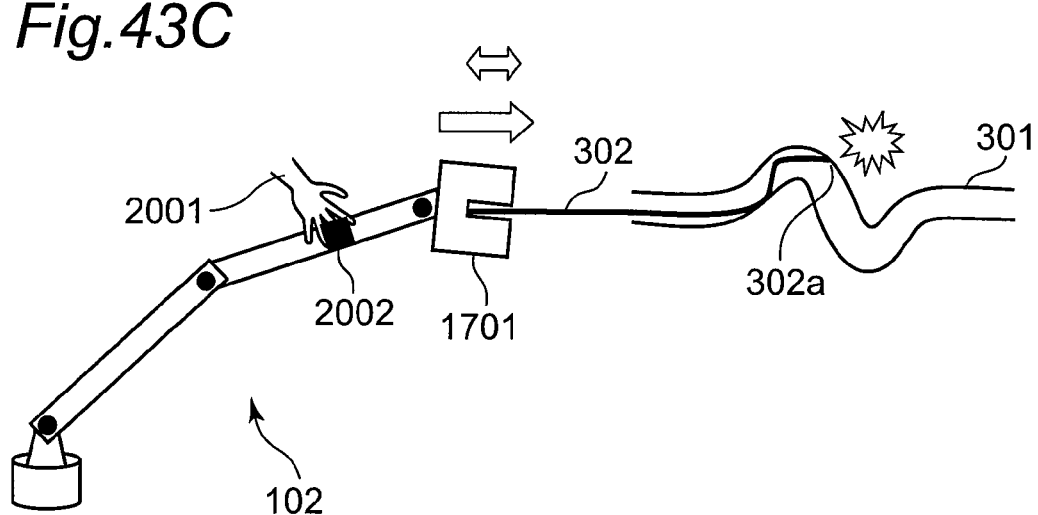
FIG. 43C is a view for explaining the operation procedure of the work for inserting the guide wire into the blood vessel (in the manipulation) in the robot according to the third embodiment of the present disclosure.

On the other hand, FIG. 43C shows a time that the tip 302a of the guide wire 302 is gotten stuck in the blood vessel 301 so that the movement of the tip 302a is stopped during the manipulation of the robot arm 102 through the hand 2001 of the manipulator. At this time, this state is the "first stop" state in which the insertion information is 1 and the insertion member movement information is 0, and the vibration control is continuously carried out by the control unit 110. In other words, when the state information in which the insertion information is 1, the insertion member movement information is 0, and the control information is 1 is input from the state specifying unit 3802 to the operation information generating unit 109 and operation information for continuously carrying out the vibration control is generated by the operation information generating unit 109 based on the control information, the vibration control is continuously performed based on the operation information by the control unit 110. At this time, there is brought a state making a transition from the "first progress" state to the "first stop" state, and the magnitude of the vibration is increased by the state specifying unit 3802. At this time, the magnitude of the vibration is obtained through multiplication, by a constant (for example, 0.5), of the magnitude of the vibration in the case of FIG. 36C according to the second embodiment.

Figure 43D:
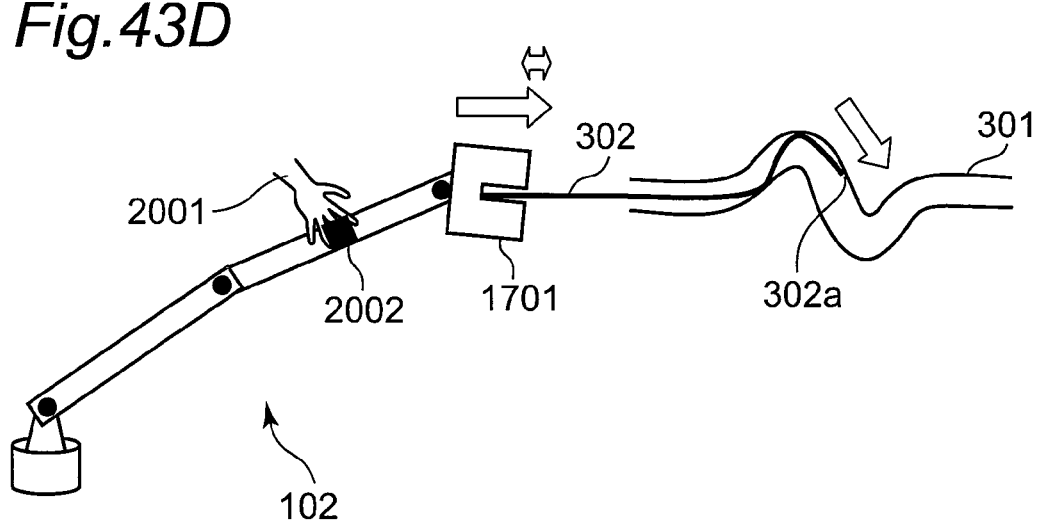
FIG. 43D is a view for explaining the operation procedure of the work for inserting the guide wire into the blood vessel (in the manipulation) in the robot according to the third embodiment of the present disclosure.

FIG. 43D shows a time that the getting-stuck of the tip 302a of the guide wire 302 can be removed and the tip 302a can be moved as a result of the execution of the vibration control during the manipulation of the robot arm 102 through the hand 2001 of the manipulator. Herein, this state is the "first progress" state in which both the insertion information and the insertion member movement information are 1, the magnitude of the vibration in the vibration control is reduced by the control unit 110 (the magnitude of the vibration in FIG. 43B), and the vibration control is continuously carried out by the control unit 110. At this time, the magnitude of the vibration is obtained through multiplication, by a constant (for example, 0.5), of the magnitude of the vibration in the case of FIG. 36D according to the second embodiment. In the case in which the getting-stuck of the tip 302a of the guide wire 302 cannot be removed by the vibration control carried out in FIG. 43C so that there is brought the "second stop" state in which both the insertion information and the insertion member movement information are 0, the magnitude of the vibration can further be increased by the state specifying unit 3802 so that the vibration control is continuously carried out by the control unit 110.

As described above, the vibration control is carried out by the control unit 110 to remove the getting-stuck of the tip 302a of the guide wire 302 in the manipulation.

Figure 44:
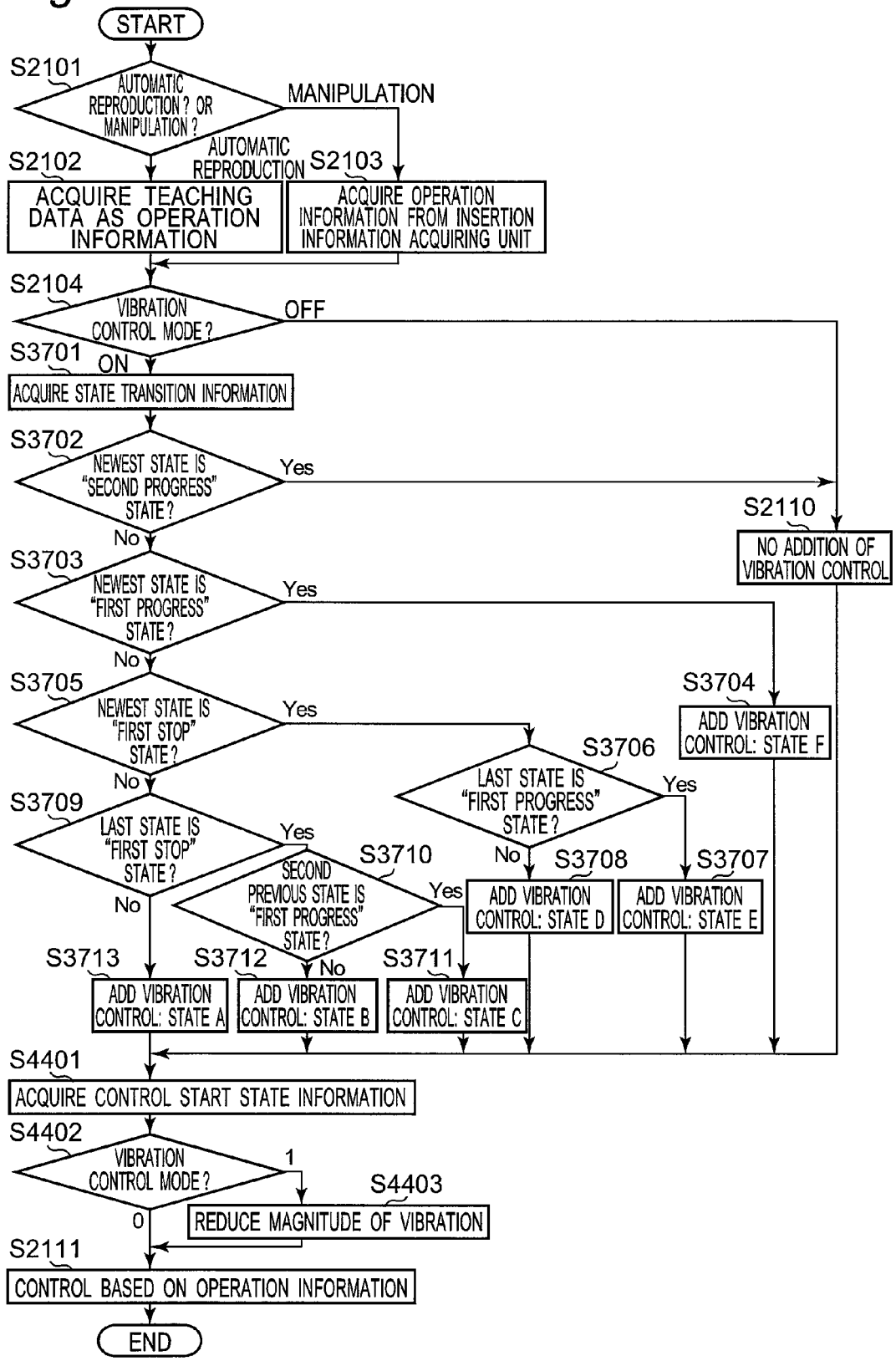
FIG. 44 is a flowchart in a manipulation procedure of a control apparatus for the robot according to the third embodiment of the present disclosure.

A procedure for manipulating the control apparatus 103C for the robot arm 102 according to the third embodiment will be described with reference to a flowchart of FIG. 44.

First of all, in step S2101, the manipulating procedure proceeds to step S2102 if the mode input from the input/output IF 111 to the state specifying unit 3802 is the automatic reproduction mode, and the manipulating procedure proceeds to step S2103 if the input mode is the manipulation mode, in the input/output IF 111.

In step S2102, the teaching data stored in the internal storage unit of the operation information generating unit 109 is set to be the operation information in the operation information generating unit 109, and the manipulating procedure proceeds to step S2104.

In step S2103, information acquired by the insertion information acquiring unit 106 is set to be the operation information in the operation information generating unit 109, and the manipulating procedure proceeds to step S2104.

In step S2104, the state specifying unit 3802 decides whether the vibration control mode is ON or OFF in the state specifying unit 3802. If the state specifying unit 3802 decides that the vibration control mode is ON, the manipulating procedure proceeds to step S3701. If the state specifying unit 2802 decides that the vibration control mode is OFF, the manipulating procedure proceeds to step S2110. The manipulator selects the ON/OFF of the vibration control mode based on the information input to the state specifying unit 3802 by using the input/output IF 111.

In step S3701, the state specifying unit 3802 acquires the state transition information by the state transition storage unit 2801, and the manipulating procedure proceeds to step S3702.

In step S3702, the manipulating procedure proceeds to step S2110 if the state specifying unit 3802 decides that the newest state in the state transition information acquired from the state transition storage unit 2801 is the "second progress" state, and the manipulating procedure proceeds to step S3703 if the state specifying unit 3802 decides that the newest state is not the "second progress" state.

In step S2110, the state specifying unit 3802 generates the state information for carrying out no vibration control, and the manipulating procedure proceeds to step S2111.

In step S3703, the manipulating procedure proceeds to step S3704 if the state specifying unit 3802 decides that the newest state in the state transition information acquired by the state transition storage unit 2801 is the "first progress" state, and the manipulating procedure proceeds to step S3705 if the state specifying unit 3802 decides that the newest state is not the "first progress" state.

In step S3704, the state specifying unit 3802 generates the state information for carrying out the vibration control, and the manipulating procedure proceeds to step S4401. Herein, the magnitude of the vibration is made the smallest as compared with the other cases (a state F in FIG. 44).

In step S3705, the manipulating procedure proceeds to step S3706 if the state specifying unit 3802 decides that the newest state in the state transition information acquired from the state transition storage unit 2801 is the "first stop" state, and the manipulating procedure proceeds to step S3709 the state specifying unit 3802 decides that the newest state is not the "first stop" state.

In step S3706, the manipulating procedure proceeds to step S3707 if the state specifying unit 3802 decides that a last state from the newest state in the state transition information acquired from the state transition storage unit 2801 is the "first progress" state, and the manipulating procedure proceeds to step S3708 if the state specifying unit 3802 decides that the last state is not the "first progress" state.

In step S3707, the state specifying unit 3802 generates the state information for carrying out the vibration control, and the manipulating procedure proceeds to step S4401. Herein, the magnitude of the vibration is made greater than that in the case of step S3704 and is made smaller than that in the case of step S3708 (a state E in FIG. 44).

In step S3708, the state specifying unit 3802 generates the state information for carrying out the vibration control, and the manipulating procedure proceeds to step S4401. Herein, the magnitude of the vibration is made greater than that in the case of step S3707 and is made smaller than that in the case of step S3711 (a state D in FIG. 44).

In step S3709, the manipulating procedure proceeds to step S3710 if the state specifying unit 3802 decides that a last state from the newest state in the state transition information acquired from the state transition storage unit 2801 is the "first stop" state, and the manipulating procedure proceeds to step S3713 if the state specifying unit 3802 decides that the last state is not the "first stop" state.

In step S3710, the manipulating procedure proceeds to step S3711 if the state specifying unit 3802 decides that a second previous state to the newest state in the state transition information acquired from the state transition storage unit 2801 is the "first progress" state, and the manipulating procedure proceeds to step S3712 if the state specifying unit 3802 decides that the second previous state is not the "first progress" state.

In step S3711, the state specifying unit 3802 generates the state information for carrying out the vibration control, and the manipulating procedure proceeds to step S4401. Herein, the magnitude of the vibration is made greater than that in the case of step S3708 and is made smaller than that in the case of step S3712 (a state C in FIG. 44).

In step S3712, the state specifying unit 3802 generates the state information for carrying out the vibration control, and the manipulating procedure proceeds to step S4401. Herein, the magnitude of the vibration is made greater than that in the case of step S3711 and is made smaller than that in the case of step S3713 (a state B in FIG. 44).

In step S3713, the state specifying unit 3802 generates the state information for carrying out the vibration control, and the manipulating procedure proceeds to step S4401. Herein, the magnitude of the vibration is made the greatest as compared with the others (a state A in FIG. 44).

In step S4401, the state specifying unit 3802 acquires the control start state information from the control start state specifying unit 3801, and the manipulating procedure proceeds to step S4402.

In step S4402, the manipulating procedure proceeds to step S4403 if the state specifying unit 3802 decides that the control start state information acquired from the control start state specifying unit 3801 is 1, and the manipulating procedure proceeds to step S2111 if the state specifying unit 3802 decides that the control start state information is 0.

In step S4403, the state specifying unit 3802 multiples the vibration information by a constant (the constant is greater than 0 and is smaller than 1) to generate state information having the value of the vibration information reduced, and the manipulating procedure proceeds to step S2111. For example, the constant is set to be 0.5.

In step S2111, the operation information generating unit 109 acquires the state information from the state specifying unit 3802, and adds the operation information for the vibration control to generate operation information if the vibration control is to be carried out. The operation information generating unit 109 generates the operation information directly from the acquired operation information if the vibration control is not to be carried out. The operation information is output from the operation information generating unit 109 to the control unit 110, and the operation of the robot arm 102 is controlled based on the operation information acquired in the control unit 110.

Effect of the Third Embodiment

In the work for inserting the insertion member such as the guide wire 302, the magnitude of the vibration is regulated by the state specifying unit 3802 depending on the moving state of the guide wire 302 at the start of the vibration control. Consequently, it is possible to reduce a load to be applied to the blood vessel 301 as compared with the second embodiment. Thus, it is possible to remove getting-stuck with a vibration having smaller force applied to the blood vessel 301.

Fourth Embodiment

Figure 45:
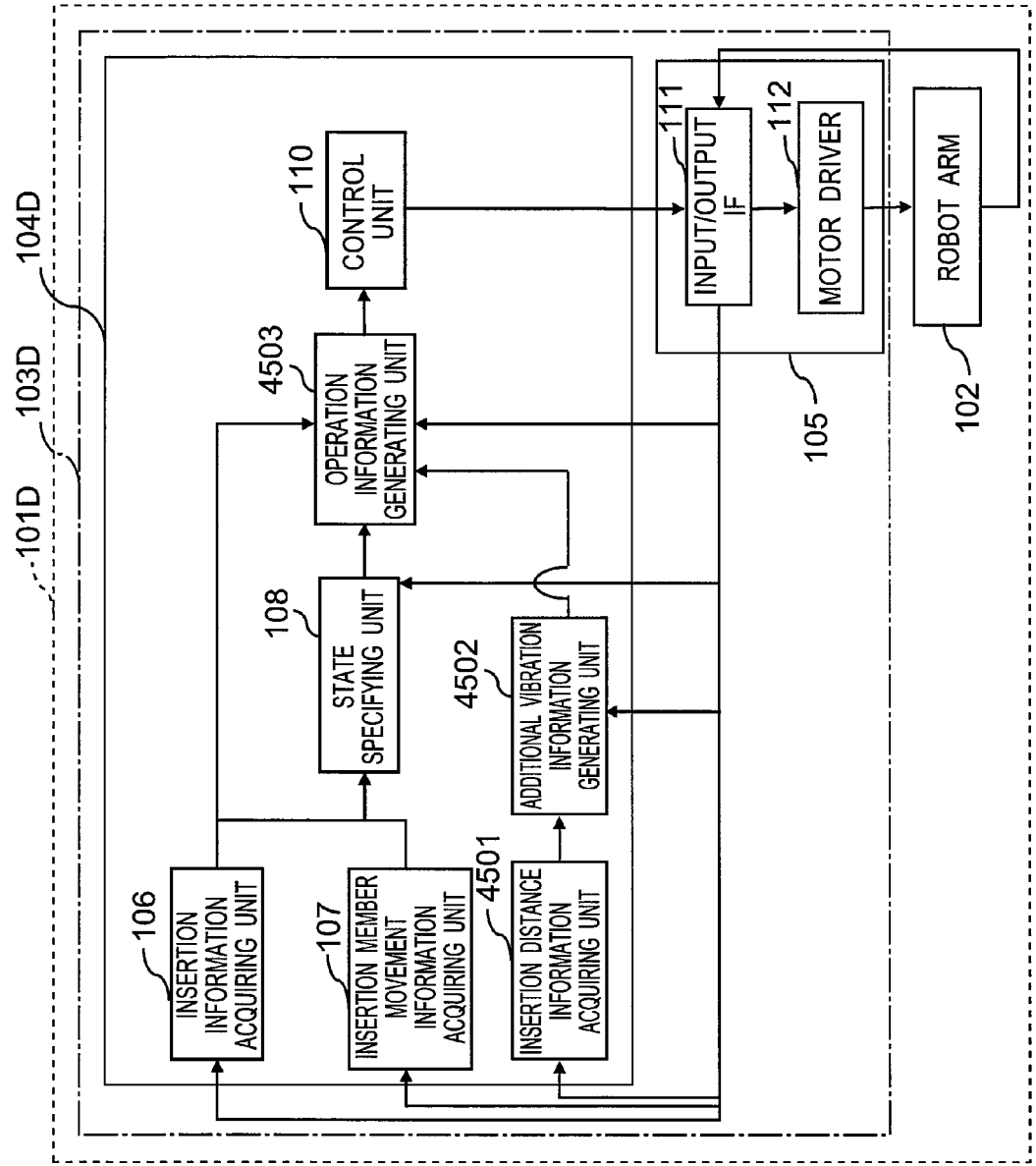
FIG. 45 is a block diagram showing a robot arm in a robot according to a fourth embodiment of the present disclosure.

FIG. 45 is a block diagram showing a robot 101D according to an example of an insertion apparatus in accordance with a fourth embodiment of the present disclosure. A control apparatus 103D of the robot arm 102 according to an example of a control apparatus of an insertion apparatus in accordance with the fourth embodiment of the present disclosure has a feature that a control apparatus body unit 104D is provided with an insertion distance information acquiring unit 4501, an additional vibration information generating unit 4502, and an operation information generating unit 4503. Since the robot arm 102; the peripheral apparatus 105; and the insertion information acquiring unit 106, the insertion member movement information acquiring unit 107, the state specifying unit 108, and the control unit 110 in the control apparatus body unit 104D of the control apparatus 103D in the robot 101D according to the fourth embodiment of the present disclosure are the same as those in the first embodiment, they have common reference numerals and the description of common parts are omitted, and only different parts will be explained below in detail.

The insertion distance information acquiring unit 4501 acquires position information, orientation information, velocity information, and angular velocity information about the robot arm 102 in the same manner as the insertion information acquiring unit 106. The insertion distance information acquiring unit 4501 calculates insertion distance information from an insertion port of a guide wire 302 based on the acquired position information. The insertion distance information implies a movement distance in a body lumen of a tip of the insertion member. Referring to a method of calculating the insertion distance information by the insertion distance information acquiring unit 4501, a movement amount for each certain time is obtained from an acquiring start time for the position information and the movement amount for each certain time thus obtained is added to calculate the insertion distance information.

The insertion distance information acquiring unit 4501 outputs the calculated insertion distance information and time information to an additional vibration information generating unit 4502.

The additional vibration information generating unit 4502 has a function for varying the magnitude of a vibration based on the insertion distance information acquired from the insertion distance information acquiring unit 4501. The additional function will be described below.

Figure 46:
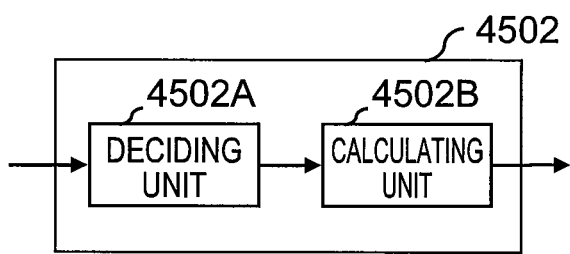
FIG. 46 is a block diagram showing an additional vibration information generating unit in the robot according to the fourth embodiment of the present disclosure.

The additional vibration information generating unit 4502 varies the value of the vibration information based on the insertion distance information acquired from the insertion distance information acquiring unit 4501. FIG. 46 shows an internal structure of the additional vibration information generating unit 4502, and the additional vibration information generating unit 4502 is configured from a deciding unit 4502A and a calculating unit 4502B.

The deciding unit 4502A decides start and end of generation based on the additional vibration information acquired from the insertion distance information acquiring unit 4501. The decision is made by comparison between insertion distance information and a threshold. When the deciding unit 4502A decides that the insertion distance information exceeds a start threshold (a first threshold) (for example, 30 cm), the generation of the additional vibration information is started. When the deciding unit 4502A decides that the insertion distance information exceeds an end threshold (a second threshold) (for example, 100 cm), the generation of the additional information is ended. The end threshold (the second threshold) is greater than the start threshold (the first threshold).

The calculating unit 4502B calculates the generated additional vibration information. The calculating method will be described. The value of the vibration information is calculated based on the insertion distance information. There are various calculating methods including a calculating method using a condition and a calculating method using a function. Referring to the calculating method using the condition, for example, the value of the vibration information is increased by one every time the insertion distance is increased by 10 mm. Referring to the calculating method using the function, for example, the calculation is carried out in the expression of $y=0.1x$ or $y=0.1 x^2$, wherein the insertion distance information is represented by x and the additional vibration information is represented by y. For the calculating method using the function, any function can be used. Thus, the magnitude of the vibration is increased when the insertion distance is longer. Even if the insertion distance is increased, consequently, the vibration control in the insertion port part can be transmitted to the tip part. Thus, it is possible to prevent a situation that a vibration is difficult to be transmitted to the tip portion of the guide wire 302 with increasing insertion distance due to an increase of a portion of the guide wire 302 in contact with the blood vessel 301 to cause a higher contact resistance.

The operation information generating unit 4503 is provided in the control apparatus body unit 104D in place of the operation information generating unit 109, and operation information is generated by adding the additional vibration information acquired from the additional vibration information generating unit 4502 to the vibration information acquired from the state specifying unit 108 in addition to the function of the operation information generating unit 109 according to the first embodiment.

Figure 47:
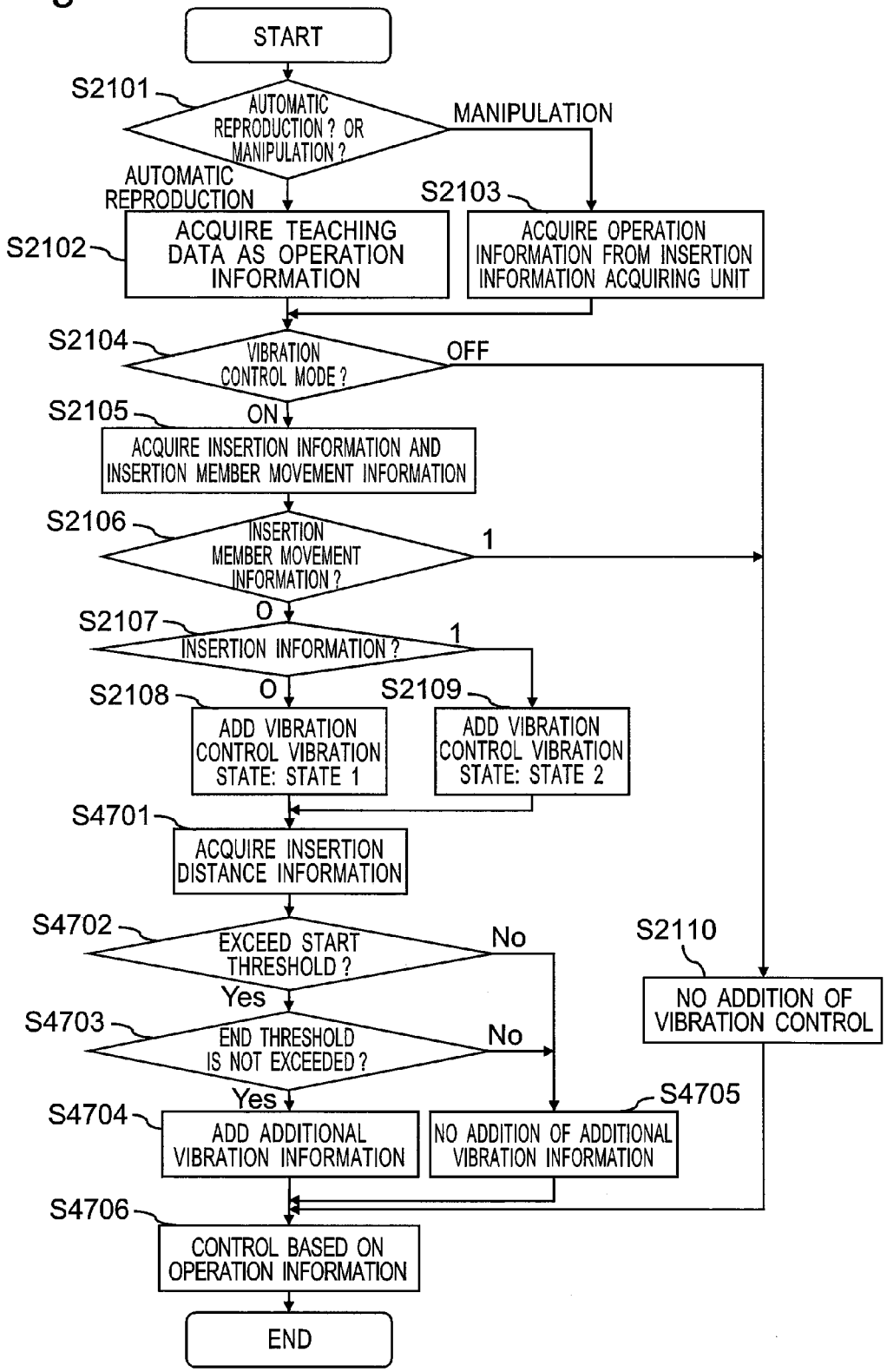
FIG. 47 is a flowchart in a manipulation procedure of a control apparatus for the robot according to the fourth embodiment of the present disclosure.

A procedure for manipulating the control apparatus 103D for the robot arm 102D according to the fourth embodiment will be described with reference to a flowchart of FIG. 47.

First of all, in step S2101, the manipulating procedure proceeds to step S2102 if the mode input from the input/output IF 111 to the state specifying unit 108 is the automatic reproduction mode, and the manipulating procedure proceeds to step S2103 if the input mode is the manipulation mode, in the input/output IF 111.

In step S2102, the teaching data stored in the internal storage unit of the operation information generating unit 4503 is set to be the operation information in the operation information generating unit 4503, and the manipulating procedure proceeds to step S2104.

In step S2103, information acquired from the insertion information acquiring unit 106 is set to be the operation information in the operation information generating unit 4503, and the manipulating procedure proceeds to step S2104.

In step S2104, the state specifying unit 108 decides whether the vibration control mode is ON or OFF in the state specifying unit 108. If the state specifying unit 108 decides that the vibration control mode is ON, the manipulating procedure proceeds to step S2105. If the state specifying unit 108 decides that the vibration control mode is OFF, the manipulating procedure proceeds to step S2110. The manipulator selects the ON/OFF of the vibration control mode based on the information input to the state specifying unit 108 by using the input/output IF 111. The selection can be carried out for the following reason. The manipulator can select the case in which the inserting work is performed by only the manipulator or the case in which the vibration control is added to perform the inserting work, by his (her) intention.

In step S2105, the state specifying unit 108 acquires the insertion information from the insertion information acquiring unit 106 and acquires the insertion member movement information from the insertion member movement information acquiring unit 107, and the manipulating procedure proceeds to step S2106.

In step S2106, the manipulating procedure proceeds to step S2107 if the state specifying unit 108 decides that the value of the insertion member movement information acquired from the insertion member movement information acquiring unit 107 is 0, and the manipulating procedure proceeds to step S2110 if the state specifying unit 108 decides that the value of the insertion member movement information is 1.

In step S2107, the manipulating procedure proceeds to step S2108 if the state specifying unit 108 decides that the value of the insertion information acquired from the insertion information acquiring unit 106 is 0, and the manipulating procedure proceeds to step S2109 if the state specifying unit 108 decides that the value of the insertion information is 1.

In step S2108, the state specifying unit 108 generates the state information for carrying out the vibration control, and the manipulating procedure proceeds to step S4701. Herein, the magnitude of a vibration is made greater than that in the case of step S2109 (the first state in FIG. 47). Then, the manipulating procedure proceeds to step S4701.

In step S2109, the state specifying unit 108 generates the state information for carrying out the vibration control, and the manipulating procedure proceeds to step S4701. Herein, the magnitude of a vibration is made smaller than that in the case of step S2108 (the second state in FIG. 47). Then, the manipulating procedure proceeds to step S4701.

In step S2110, the state specifying unit 108 generates the state information for carrying out no vibration control, and the manipulating procedure proceeds to step S4706.

In step S4701, the insertion distance information acquiring unit 4501 acquires the insertion distance information, and the manipulating procedure proceeds to step S4702.

In step S4702, the additional vibration information generating unit 4502 compares the insertion distance information with the start threshold (for example, 30 cm). If the additional vibration information generating unit 4502 decides that the insertion distance exceeds the start threshold, the manipulating procedure proceeds to step S4703. If the additional vibration information generating unit 4502 decides that the insertion distance does not exceed the start threshold, the manipulating procedure proceeds to step S4705.

In step S4703, the additional vibration information generating unit 4502 compares the insertion distance information with the end threshold (for example, 100 cm). If the additional vibration information generating unit 4502 decides that the insertion distance exceeds the end threshold, the manipulating procedure proceeds to step S4705. If the additional vibration information generating unit 4502 decides that the insertion distance does not exceed the end threshold, the manipulating procedure proceeds to step S4704.

In step S4704, the additional vibration information generating unit 4502 generates the additional vibration information based on the insertion distance information, and the manipulating procedure proceeds to step S4706.

In step S4705, the additional vibration information generating unit 4502 generates the additional vibration information to which the vibration information is not added, and the manipulating procedure proceeds to step S4706.

In step S4706, the operation information generating unit 4503 acquires the state information from the state specifying unit 108. If the vibration control is to be carried out, the operation information of the additional vibration information is added to the operation information about the vibration control to generate operation information. If the vibration control is not to be carried out, the operation information generating unit 4503 generates the operation information directly from the acquired operation information. The operation information is output from the operation information generating unit 4503 to the control unit 110, and the operation of the robot arm 102 is controlled based on the operation information acquired by the control unit 110.

Effect of Fourth Embodiment

In the work for inserting the insertion member such as the guide wire 302, it is possible to accurately transmit a vibration to the tip portion of the guide wire 302 by varying the magnitude of the vibration depending on the insertion distance. Consequently, it is possible to remove getting-stuck of the tip portion of the guide wire 302 in a blood vessel part or the like.

Fifth Embodiment

Figure 48:
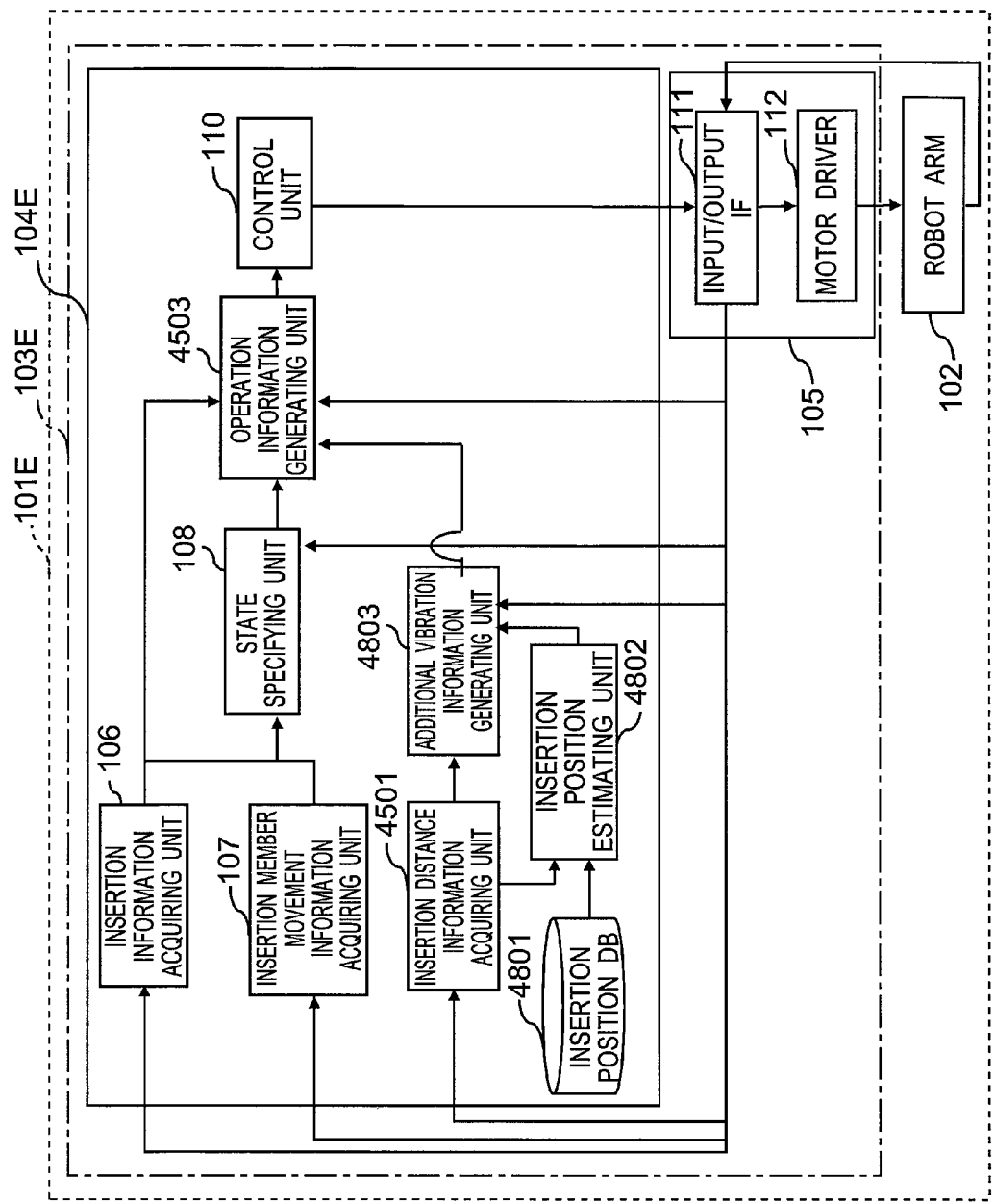
FIG. 48 is a block diagram showing a robot arm in a robot according to a fifth embodiment of the present disclosure.

FIG. 48 is a block diagram showing a robot 101E according to an example of an insertion apparatus in accordance with a fifth embodiment of the present disclosure. A control apparatus 103E of a robot arm 102 according to an example of a control apparatus of an insertion apparatus in accordance with the fifth embodiment of the present disclosure has a feature that a control apparatus body unit 104E is provided with an insertion position database 4801, an insertion position estimating unit 4802, and an additional vibration information generating unit 4803. Since the robot arm 102; the peripheral apparatus 105; and the insertion information acquiring unit 106, the insertion member movement information acquiring unit 107, the state specifying unit 108, the control unit 110, the insertion distance information acquiring unit 4501, and the operation information generating unit 4503 in the control apparatus body unit 104E of the control apparatus 103E in the robot 101E according to the fifth embodiment of the present disclosure are the same as those in the fourth embodiment, they have common reference numerals and the description of common parts are omitted, and only different parts will be explained below in detail.

An insertion position database 4801 is a database storing relationship information in which insertion distance information, human body region information, and additional vibration information correspond to each other. For example, an example of a database in a heart will be described with reference to FIG. 49. The human body region information and the additional vibration information corresponding to the insertion distance information are stored in the insertion position database 4801 for the heart. A person inputs the human body region information and the additional vibration information to the insertion position database 4801 by using an input/output IF 111 based on information about an inspection to be performed in advance, and constructs the insertion position database 4801. Although the description has been given to the method of increasing the vibration information with increase in the insertion distance in the fourth embodiment, it is also possible to employ a method of reducing the vibration information in consideration of a thinner blood vessel or approach to a lesion site with increase in the insertion distance as shown in FIG. 49. In other words, for example, it is possible to increase the vibration information with the increase in the insertion distance till reaching a certain distance (threshold) and to reduce the vibration information with the increase in the insertion distance when the distance (threshold) is exceeded.

The insertion position database 4801 outputs, to an insertion position estimating unit 4802, the information in the database including the stored insertion distance information, human body region information, and additional vibration information.

The insertion position estimating unit 4802 acquires the insertion distance information from the insertion distance information acquiring unit 4501 and acquires the information in the database including the insertion distance information, the human body region information, and the additional vibration information from the insertion position database 4801. The insertion position estimating unit 4802 derives the additional vibration information by referring to the information in the database based on the acquired insertion distance information. The insertion position estimating unit 4802 outputs the derived additional vibration information to the additional vibration information generating unit 4803.

The additional vibration information generating unit 4803 is provided in the control apparatus body unit 104E in place of the additional vibration information generating unit 4502, and additional vibration information acquired from the insertion position estimating unit 4802 is output to the operation information generating unit 4503 in addition to the function of the additional vibration information generating unit 4502 according to the fourth embodiment.

Figure 50:
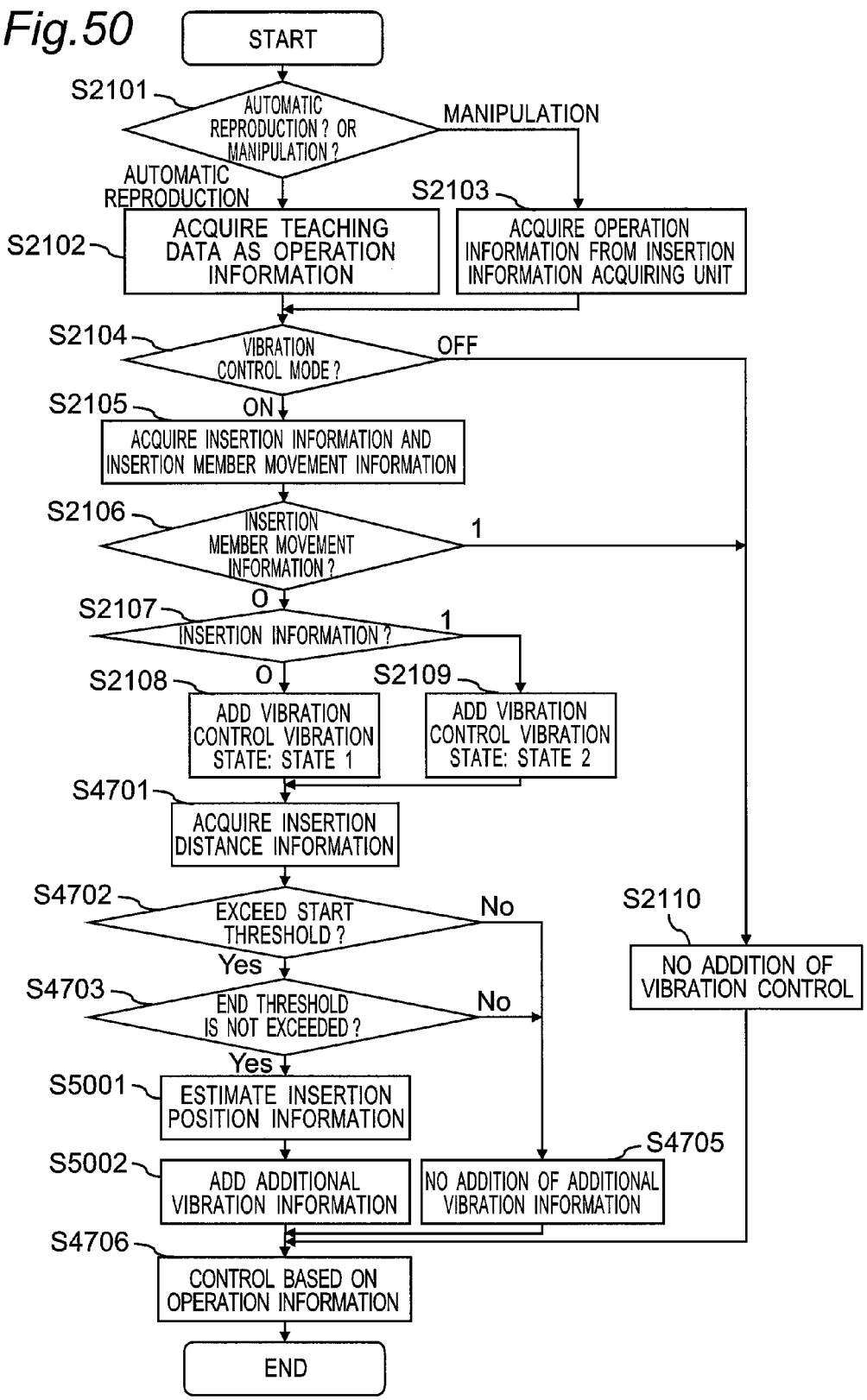
FIG. 50 is a flowchart in a manipulation procedure of a control apparatus for the robot according to the fifth embodiment of the present disclosure.

A procedure for manipulating the control apparatus 103E for the robot arm 102E according to the fifth embodiment will be described with reference to a flowchart of FIG. 50.

First of all, in step S2101, the manipulating procedure proceeds to step S2102 if the mode input from the input/output IF 111 to the state specifying unit 108 is the automatic reproduction mode, and the manipulating procedure proceeds to step S2103 if the input mode is the manipulation mode, in the input/output IF 111.

In step S2102, the teaching data stored in the internal storage unit of the operation information generating unit 4503 is set to be the operation information in the operation information generating unit 4503, and the manipulating procedure proceeds to step S2104.

In step S2103, information acquired from the insertion information acquiring unit 106 is set to be the operation information in the operation information generating unit 4503, and the manipulating procedure proceeds to step S2104.

In step S2104, the state specifying unit 108 decides whether the vibration control mode is ON or OFF in the state specifying unit 108. If the state specifying unit 108 decides that the vibration control mode is ON, the manipulating procedure proceeds to step S2105. If the state specifying unit 108 decides that the vibration control mode is OFF, the manipulating procedure proceeds to step S2110. The manipulator selects the ON/OFF of the vibration control mode based on the information input to the state specifying unit 108 by using the input/output IF 111. The selection can be carried out for the following reason. The manipulator can select the case in which the inserting work is performed by only the manipulator or the case in which the vibration control is added to perform the inserting work, by his (her) intention.

In step S2105, the state specifying unit 108 acquires the insertion information from the insertion information acquiring unit 106 and acquires the insertion member movement information from the insertion member movement information acquiring unit 107, and the manipulating procedure proceeds to step S2106.

In step S2106, the manipulating procedure proceeds to step S2107 if the state specifying unit 108 decides that the value of the insertion member movement information acquired from the insertion member movement information acquiring unit 107 is 0, and the manipulating procedure proceeds to step S2110 if the state specifying unit 108 decides that the value of the insertion member movement information is 1.

In step S2107, the manipulating procedure proceeds to step S2108 if the state specifying unit 108 decides that the value of the insertion information acquired from the insertion information acquiring unit 106 is 0, and the manipulating procedure proceeds to step S2109 if the state specifying unit 108 decides that the value of the insertion information is 1.

In step S2108, the state specifying unit 108 generates the state information for carrying out the vibration control, and the manipulating procedure proceeds to step S4701. Herein, the magnitude of a vibration is made greater than that in the case of step S2109 (the first state in FIG. 47). Then, the manipulating procedure proceeds to step S4701.

In step S2109, the state specifying unit 108 generates the state information for carrying out the vibration control, and the manipulating procedure proceeds to step S4701. Herein, the magnitude of a vibration is made smaller than that in the case of step S2108 (the second state in FIG. 47). Then, the manipulating procedure proceeds to step S4701.

In step S2110, the state specifying unit 108 generates the state information for carrying out no vibration control, and the manipulating procedure proceeds to step S4706.

In step S4701, the insertion distance information acquiring unit 4501 acquires the insertion distance information, and the manipulating procedure proceeds to step S4702.

In step S4702, the additional vibration information generating unit 4803 compares the insertion distance information with the start threshold (for example, 30 cm). If the additional vibration information generating unit 4803 decides that the insertion distance exceeds the start threshold, the manipulating procedure proceeds to step S4703. If the additional vibration information generating unit 4803 decides that the insertion distance does not exceed the start threshold, the manipulating procedure proceeds to step S4705.

In step S4703, the additional vibration information generating unit 4803 compares the insertion distance information with the end threshold (for example, 100 cm). If the additional vibration information generating unit 4803 decides that the insertion distance exceeds the end threshold, the manipulating procedure proceeds to step S5001. If the additional vibration information generating unit 4803 decides that the insertion distance does not exceed the end threshold, the manipulating procedure proceeds to step S4704.

In step S5001, the insertion position estimating unit 4802 derives the additional vibration information by referring to the information in the insertion position database 4801 based on the acquired insertion distance information, and the manipulating procedure proceeds to step S5002.

In step S5002, the additional vibration information generating unit 4803 generates the additional vibration information based on the insertion distance information, and furthermore, acquires the additional vibration information from the insertion position estimating unit 4802, and the manipulating procedure proceeds to step S4706.

In step S4705, the additional vibration information generating unit 4803 generates the additional vibration information to which the vibration information is not added, and the manipulating procedure proceeds to step S4706.

In step S4706, the operation information generating unit 4503 acquires the state information from the state specifying unit 108. If the vibration control is to be carried out, the operation information of the additional vibration information is added to the operation information about the vibration control to generate operation information. If the vibration control is not to be carried out, the operation information generating unit 4503 generates the operation information directly from the acquired operation information. The operation information is output from the operation information generating unit 4503 to the control unit 110, and the operation of the robot arm 102 is controlled based on the operation information acquired by the control unit 110.

Effect of Fifth Embodiment

In the work for inserting the insertion member such as the guide wire 302, the magnitude of the vibration is varied depending on the insertion position of the patients' body. Consequently, it is possible to change the magnitude of the vibration for every patient or region. As a result, it is possible to carry out an accurate insertion work with a small load.

Though the present disclosure has been described above based on the above first to fifth embodiments, the present disclosure should not be limited to the above-described first to fifth embodiments. For example, the present disclosure also includes the following cases.

Part or entirety of each of the above-described control apparatuses is actually a computer system that includes, for example, a microprocessor, ROM, RAM, hard disk unit, display unit, keyboard, mouse, and the like. A computer program is stored on the RAM or the hard disk unit. Functions of each of the control apparatuses can be achieved by the microprocessor operating according to the computer program. The computer program mentioned here is a combination of a plurality of instruction codes that indicate commands to a computer for achieving predetermined functions.

For example, each component can be implemented as a result that a program executing section (part/unit) such as a CPU reads and executes software programs recorded in a recording medium such as a hard disk or semiconductor memory. Here, software that implements a part or entirety of the control apparatus according to each of the above-mentioned embodiments is a following program. That is to say, this program has a computer execute the sections (parts/units) defined in claims. The program has a computer execute the units/steps defined in claims. That is, such a program is a control program for a control apparatus of an insertion apparatus that inserts an insertion member of a catheter or an endoscope into a body lumen, the program for causing a computer to function as:

a tip movement information acquiring unit that acquires tip movement information indicative of presence of movement in the body lumen of a tip of the insertion member;

a non-tip area movement information acquiring unit that acquires non-tip area movement information indicative of presence of a moving operation in the body lumen of a non-tip area other than the tip of the insertion member;

a state specifying unit that, by using the non-tip area movement information acquired by the non-tip area movement information acquiring unit and the tip movement information acquired by the tip movement information acquiring unit, (a) specifies as a first tip stop state for vibrating the insertion member, a case where the non-tip area of the insertion member is moved and the tip of the insertion member is not moved, and (b) specifies as a second tip stop state for vibrating the insertion member more greatly than in the first tip stop state of (a), a case where the non-tip area of the insertion member is not moved and the tip of the insertion member is not moved;

an operation information generating unit that generates operation information about the insertion apparatus to execute the first tip stop state of (a) or the second tip stop state of (b) which is specified by the state specifying unit; and a control unit that controls an operation of the insertion member based on the operation information generated by the operation information generating unit.

In addition, it may be possible to execute the program by downloading it from a server or reading it from a predetermined storage medium (an optical disc such as a CD-ROM, a magnetic disc, a semiconductor memory, or the like).

Further, one or more computers can be used to execute the program. That is, centralized processing or distributed processing can be performed.

By properly combining the arbitrary embodiment (s) or modification(s) of the aforementioned various embodiments and modifications, the effects possessed by the embodiment(s) or modification(s) can be produced.

The control apparatus and the control method for the insertion apparatus, the insertion apparatus having the control apparatus, the control program of the insertion apparatus, and the controlling integrated electronic circuit of the insertion apparatus in accordance with the present disclosure carry out the vibration control corresponding to the state of the insertion member to enable the getting-stuck of the tip of the insertion member to be removed with a vibration having such a proper magnitude as not to cause an overload when the getting-stuck occurs in the work for inserting the insertion member, and are useful for a control apparatus and a control method for an insertion apparatus, an insertion apparatus having the control apparatus, a control program of an insertion apparatus, and a controlling integrated electronic circuit of an insertion apparatus in a medical apparatus. Moreover, the control apparatus and the control method for the insertion apparatus, the insertion apparatus having the control apparatus, the control program of the insertion apparatus, and the controlling integrated electronic circuit of the insertion apparatus according to the present disclosure are not restricted to the medical apparatus but might be applied to a control apparatus and a control method for an insertion apparatus, an insertion apparatus having the control apparatus, a control program of an insertion apparatus, and a controlling integrated electronic circuit of an insertion apparatus for an industrial apparatus or a household apparatus.

The entire disclosure of Japanese Patent Application No. 2012-154847 filed on Jul. 10, 2012, including specification, claims, drawings, and summary are incorporated herein by reference in its entirety.

Although the present disclosure has been fully described in connection with the embodiments thereof with reference to the accompanying drawings, it is to be noted that various changes and modifications are apparent to those skilled in the art. Such changes and modifications are to be understood as included within the scope of the present disclosure as defined by the appended claims unless they depart therefrom.

What is claimed is:

1. A control apparatus of an insertion apparatus configured to insert an insertion member of a catheter into a body lumen, the control apparatus comprising:

a tip movement information acquiring unit that acquires tip movement information indicative of presence of movement in the body lumen of a tip of the insertion member;

a non-tip area movement information acquiring unit that acquires non-tip area movement information indicative of presence of a moving operation in the body lumen of a non-tip area other than the tip of the insertion member;

a state specifying unit that, by using the non-tip area movement information acquired by the non-tip area movement information acquiring unit and the tip movement information acquired by the tip movement information acquiring unit, (a) specifies as a first tip stop state for vibrating the insertion member with a first magnitude of a vibration, a case where the non-tip area of the insertion member is moved and the tip of the insertion member is not moved, and (b) specifies as a second tip stop state for vibrating the insertion member with a second magnitude of a vibration greater than the first magnitude of the vibration in the first tip stop state of (a), a case where the non-tip area of the insertion member is not moved and the tip of the insertion member is not moved;

an operation information generating unit that generates operation information about the insertion apparatus to execute the first tip stop state of (a) or the second tip stop state of (b) which is specified by the state specifying unit; and a control unit that controls an operation of the insertion member based on the operation information generated by the operation information generating unit, wherein a maximum value of the second magnitude of the vibration in the second tip stop state is set to be an amplitude of 0.3 mm, and the control unit controls the operation of the insertion member by applying vibration control to execute the vibrating of the insertion member in the first tip stop state of (a) or the second tip stop state of (b).

2. The control apparatus of an insertion apparatus according to claim 1, wherein the state specifying unit specifies the first tip stop state of (a) and the second tip stop state of (b) by using the non-tip area movement information acquired by the non-tip area movement information acquiring unit and the tip movement information acquired by the tip movement information acquiring unit, and specifies as a state in which the insertion member is not vibrated, a case where the tip of the insertion member is moved regardless of the presence of the moving operation in the non-tip area of the insertion member, and the operation information generating unit generates the operation information about the insertion apparatus for executing any of the states specified by the state specifying unit.

3. The control apparatus of an insertion apparatus according to claim 1, wherein the state specifying unit specifies the first tip stop state of (a) and the second tip stop state of (b) by using the non-tip area movement information acquired by the non-tip area movement information acquiring unit and the tip movement information acquired by the tip movement information acquiring unit, and (c) specifies as a state in which the insertion member is vibrated less than in the first tip stop state of (a), a case where the non-tip area of the insertion member is moved and the tip of the insertion member is moved, and the operation information generating unit generates the operation information about the insertion apparatus for executing any of the states (a) to (c) specified by the state specifying unit.

4. The control apparatus of an insertion apparatus according to claim 3, wherein the state specifying unit specifies the first tip stop state of (a), the second tip stop state of (b), and the state of (c) by using the non-tip area movement information acquired by the non-tip area movement information acquiring unit and the tip movement information acquired by the tip movement information acquiring unit, and (d) specifies as a second tip area movement state in which the insertion member is not vibrated, a case where the non-tip area of the insertion member is not moved and the tip of the insertion member is moved, and the operation information generating unit generates the operation information about the insertion apparatus for executing any of the states (a) to (d) specified by the state specifying unit.

5. The control apparatus of an insertion apparatus according to claim 1, wherein the operation information generating unit generates the operation information about the insertion apparatus in which a vibration of the insertion member is in an insertion direction of the insertion member and/or a rotation direction around the insertion direction of the insertion member in a case where the state specified by the state specifying unit is the first tip stop state of (a) or the second tip stop state of (b).

6. The control apparatus of an insertion apparatus according to claim 1, wherein
the operation information generating unit generates the operation information about the insertion apparatus such that the vibration in the second tip stop state of (b) has a vibration amplitude, a vibration cycle, or an advance ratio greater than the vibration in the first tip stop state of (a).

7. The control apparatus of an insertion apparatus according to claim 1, wherein
the state specifying unit specifies the first tip stop state of (a) and the second tip stop state of (b) by using the non-tip area movement information acquired by the non-tip area movement information acquiring unit and the tip movement information acquired by the tip movement information acquiring unit, and
(o) specifies as a first tip area movement state in which the insertion member is not vibrated, a case where the non-tip area of the insertion member is moved and the tip of the insertion member is moved, and
the operation information generating unit generates the operation information about the insertion apparatus for executing the first tip stop state of (a), the second tip stop state of (b), or the first tip area movement state of (o) which is specified by the state specifying unit.

8. The control apparatus of an insertion apparatus according to claim 7, further comprising:
a state transition storage unit that generates state transition information in which the non-tip area movement information and the tip movement information acquired by the state specifying unit are arranged in time-series order and stores the generated state transition information,
wherein when generating the state transition information, the state transition storage unit
(A) adds the non-tip area movement information and the tip movement information acquired by the state specifying unit to the state transition information in a case where a state acquired by the state specifying unit is different from a state acquired by the state specifying unit immediately before, and
(B) does not add the non-tip area movement information and the tip movement information acquired by the state specifying unit to the state transition information in a case where the state acquired by the state specifying unit is identical to the state acquired by the state specifying unit immediately before, and
the state specifying unit uses the non-tip area movement information acquired by the non-tip area movement information acquiring unit, the tip movement information acquired by the tip movement information acquiring unit, and the state transition information acquired by the state transition storage unit to
(e) specify as a state in which the insertion member is vibrated, a case where a newest state in the state transition information is the first tip stop state of (a) and a last state in the state transition information is the first tip area movement state of (o),
(f) specify as a state in which the insertion member is vibrated more than in the state of (e), a case where the newest state in the state transition information is the first tip stop state of (a) and the last state in the state transition information is not the first tip area movement state of (o),
(g) specify as a state in which the insertion member is vibrated more than in the state of (f), a case where the newest state in the state transition information is the second tip stop state of (b), the last state in the state transition information is the first tip stop state of (a), and a second previous state is the first tip area movement state of (o), and
(h) specify as a state in which the insertion member is vibrated more than in the state of (g), a case where the newest state in the state transition information is the second tip stop state of (b), the last state in the state transition information is the first tip stop state of (a), and the second previous state is not the first tip area movement state of (o), and
the operation information generating unit generates the operation information about the insertion apparatus for executing any of the states of (e) to (h) specified by the state specifying unit.

9. The control apparatus of an insertion apparatus according to claim 8, wherein
the state specifying unit (c) specifies as a state in which the insertion member is vibrated less than in the first tip stop state of (a), a case where the non-tip area of the insertion member is moved and the tip of the insertion member is moved, by using the non-tip area movement information acquired by the non-tip area movement information acquiring unit and the tip movement information acquired by the tip movement information acquiring unit and
the state specifying unit specifies the states of (e) to (h) by using the non-tip area movement information acquired by the non-tip area movement information acquiring unit, the tip movement information acquired by the tip movement information acquiring unit, and the state transition information acquired from the state transition storage unit, and
(i) specifies a state in which the insertion member is vibrated less than in the first tip stop state of (a) in a case where the newest state in the state transition information is the state of (c),
(j) specifies a state in which the insertion member is vibrated more than in the state of (h) in a case where the newest state in the state transition information is the second tip stop state of (b) and the last state in the state transition information is not the first tip stop state of (a), and
(k) specifies a state in which the insertion member is not vibrated in a case where the newest state in the state transition information is the second tip area movement state of (d), and
the operation information generating unit generates the operation information about the insertion apparatus for executing any of the states of (e) to (k) specified by the state specifying unit.

10. The control apparatus of an insertion apparatus according to claim 1, further comprising:
an insertion distance information acquiring unit that acquires insertion distance information indicative of a moving distance of the tip of the insertion member in the body lumen; and
an additional vibration information generating unit that generates additional vibration information to increase a magnitude of a vibration with a longer insertion distance based on the insertion distance information acquired by the insertion distance information acquiring unit, wherein
the operation information generating unit adds the additional vibration information acquired by the additional vibration information generating unit to information about a vibration to execute the first tip stop state of (a)

or the second tip stop state of (b) which is specified by the state specifying unit, thereby generating the operation information.

11. The control apparatus of an insertion apparatus according to claim 10, wherein
the additional vibration information generating unit generates the additional vibration information in a case where the insertion distance information acquired by the insertion distance information acquiring unit is more than a first threshold and is less than a second threshold which is greater than the first threshold.

12. The control apparatus of an insertion apparatus according to claim 1, further comprising:
an insertion distance information acquiring unit that acquires insertion distance information indicative of a moving distance of the tip of the insertion member in the body lumen;
an additional vibration information generating unit that generates additional vibration information to change a magnitude of a vibration based on the insertion distance information acquired by the insertion distance information acquiring unit; and
an insertion position estimating unit that estimates a position of the tip of the insertion member with respect to the body lumen based on the insertion distance information acquired by the insertion distance information acquiring unit and generates the additional vibration information depending on the position of the tip of the insertion member with respect to the body lumen, thereby outputting the additional vibration information to the additional vibration information generating unit,
wherein the additional vibration information generating unit outputs, to the operation information generating unit, the additional vibration information acquired by the insertion position estimating unit.

13. The control apparatus of an insertion apparatus according to claim 12, wherein
the insertion position estimating unit generates additional vibration information to reduce a magnitude of a vibration with a longer insertion distance based on the insertion distance information acquired by the insertion distance information acquiring unit.

14. An insertion apparatus comprising the control apparatus of an insertion apparatus according to claim 1.

15. A method of controlling an insertion apparatus that inserts an insertion member of a catheter into a body lumen, the method comprising:
acquiring tip movement information indicative of presence of movement in the body lumen of a tip of the insertion member by a tip movement information acquiring unit;
acquiring non-tip area movement information indicative of presence of a moving operation in the body lumen of a non-tip area other than the tip of the insertion member by a non-tip area movement information acquiring unit;
by a state specifying unit by using the non-tip area movement information acquired by the non-tip area movement information acquiring unit and the tip movement information acquired by the tip movement information acquiring unit,
(a) specifying as a first tip stop state for vibrating the insertion member with a first magnitude of a vibration, a case where the non-tip area of the insertion member is moved and the tip of the insertion member is not moved, and
(b) specifying as a second tip stop state for vibrating the insertion member with a second magnitude of a vibration greater than the first magnitude of the vibration in the first tip stop state of (a), a case where the non-tip area of the insertion member is not moved and the tip of the insertion member is not moved;
generating operation information about the insertion apparatus to execute the first tip stop state of (a) or the second tip stop state of (b) which is specified by the state specifying unit, by an operation information generating unit; and
controlling an operation of the insertion member based on the operation information generated by the operation information generating unit, by a control unit,
wherein a maximum value of the second magnitude of the vibration in the second tip stop state is set to be an amplitude of 0.3 mm, and
the control unit controls the operation of the insertion member by applying vibration control to execute the vibrating of the insertion member in the first tip stop state of (a) or the second tip stop state of (b).

16. A computer readable recording medium recording a control program for a control apparatus of an insertion apparatus that inserts an insertion member of a catheter into a body lumen, the program for causing a computer to function as:
a tip movement information acquiring unit that acquires tip movement information indicative of presence of movement in the body lumen of a tip of the insertion member;
a non-tip area movement information acquiring unit that acquires non-tip area movement information indicative of presence of a moving operation in the body lumen of a non-tip area other than the tip of the insertion member;
a state specifying unit that, by using the non-tip area movement information acquired by the non-tip area movement information acquiring unit and the tip movement information acquired by the tip movement information acquiring unit,
(a) specifies as a first tip stop state for vibrating the insertion member with a first magnitude of a vibration, a case where the non-tip area of the insertion member is moved and the tip of the insertion member is not moved, and
(b) specifies as a second tip stop state for vibrating the insertion member with a second magnitude of a vibration greater than the first magnitude of the vibration in the first tip stop state of (a), a case where the non-tip area of the insertion member is not moved and the tip of the insertion member is not moved;
an operation information generating unit that generates operation information about the insertion apparatus to execute the first tip stop state of (a) or the second tip stop state of (b) which is specified by the state specifying unit; and
a control unit that controls an operation of the insertion member based on the operation information generated by the operation information generating unit,
wherein a maximum value of the second magnitude of the vibration in the second tip stop state is set to be an amplitude of 0.3 mm, and
the control unit controls the operation of the insertion member by applying vibration control to execute the vibrating of the insertion member in the first tip stop state of (a) or the second tip stop state of (b).

17. A controlling integrated electronic circuit of an insertion apparatus that inserts an insertion member of a catheter into a body lumen, the circuit comprising:
- a tip movement information acquiring unit that acquires tip movement information indicative of presence of movement in the body lumen of a tip of the insertion member;
- a non-tip area movement information acquiring unit that acquires non-tip area movement information indicative of presence of a moving operation in the body lumen of a non-tip area other than the tip of the insertion member;
- a state specifying unit that, by using the non-tip area movement information acquired by the non-tip area movement information acquiring unit and the tip movement information acquired by the tip movement information acquiring unit,
- (a) specifies as a first tip stop state for vibrating the insertion member with a first magnitude of a vibration, a case where the non-tip area of the insertion member is moved and the tip of the insertion member is not moved, and
- (b) specifies as a second tip stop state for vibrating the insertion member with a second magnitude of a vibration greater than the first magnitude of the vibration in the first tip stop state of (a), a case where the non-tip area of the insertion member is not moved and the tip of the insertion member is not moved;
- an operation information generating unit that generates operation information about the insertion apparatus to execute the first tip stop state of (a) or the second tip stop state of (b) which is specified by the state specifying unit; and
- a control unit that controls an operation of the insertion member based on the operation information generated by the operation information generating unit,
- wherein a maximum value of the second magnitude of the vibration in the second tip stop state is set to be an amplitude of 0.3 mm, and
- the control unit controls the operation of the insertion member by applying vibration control to execute the vibrating of the insertion member in the first tip stop state of (a) or the second tip stop state of (b).

* * * * *